(12) United States Patent
Vetter et al.

(10) Patent No.: US 8,450,097 B2
(45) Date of Patent: *May 28, 2013

(54) PROTEIN-PROTEOPHORE COMPLEXES

(75) Inventors: Dirk Vetter, Heidelberg (DE); Ulrich Hersel, Heidelberg (DE); Harald Rau, Heidelberg (DE); Robert Schnepf, Dossenheim (DE); Thomas Wegge, Heidelberg (DE)

(73) Assignee: Ascendis Pharma GmbH (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/967,285

(22) Filed: Dec. 14, 2010

(65) Prior Publication Data

US 2011/0172390 A1 Jul. 14, 2011

Related U.S. Application Data

(63) Continuation of application No. 10/574,213, filed as application No. PCT/EP2004/010973 on Oct. 1, 2004, now Pat. No. 7,879,588.

(30) Foreign Application Priority Data

Oct. 2, 2003 (EP) .................... 03022097

(51) Int. Cl.
*C12N 9/48* (2006.01)
*A61K 48/00* (2006.01)
*A61K 38/48* (2006.01)

(52) U.S. Cl.
USPC .......... 435/212; 424/1.45; 514/5.9; 514/11.3; 514/11.4; 977/700; 977/702; 977/705; 977/754

(58) Field of Classification Search
None
See application file for complete search history.

(56) References Cited

U.S. PATENT DOCUMENTS

| 4,507,466 A | 3/1985 | Tomalia et al. |
|---|---|---|
| 5,519,142 A | 5/1996 | Hoess et al. |
| 5,643,575 A | 7/1997 | Martinez et al. |
| 5,714,166 A | 2/1998 | Tomalia et al. |
| 6,410,680 B1 | 6/2002 | Kubota |
| 2002/0054863 A1 | 5/2002 | Malik et al. |
| 2003/0171285 A1 | 9/2003 | Finn et al. |

FOREIGN PATENT DOCUMENTS

| EP | A-0-618-192 A1 | 10/1994 |
|---|---|---|
| WO | WO-88/01180 | 2/1988 |
| WO | WO-95/24221 A1 | 9/1995 |
| WO | WO-96/31231 | 10/1996 |
| WO | WO-96/31231 A1 | 10/1996 |
| WO | WO-99/30727 A1 | 6/1999 |
| WO | WO-0078302 | 12/2000 |
| WO | WO-01/07469 | 2/2001 |
| WO | WO-01/07469 A2 | 2/2001 |
| WO | WO-01/21197 A1 | 3/2001 |
| WO | WO-02068454 A2 | 9/2002 |
| WO | WO-03/000777 | 1/2003 |
| WO | WO-03/030829 A2 | 4/2003 |
| WO | WO-03/057716 | 7/2003 |
| WO | WO-2004060977 | 7/2004 |

OTHER PUBLICATIONS

Jansen et al., "The Dendritic Box; Shape-Selective Liberation of Encapsulated Guests", American Chemical Society. 1995, vol. 117, pp. 4417-4418.

Van Hest et al., "Polystyrene—Poly(propylene imine) Dendrimers: Synthesis, Characterization, and Association Behavior of a New Class of Amphiphiles", Chem. Eur. J., 1996, vol. 2, No. 12, pp. 1616-1626.

Gorman, C.B., et al., "Dendritic Encapsulation as Probed in Redox Active Core Dendrimers", C.R. Cimie, 2003, vol. 6 (8-10), pp. 911-918.

Giehm, et al., "Dendrimers Destabilize Proteins in a Generation-Dependent Manner Involving Electrostatic Interactions", Biopolymers, 2008, vol. 89, No. 6, pp. 522-529.

Jansen, J.F.G.A. et al., Encapsulation of Guest Molecules into a Dentritic Box, Science, American Association for the Advancement of Science, US, vol. 266, No. 5188, Nov. 8, 1994, p. 1226-29.

Harris et al., Effects of Pegylation on Pharmaceuticals, Nature (Mar. 2003) vol. 2, p. 214-221.

Tracy, M. A., Development and Scale-up of a Microsphere Protein Delivery System, Biotechnol. Prog., American Chemical Society and American Institute of Chemical Engineers Jan. 16, 1998, vol. 14 p. 108-115.

Hermanson, G.T. Bioconjugate Techniques, Academic Press San Diego, USA 1996 (Table of Contents p. vii-xx).

Lee, S. et al., Drug Delivery Systems Employing 1,6 Elimination: Releaseable Poly(ethylene glycol) Conjugates of Proteins, Bioconjugate Chem., American Chemical Society, vol. 12 (2001) p. 163-69.

Vogtle, Fritz ed., Dendrimers II: Architecture, Nanostructure and Supramolecular Chemistry, Springer Verlag 2000 (Table of Contents).

*Primary Examiner* — Chris R Tate
*Assistant Examiner* — Aaron J Kosar
(74) *Attorney, Agent, or Firm* — Novak Druce Connolly Bove + Quigg LLP

(57) ABSTRACT

The application relates to a composition comprising a hyper-branched polymer attached to a core and a biologically active moiety. The biologically active moiety is attached to the core by means of a substantially non-enzymatically cleavable linker L. The composition can be used to deliver the biologically active moiety to its target.

9 Claims, 6 Drawing Sheets

PROTEIN-PROTEOPHORE COMPLEXES

RELATED APPLICATIONS

This application is a continuation of U.S. application Ser. No. 10/574,213 filed Oct. 9, 2006, which issued on Feb. 1, 2011 as U.S. Pat. No. 7,879,588, which is the national stage application (under 35 U.S.C. 371) of PCT/EP2004/010973 filed Oct. 1, 2004 which claims benefit of European Patent application 03022097.4 filed Oct. 2, 2003.

The present invention relates to inclusion compounds comprising a protein and an encapsulating organic compound (EOC), which will also be referred to as proteophore, in a 1:1 stoichiometrie. In one embodiment, the EOC is a dendrimer, resulting in a dendrimer-protein inclusion compound (DPIC). In a further embodiment, the EOC is a macrocyclic structure resulting in a macrocycle-protein inclusion compound (MPIC). The encapsulating compounds, as well as the resulting inclusion compounds, are water soluble and lend themselves for the controlled release of the protein to a target, preferably in a living body, in particular a mammal.

Proteins are large and unstable molecules. A large amount of proteins is known which show an important pharmacological activity. Examples include insulin, interferon, growth hormones and blood forming factors. In general, proteins are applied to mammals and humans by injection. To date, it is not possible to apply pharmacologically active proteins orally or transdermally. Following the injection, the proteins are readily attacked and often partially or totally eliminated by the immune system, various enzymes or kidney filtration. In addition, the protein can be toxic or cause allergic reactions.

In order to overcome the in-vivo elimination, several techniques were developed in order to ensure a controlled release of the respective protein. Examples include modification of the protein sequence, pegylation, proteinylation, binding to albumin, glycosylation, formulation into hydrogels or encapsulation by microparticles, nanoparticles, dendrimers.

Supramolecular chemistry is directed towards the synthesis and analysis of inclusion compounds in which two or more components are associated through complete enclosure of one set of molecules in a suitable structure formed by another.

In such chemical host-guest systems, one molecular entity is complementary to a different, second entity. Complementarity can occur in shape or physicochemical properties or in a combination of both. In the case of shape complementarity, the host molecule forms a cavity of size similar to the guest molecule. In such topologically well-defined cases, where the cavity is an inherent structural feature of a single molecule, the host is termed cavitand, and the host-guest aggregate cavitate. Typically, the stoichiometry of the supramolecular system is 1:1. Nevertheless, various types of complex stoichiometries are known. Guest molecules are typically smaller in size than the corresponding host compound.

Examples for small host-guest systems are for instance complexes formed between crown ethers and sodium or potassium ions. Well-known examples for synthetic organic host-guest molecules are the complexation of aromatic compounds such as nitrophenol by cyclodextrin carbohydrates. Cyclodextrins come in various ring sizes, the larger of which can accommodate bicyclic structures such as naphthalene and derivatives. Fullerene molecules are of spherical shape and accommodate free space of a diameter of 0.7 nm.

Biomacromolecules such as starch can form inclusion complexes with small guests such as iodine by filling a channel-like volume in the interior of a helix. DNA double helices are known to accommodate rigid aromatic compounds by means of intercalation. Serum albumin is a well-studied example of a protein that can be loaded with several molecules of fatty acids.

Comparatively little research has been undertaken to investigate the complexation of biomacromolecules such as proteins by synthetic host compounds.

A large number of molecular medicines are based on proteins or peptides of which group insulin, interferons, growth hormones and blood factors are among the most widely used therapeutics.

Protein therapeutics are known to suffer from various drawbacks. Proteins are inherently instable macromolecules as their bioactivity depends upon the correct three-dimensional positioning of its polypeptide chain. External factors such as solvents, surfaces, agitation, temperature or pH may effect the conformational equilibrium and result in partial or total unfolding, denaturation, agglomeration or precipitation. Proteins of non-human origin or proteins containing non-human amino acid sequences are highly immunogenic. Antibody formation is even notable for human proteins such as insulin if frequently administered by injection. Biomolecules may be cleared from circulation too fast or too slow for a given therapeutic application and may exhibit a narrow therapeutic window. Proteins can be degraded by endogenous proteases. Most therapeutic biomolecules need to be administered parenterally, often imposing the need for lifetime daily injections on the patient. At this point in time there are no approved protein formulations for oral or pulmonary delivery. Only in a few cases has it been possible to direct the therapeutic protein to the diseased tissue or cell type or to deliver the protein in an intracellular fashion.

Therefore it is highly desirable to develop molecularly defined delivery vehicles to enhance the therapeutic benefit of protein-based medication. Specifically, proteins need to be efficiently encapsulated for protection and released from the encapsulating agent for bioactivity.

Proteins are composed of condensated amino acid sequences that fold into a compact three-dimensional arrangement, often of globular shape. The diameter for globular proteins typically ranges from 1 to 10 nm. Proteins can form complexes comprised of several identical or different subunits, and several proteins can associate to form even larger complexes. A protein encapsulating agent has to provide a well-hydrated internal volume of a similar size and approximately spherical or ellipsoidal or channel-like shape. The water content is an important molecular property, as most biomolecules depend on a hydration shell for bioactivity.

Polymers have proven highly useful in delivery of therapeutic molecular biological material to humans. Linear or branched water soluble polymers can occupy a volume of similar size or greater than a protein molecule.

Polyethyleneglycol (PEG) is a polymer of low toxicity and immunogenicity. Various therapeutic proteins have been covalently conjugated to PEG by a process called PEGylation and successfully applied in molecular therapy (Harris J M, Chess R B, Nature (2003) 214-21).

An advantage of protein PEGylation is the improvement of pharmacokinetic properties of the conjugate in circulation. Unconjugated proteins such as interferon alfa-2a are cleared rapidly within 2.5 h in rats, the corresponding PEGylated interferons circulate with a half-life of $t\frac{1}{2}=3.4$ h (linear 5 kDa PEG monoconjugate) up to 23 h (dipegylated with 2×20 kDa PEG). This effect is attributed to reduced renal filtration. Kidney filtration is partially a size-exclusion process, and enhancing the hydrodynamic radius of a protein by PEGylation can significantly reduce its rate of clearance. PEG is strongly hydrated (2-3 water molecules per ethyleneoxide unit) and therefore displays a high apparent molecular weight in size exclusion chromatography studies. Due to its high conformational flexibility and hydration, PEG molecules appear 5-10 times as large as proteins of similar molecular mass.

PEG is widely used to render surfaces protein adsorption resistant and to precipitate proteins from aqueous solution, corroborating the notion that PEG does not physicochemically bind to protein.

The property of PEG to fold randomly and to occupy a large molecular volume explains also for the second therapeutic benefit of PEGylation, namely the reduction of immunogenicity of proteins. This effect is most pronounced for proteins of non-human origin and is likely to be achieved by imposing a steric shield in the vicinity of the immunogenic epitope and thereby preventing recognition by the immune system.

The shielding effect may be enhanced by employing branched PEG. Polyethylene glycol with a low degree of branching is known from U.S. Pat. No. 5,643,575 and the 2003 catalogue of Nektar Therapeutics. WO 01/21197 mentions branched monosubstituted insulin-PEG conjugates.

The steric shielding mechanism explains for the observed reduction of bioactivity of PEGylated proteins. Covalent conjugation of protein side chains close to an epitope generally may impair the ability of the protein to bind to its receptor. Care has to be taken to identify a reactive protein side chain that is in a distal position to the region of the protein surface that is mediating receptor binding or enzymatic activity. For this reason, PEG monoconjugation is preferred over multiple conjugation. Nevertheless even for monoconjugates, various regioisomers are obtained in various ratios.

Steric shielding may also be enhanced by conjugating the protein to more than one PEG molecule. Multiple PEGylation leads to an apparent increase in hydrodynamic volume and serves better to protect the protein from antibody recognition or protease attack. The approach is compromised by loss of bioactivity, loss of therapeutic activity per gram of material and by increasing the risk of protein inactivation by conformational destabilization.

It is a challenge to obtain a homogeneous product from the reaction of protein with PEG reagent. If a PEG reagent is reacted with a given protein under equimolecular conditions or added in slight excess, mono-, bis-, tris- and oligo-conjugations are commonly obtained. The reason is that protein surfaces display various functional groups of similar reactivities. The difficulties in analysis of such mixtures is aggravated by the fact that PEG in itself is a polydisperse molecule. Polydispersity relates to the fact that PEG cannot be obtained as a molecule of precise chain length beyond a degree of polymerization (dp) of 12 ethyleneglycol units. Typical PEGs of MW 5 kDa or 20 kDa exhibit polydispersities of 1.01 up to 1.20 respectively.

Non-water soluble polymers such as poly(lactide-co-glycolide, PLG) may form nano- or microparticles if precipitated from aqueous solution under certain conditions. The formed particles are not water-soluble but are suspended in aqueous solution. Proteins present in the aqueous phase may be entrapped inside these non-covalent assemblies. Proteins are released as the particles degrade. Such hydrogels are successfully used in slow release formulations of therapeutic proteins such as growth hormone (Tracy M A, Biotechnol Prod 14 (1998) 108-15).

Proteins or polypeptides may be incorporated in polymeric material by carrying out the polymerization step in the presence of the biomolecule. Insulin has been loaded to n-butylcyanoacrylate nanoparticles in this fashion (WO 96/31231). Polymerizing monomers are highly reactive molecular species and the process usually requires organic solvents. Biomacromolecules may suffer structural modification or degradation under such conditions.

Typical encapsulation methods involving prepolymerized entities are water-in-oil-in-water (w/o/w) double emulsion/solvent evaporation or the solid-in-oil-in-water (s/o/w) technique. The encapsulation process involves organic solvents such as methylene chloride, heat and sonication or homogenization and therefore can lead to inactivation of the encapsulated material.

An alternative method is based on polymer crosslinking. Proteins may be permanently entrapped in polymers if the crosslinking step is carried out in the presence of the protein. Protein, monomers and crosslinker are mixed and polymerized. Such polymers are not soluble per se. Crosslinked polymers are constituted of a network of polymer chains. Within this network various pores and cavities and channels exist in a random fashion, some of which may be sufficiently large to allow for diffusion of protein into, through or out of the polymer. The degree of crosslinking has a strong effect on diffusion into and effusion from the polymer. Products from such crosslinking are called hydrogels, as they can be produced from water-soluble, well-hydrated components and exhibit considerable swelling behaviour.

All of these methods of preparation may have severely detrimental effects on the protein integrity and bioactivity. As a portion of the protein material is inactivated during the particle preparation process, and it is difficult to quantify the remaining bioactivity of the entrapped protein sample.

Even after encapsulation, the protein is put under stress as the protein is forced to make tight contact with the more hydrophobic polymer molecules. This again may cause additional denaturing and loss of activity. Additionally, the molecular architecture of the polymer network imposes mechanical and physicochemical stress on the protein. The protein may be dehydrated or denatured by aggregation or contact to internal surfaces, and it is difficult to analyze the protein's bioactivity after encapsulation.

The release of proteins from the entrapment can be achieved by diffusion, a chemical or enzymatic reaction leading to degradation of the polymer or solvent activation (through osmosis or swelling) or a combination of mechanisms. For therapeutic applications, effusion, swelling or biodegradation mechanisms take place in vivo and are difficult to control.

Liposomes can form small unilamellar vesicles or large, multilamellar assemblies (Refs). The encapsulation of drugs in liposomes has been studied extensively and is applied in molecular therapy. WO 03/030829 describes liposome-encapsulated insulin formulations. Typical techniques such as mixing the drug with the lipid in an organic solvent, addition of an aqueous medium and subsequent removal of the organic solvent or dialysis of mixed lipid-detergent micelles are not readily applied to protein encapsulation due to protein denaturation by solvent or detergent. A more suitable approach is lipid film hydration. Liposomes are formed by hydrating and dispensing a previously dried film of lipid. Liposomes are not per se water-soluble but can be homogeneously distributed in water by means of dispersion. If protein is present in the hydration solution it becomes both associated on the surface and entrapped in the interior of the liposomes. The process reduces the exposure of protein to denaturing conditions but is of little encapsulation efficiency.

Dendrimers are well-defined polymeric structures. Dendrimers are based on repeating hyperbranched structures emanating from a central core (U.S. Pat. No. 4,507,466).

Typical dendrimers are based on polyamidoamine (PAMAM), polyethylene imine (PEI), polypropylene imine or polylysine. These synthetic macromolecules are assembled in a stepwise fashion, with each reaction cycle adding another layer of branches (dubbed "generation"). Dendrimers are synthetically accessed by stepwise, divergent "bottom-up" or convergent "top-down" synthesis. Central structural component is the core unit from which hyperbranched dendrimers extend in a radially symmetric fashion. The core may provide at least two reactive groups for dendrimer conjugation, it may also be of heterofunctional nature and protecting groups may be used. In the latter case, the dendrimer may be assembled, and a guest compound may be subsequently conjugated to an anilin core by means of orthogonal chemistries (WO 88/01180). The core and dendrimers form the interior or backbone of a dendrimer. As a consquence of the spherical symmetry supported by sterical crowding, the terminal groups of the hyperbranches are defining the exterior. In higher generation dendrimers, the terminal branches form rather dense shells and flexible internal voids have been discovered. It is understood, that for a given dendrimer these cavities are filled up by backfolded end groups and tightly coordinated solvent molecules. Dendrimers are related to micelles, similarly well suited to complex hydrophobic compounds. But in contrast they exhibit higher structural order because of their monomolecular nature and the absence of a dynamic equilibrium of various species. Synthetic compounds can only diffuse into dendrimers if certain structural requirement such as conformational rigidity and flatness as well as charge distribution such as affinity to tertiary amines are met. Various apolar compounds such as pyrene or naphthalene have been encapsulated in dendrimers, but the number of trapped guests as well as their molecular interaction with the dendrimer interior are rater undefined and frequently substoichiometric.

In U.S. Pat. No. 5,714,166 and WO 95/24221, dendrimer-protein conjugates are revealed. PAMAM dendrimers of G4 are covalently coupled through their terminal functional groups to insulin, fluorescently labeled insulin, avidin, monoclonal antibodies and bradykinin. The reactive groups used for conjugation are only present at the surface of the dendrimers, and therefore any covalent adduct generated by the teached method will be associated with the dendrimer exterior. Sterical "congestion" of the dendrimeric terminal groups is a prerequisite to the formation of internal void space.

In a scanning transmission electron micrograph study, it was observed that PAMAM dendrimers undergo a morphological change at the G9 stage. Surface congestion created a hollow interior surrounded by a dense rim. The G4 dendrimers used for protein conjugation do not contain such voids. Furthermore it is apparent from molecular size comparison, that a 3 nm sized insulin may not be encapsulated in a dense, 4 nm-sized generation 4 PAMAM dendrimer. Hemoglobin has a diameter of 5.5 nm, and PAMAM dendrimers of G5, G6 and G7 exhibit diameters of 5.3 nm, 6.7 and 8.0 nm respectively. Macromolecules such as peptides and proteins are per se excluded from diffusion through the dense molecular packing and entering the interior of such dendrimers. As the dendrimer surface is rather densely clustered, pore sizes are too small to allow for an entry of a protein into the dendrimer interior. For these reasons, macromolecular protein or polypeptide guests have not been encapsulated in dendrimers, neither has the non-covalent encapsulation of proteins been demonstrated.

PAMAM dendrimers contain free amine groups on their surfaces and readily associate with DNA through electrostatic interactions.

WO 01/07469 details water-soluble polypeptide dendrimers constituted of ornithin and glycine amino acids. The patent application also teaches the non-covalent encapsulation of an oligosaccharide, heparin, by dendrimerization of the dendrimer core in presence of heparin under mild conditions. The oligosaccharide is released from the dendrimer by light-induced cleavage of UV-labile bonds within the dendritic backbone. The core structure used here was tris(2-maleimidoethyl)amine Presynthesized polypeptide dendrimers, containing a free thiol group were incubated in DMF in the presence of heparin. This approach is unlikely to be applicable to proteins as substantial side reactions between the maleimido core and the protein will occur, furthermore steric competition will prevent an efficient encapsulation as either full formation of the tri-dendritic structure is prevented or the protein will not be entrapped. The example does not teach how to generate a complex of well-defined stoichiometry.

There is a continuous need for techniques and devices which allow for an effective encapsulation of proteins in order to ensure a controlled delivery and, if appropriate, release of pharmacologically active proteins. The encapsulation should not alter the proteins' structure and properties and should efficiently protect the protein from attacks by the immune system and enzymes of the individual to which the protein is administered. Furthermore, the protein should enable an efficient release of the encapsulated protein, in case this is desired.

This object is attained by a protein encapsulated covalently or non-covalently by an encapsulating organic compound (EOC) wherein the protein and the encapsulating organic compound are present in 1:1 stoichiometry.

Appropriate EOCs are water soluble.

The EOCs contain several, i.e. at least 2, molecule chains of an appropriate length which chains can arrange such that a cavity is formed which can accommodate the protein and protect it from the action of enzymes, antibodies and the like. The molecule chains will hereinafter be referred to as "encapsulating molecular chains" EMC. The EMCs can be directly connected with each other, or via a chemical unit, often one or more so-called branching units (see below).

In the following, EMCs according to the present invention will be defined. This definition applies every time EMCs will be mentioned in the present application in a general form, either in connection with a general formula or in any other context.

The EMCs contain hydrophilic groups, in an appropriate ratio and amount with respect to hydrophobic groups which may be present in the EOC, to render the latter water soluble.

The EMCs are built up from linear, branched or cyclical alkyl chains. To render the hydrophobic alkyl chains more hydrophilic, hetero atoms like but not limited to S, N, O may be present within the chain. Further appropriate groups which can be present in the EMCs include (—S—S)—, amide —C(O)NH— or C(O)NR—, —S-succinimido, amino (—NR—), carboxylic ester (—C(O)O—), sulfonamide (—S(O)$_2$—NR—), carbamate (—O—C(O)—NR—), carbonate (—O—C(O)—O—), sulfone (—S(O)$_2$—), ether (—O—), oxime (—CR=N—O—), hydrazone (—CR=N—NR—), urea (—NR—C(O)—NR—), thiourea (—NR—C(S)—NR—), carbohydrate, glyceryl, phosphate (—O—P(O)(OR)O—), phosphonate (—P(O)(OR)O—), saturated and nonsaturated (hetero)cyclic compounds. Non-limiting examples of R include H, linear, branched or cyclical alkyl groups which may contain further functional groups or hetero atoms. In addition to the afore-mentioned groups, further groups known to the person skilled in the art can be present in the EMCs.

Example for preferred groups in the EMCs comprise oxyalkylene groups (i.e. oxyethylene (—OCH$_2$CH$_2$)—, oxypropylene groups (—OCH$_2$CH(CH$_3$))— and oxybutylene groups) and amide groups (—C(O)NH—. It is preferred if the EMCs comprise oxyethylene groups (—OCH$_2$CH$_2$)— and amide groups (—C(O)NH)—.

In one embodiment of the present invention, the EMCs comprises at least one amino acid unit in its chain. In the context of the present invention, "amino acid unit" means an amino acid, preferably a naturally occurring amino acid like lysine, which is connected to at least one further binding partner, for example a further amino acid, by its amino and/or its carboxy function. The amino acid may be modified, e.g. carry one or more substituents.

The EMCs can carry one or more substituents (capping groups or modifiers C) on their backbone. Appropriate capping groups are sterically demanding groups. The capping groups will in particular be present if the EMCs require sterically demanding groups forcing them into a certain conformation necessary for the creation of the cavity enclosing the protein. In many cases, the EMCs according to the present invention are not rigid, and the subunits of the EMCs may rotate around the bonds of the chain and occupy a spatial position in accordance with the sterical requirements (which, in general, will be the position with the lowest energy). The capping groups can avoid a too close approaching of the EMCs and an opening of the cavity which may result in an insufficient encapsulating of the protein and an insufficient protection from the attack of enzymes, antibodies or the like.

Furthermore, the protein may totally leave the cavity through the gap resulting from the movement of the EMCs.

The capping groups C are built up from linear, branched or cyclical alkyl chains. To render the hydrophobic alkyl chains more hydrophilic, hetero atoms like but not limited to S, N, O may be present within the chain. Further appropriate groups which can be present in the capping groups include (—S—S—)—, amide —C(O)NH— or C(O)NR—, —S-succinimido, amino (—NR—), carboxylic ester (—C(O)O—), sulfonamide (—S(O)$_2$—NR—), carbamate (—O—C(O)—NR—), carbonate (—O—C(O)—O—), sulfone (—S(O)$_2$—), ether (—O—), oxime (—CR=N—O—), hydrazone (—CR=N—NR—), urea (—NR—C(O)—NR—), thiourea (—NR—C(S)—NR—), carbohydrate, glyceryl, phosphate (—O—P(O)(OR)O—), phosphonate (—P(O)(OR)O—), saturated and nonsaturated (hetero)cyclic compounds. Non-limiting examples of R include H, linear, branched or cyclical alkyl groups which may contain further functional groups or hetero atoms. In addition to the aforementioned groups, further groups known to the person skilled in the art can be present in the EMCs.

In one embodiment of the present invention, the capping units comprise at least one amino acid unit in its chain. In the context of the present invention, "amino acid unit" means an amino acid, preferably a naturally occurring amino acid like lysine, which is connected to at least one further binding partner, for example a further amino acid, by its amino and/or its carboxy function. The amino acid may be modified, e.g. carry one or more substituents.

It is preferred if the capping groups comprise oxyalkylene groups (i.e. oxyethylene (—OCH$_2$CH$_2$)—, oxypropylene groups (—OCH$_2$CH(CH$_3$))— and oxybutylene groups) and amide groups (—C(O)NH)—. It is even more preferred if the capping groups comprise oxyethylene groups (—OCH$_2$CH$_2$)— and amide groups (—C(O)NH)—, in an appropriate ratio and amount, in order to obtain capping groups with the desired hydrophilicity which may be higher or lower than the hydrophilicity of the EMCs.

The capping groups in the EMC can contain one or more functional groups from those cited above. The functional groups present in a given capping group can be identical or different. Each of the cited groups can be present only once or several times. The capping groups present in a given EMC can be identical or different.

In one embodiment of the present invention, the capping groups do not have a high branching degree. This will in particular be the case if the EOCs according to the present invention have a high number of EMCs.

In a further embodiment of the present invention, the capping groups are highly branched molecules having preferably a branching degree of 2, 3, 4, 5 or 6. A branching degree of 2 means that the principal chain connected to the encapsulating unit splits up into 2 subchains, whereas in the case of a branching degree of 3, the main chain splits up into 3 subchains, etc.

The subchains may themselves also be branched. In the context of the present invention, this case will be referred to as "subbranched" (The modifiers are subbranched, i.e. their main chain contains subchains which themselves are branched.) For example, in the case of a branching degree of 2, each of the 2 subchains can be subbranched to a subbranching degree of 2, meaning that also each of the 2 subchains into which the main chain (principal chain) splits up itself splits up into 2 subchains. In such case, the branching degree will be designated as 2(2).

When an EOC according to the present invention is substituted by capping groups which are highly branched, a dendritic structure will result.

The term hyperbranched polymer used in this description is intended to include a combination of an EMC with capping groups as well as EOCs.

In one embodiment of the present invention, the encapsulation is realized by an EOC-protein inclusion compound EPIC according to the formula (I) in which the EMCs are connected to each other by one branching unit B, resulting in an EOC of the structure according to the formula (II) in which a cavity is formed.

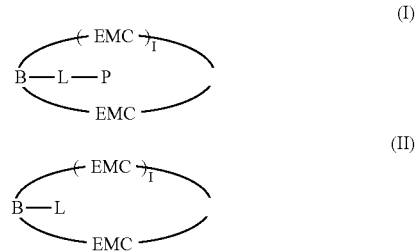

In the formulae (I) and (II), the symbols have the following meanings:

B: branching unit (basic unit, core) containing at least one branching center Bc and at least two branching functional groups Bfg connected to or capable of reacting with an encapsulating unit EMC;

EMC: encapsulating molecular chain;

L: linker containing at least one functional group Lfg which is connected to the protein P or capable of connecting with functional groups present on the protein P under the formation of a chemical bond;

l: 1, 2, 3, 4, 5, 6, 7, 8, 9, 10, 11 or 12, preferably 3, 4, 5, 6, 7 or 8, in particular 2, 3, 4, 5 or 6;

P: pharmacologically active protein.

The EMCs have been defined beforehand. In the following, the groups B, L and P according to the formulae (I) and (II) will be defined. This definition applies every time B, L and P will be mentioned in the present application in a general form, either in connection with a general formula or in any other context.

The EOCs according to the present invention may comprise more than 2 EMCs, for example 2, 3, 4, 5, 6, 7, 8, 9, 10, 11, 12 or 13. In the formulae below, some preferred embodiments are shown.

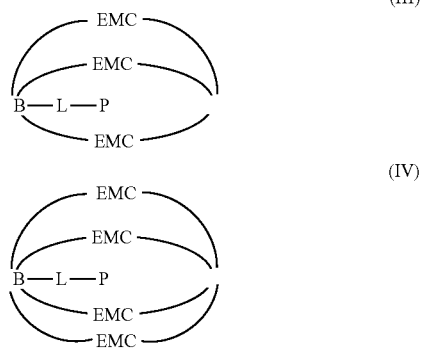

The branching units B can be regarded as the basic unit or core of the EMCs according to the present invention.

The EMCs are linked by an EMC functional group to at least one branching unit B. B contains at least one branching center Bc. Examples of Bc include units like >CH— or >C< and the respective analogues wherein H is replaced by an organic group; >N—; >P—. The centers Bc can directly be linked to the branching functional groups (see below), or can be linked to at least one organic chain.

Examples for appropriate organic chains include linear, branched or cyclical alkyl chains. Hetero atoms like but not limited to S, N, O may be present within the chain. Further appropriate groups which can be present in B include (—S—S—), amide —C(O)NH— or C(O)NR—, —S-succinimido, amino (—NR—), carboxylic ester (—C(O)O—), sulfonamide (—S(O)$_2$—NR—), carbamate (—O—C(O)—NR—), carbonate (—O—C(O)—O—), sulfone (—S(O)$_2$—), ether (—O—), oxime (—CR=N—O—), hydrazone (—CR=N—NR—), urea (—NR—C(O)—NR—), thiourea (—NR—C(S)—NR—), carbohydrate, glyceryl, phosphate (—O—P(O)(OR)O—), phosphonate (—P(O)(OR)O—), saturated and nonsaturated (hetero)cyclic compounds. Non-limiting examples of R include H, linear, branched or cyclical alkyl groups which may contain further functional groups or hetero atoms. In addition to the afore-mentioned groups, further groups known to the person skilled in the art can be present in B.

B can contain one or more groups chosen from those cited above. The groups can be identical or different. Each of the cited groups can be present only once or several times. In a preferred embodiment of the present invention, B comprises at least one amino acid unit, preferably of a naturally occurring amino acid like lysine. It is even more preferred if B contains a unit composed of several amino acid units.

In general, B will be a branched structure containing one or more of the above mentioned groups and having a certain length, in accordance with the steric requirements of the protein to be encapsulated. B will comprise one or more branching center. Furthermore, B will contain at least two branching functional groups Bfg allowing for the attachment of the EMCs.

Examples for suitable bond species formed between B and the EMC include the following: (—S—S—), S-succinimido, amide —C(O)NH— or C(O)NR—, —S-succinimido, amino (—NR—), carboxylic ester (—C(O)O—), sulfonamide (—S(O)$_2$—NR—), carbamate (—O—C(O)—NR—), carbonate (—O—C(O)—O—), ether (—O—), oxime (—CR=N—O—), hydrazone (—CR=N—NR—), urea (—NR—C(O)—NR—), thiourea (—NR—C(S)—NR—), phosphate (—O—P(O)(OR)O—), phosphonate (—P(O)(OR)O—).

Non-limiting examples of R include H, linear, branched or cyclical alkyl groups which may contain further functional groups or hetero atoms or aryl groups.

As will be apparent to the person skilled in the art from the foregoing, the functional groups present on the EMC and B (Bfg) of the EOC will be transformed (and changed) into a bond species. When, in the context of the present invention, reference is made to "functional group" present on B and the EMC, this refers to the functional groups as such, as well as to the bond species formed by reaction between the groups.

In the context of the present invention, "bond" or "chemical bond" refers to the attraction forces as such between two or more atoms (e.g. a "covalent bond"), whereas "bond species" denotes the chemical bond and the atoms in the vicinity which is involved in the binding process (e.g. —S—S—).

As the bond species depicted beforehand are formed by the reaction between functional groups (which functional groups can be identical or different), the EMCs and B before forming the bond species, both contain functional groups which are capable of reacting with each other under the formation of an appropriate chemical bond, preferably one of the bonds mentioned beforehand.

Examples for appropriate branching functional groups Bfg and EMC functional groups comprise amino (—NRH), carboxylic acid (—C(O)OH) and derivatives, sulfonic acid (—S(O)$_2$—OH) and derivatives, carbonate (—O—C(O)—O—) and derivativs, hydroxyl (—OH), aldehyde (—CHO), ketone (—CRO), hydrazine (H$_2$N—NR—), isocyanate (—NCO), isothiocyanate (—NCS), phosphoric acid (—O—P(O)(OR)OH) and derivatives, phosphonic acid (—P(O)(OR)OH) and derivatives, haloacetyl, alkyl halides, maleimide, acryloyl, arylating agents like aryl fluorides, hydroxylamine, disulfides like pyridyl disulfide, vinyl sulfone, vinyl ketone, diazoalkanes, diazoacetyl compounds, epoxide, oxirane, aziridine, Non-limiting examples of R include H, linear, branched or cyclical alkyl groups which may contain further functional groups or hetero atoms or aryl groups.

In a preferred embodiment of the present invention branching functional groups and EMC functional groups comprise amino, carboxylic acid and derivatives, hydrazine, hydroxylamine, thiol, aldehyde, hydroxyl, carbonate, maleimide or haloacetyl groups.

As already mentioned, B can contain two or more Bfgs. This is in particular the case when the EOC comprises more than four, for example 5, 6, 7, 8 or more EMCs.

Likewise B can contain one or more branching centers Bc.

A further essential constituent of the EOCs according to the present invention is the linker L which serves to establish a chemical bond between the protein P and the EOC, by the reaction between appropriate functional groups Lfg on the linker L and the protein. The chemical bond can be a covalent bond or a non-covalent bond, for example a coordinative bond. Preferably, the EOC has 1 or 2 linkers.

In the context of the present invention, several sorts of linkers can be employed:

Non-cleavable linker: a linker containing no selectively cleavable bonds.

Cleavable linker: a linker containing a bond that can be selectively cleaved by a cleavage reagent (TCEP, TFA, DTT, enzyme, or a buffer).

Traceless linker: a linker that upon cleavage releases protein in such a fashion that the protein is not associated with a remaining linker cleavage product.

Prodrug linker: a cleavable linker containing a bond that can be selectively cleaved under in-vivo conditions, for instance in the presence of endogenous enzymes or other endogenous reagents, or solely in aqueous buffer.

Traceless prodrug linkers: linkers having both the characteristics of prodrug linkers and traceless linkers.

Depending on the therapeutic application, the protein may need to be permanently encapsulated, and therefore non-cleavable stable linkers may be employed. This is exemplified in the preparation of hemoglobin-EOC conjugates. Hemoglobin requires the diffusion of oxygen through the EOC but the protein does not need to be released from its encapsulation for bioactivity. Corresponding linkers are known in the art (Hennanson G T, Bioconjugate Techniques, Academic Press San Diego, 1996).

In many cases, the release of the protein from the EOC/EPIC is mandatory for its bioactivity. One example is insulin which, in order to bind to its receptor, must diffuse out of the shielding EOC. Protein release may be achieved by cleaving the covalent tether between protein and EOC.

Cleavable linkers are known in the art (see Hermanson).

The linker L can react with any appropriate functional group Pfg present on the protein P, preferably with those mentioned below.

Examples for suitable bond species formed between the protein P and the linker L include the following: (—S—S)—, S-succinimido, amide —C(O)NH— or C(O)NR—, —S—succinimido, amino (—NR—), carboxylic ester (—C(O)O—), sulfonamide (—S(O)$_2$—NR—), carbamate (—O—C(O)—NR—), carbonate (—O—C(O)—O—), ether (—O—), oxime (—CR=N—O—), hydrazone(—CR=N—NR—), urea (—NR—C(O)—NR—), thiourea (—NR—C(S)—NR—), phosphate (—O—P(O)(OR)O—), phosphonate (—P(O)(OR)O—). Non-limiting examples of R include H, linear, branched or cyclical alkyl groups which may contain further functional groups or hetero atoms or aryl groups.

In the context of the present invention, "bond" or "chemical bond" refers to the attraction forces as such between two or more atoms (e.g. a "covalent bond"), whereas "bond species" denotes the chemical bond and the atoms in the vicinity which is involved in the binding process (e.g. —S—S—).

As the bond species depicted beforehand are formed by the reaction between functional groups (which functional groups can be identical or different), the EOC, before reacting with the protein, and the protein, before reacting with the EOC, both contain functional groups which are capable of reacting with each other under the formation of an appropriate chemical bond, preferably one of the bonds mentioned beforehand.

Examples for appropriate protein functional groups Pfg which are part of the amino acids forming the natural (i.e. non-modified) protein are amino, thiol, hydroxyl, phenol, imidazole, amide, indole, carboxylic acid and guanidino groups.

In a preferred embodiment of the present invention Pfgs comprise amino, imidazole and thiol groups.

Examples for appropriate linker functional groups comprise amino (—NRH), carboxylic acid (—C(O)OH) and derivatives, sulfonic acid (—S(O)$_2$—OH) and derivatives, carbonate (—O—C(O)—O—) and derivatives, hydroxyl (—OH), aldehyde (—CHO), ketone (—CRO), isocyanate (—NCO), isothiocyanate (—NCS), haloacetyl, alkyl halides, maleinaide, acryloyl, arylating agents like aryl fluorides, disulfides like pyridyl disulfide, vinyl sulfone, vinyl ketone, diazoalkanes, diazoacetyl compounds, epoxide, oxirane, aziridine, Non-limiting examples of R include H, linear, branched or cyclical alkyl groups which may contain further functional groups or hetero atoms or aryl groups.

In a preferred embodiment of the present invention Lfgs comprise carbamate, carbonate, thiol, thioether, succinimidyl, amide and disulfide.

As will be apparent to the person skilled in the art from the foregoing, the functional groups present on the protein P (Pfg) and the linker L (Lfg) of the EOC will be transformed (and changed) into a chemical bond. When, in the context of the present invention, reference is made to "functional group" present on the linker L and the protein P, this refers to the functional groups as such, as well as to the bond species formed by reaction between the groups.

A part of the present invention are traceless double prodrug linker structures and their EPICs resulting in a novel mechanism of cleavage and subsequent release of the protein from the EOC.

Many widely applied and commercially available protein linker reagents cleave in such a fashion, that part of the linker remains conjugated to the protein. As such linker fragments are of low molecular weight and if the site of conjugation does not involve an amino acid that is essential for receptor binding, the bioactivity of the therapeutic protein may be fully or partially retained.

More advantageous are cleavable, traceless linkers that release the protein in an unmodified form under in vivo conditions such as neutral pH without the addition of chemical or biological cleaving agents. Examples are double prodrugs which are based on linker moieties which are cleaved in a two-step process in vivo. WO 99/30727A1, which is incorporated herein by reference, reveals conjugates containing a PEG moiety, a double prodrug linker and protein. The advantage of such systems is that the protein is released in an unmodified form. The linker cleavage process is traceless, the protein end product of the cleavage step do not contain remnants of the linker structure. In a first, rate-determining step one bond is hydrolyzed. This is typically an ester bond, such as in a phenol ester, and hydrolysis may occur by enzymatic attack (lipases) or autohydrolysis or a combination of both. The resulting free phenol is instable and rapidly rearranges for instance through 1,4- or 1,6-arylelimination, and cleavage of a carbamate releases the protein, $CO_2$ and an instable aromatic moiety.

Furthermore, linker are known to the person skilled in the art that can be cleaved in such a fashion that after cleavage no parts of the linker remain at the EOC.

Thus, a preferred embodiment of the present invention are traceless prodrug linkers which contain an ester functionality, in particular a phenol ester functionality, and a carbamate functionality.

Examples for suitable linker reagents are those according to the formulae (1), (2), (5), (6) and (7).

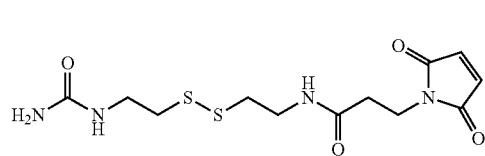

1

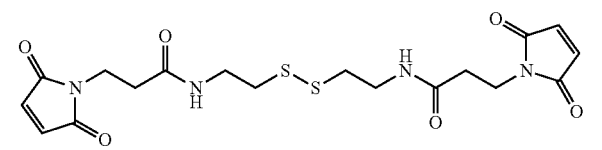

2

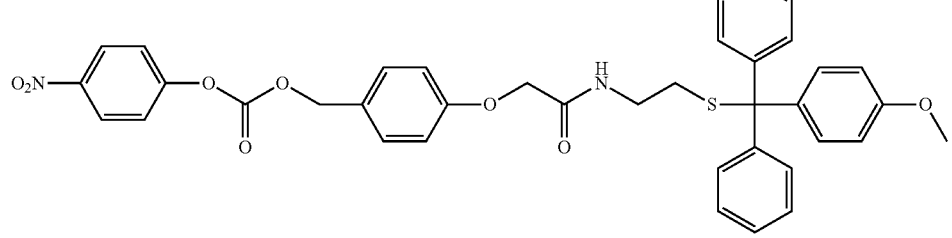

5

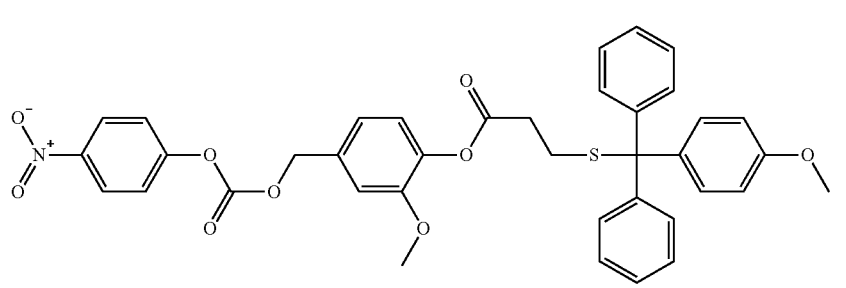

6

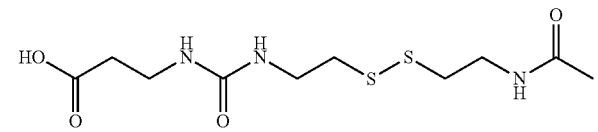

7

The most preferred linker reagent is the linker reagent according to the formula (II) below (traceless prodrug linker).

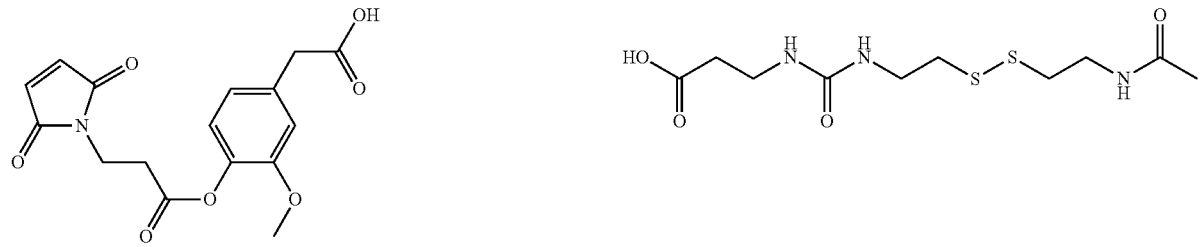

11

Lee S. Greenwald R B, McGuire J, Yang K, Shi C, Bioconjugate Chem 12 (2001) 163-9, which is incorporated herein by reference, reviewed double prodrug linkers employing 1,6-elimination for releasable PEG-protein conjugates. The use of such or related linkers for EOC-protein conjugates is within the scope of the present invention.

After the cleavage of the linker, a EPIC results in which the protein is not connected to the EOC via a linker (a chemical bond), but the protein is held within the cavity defined by the EOC. The resulting EPICs are an object of the present invention. It depends on the release kinetics of the protein if the respective EPIC having no bond between the protein and the EOC can be isolated as such.

In the EPICs according to the present invention, the protein can be encapsulated entirely or partially by the EOC. It is preferred to encapsulate the protein entirely, i.e. the cavity is of a size sufficiently large to accept the entire protein therein.

The EPICs according to the present invention can, in principle, accommodate any protein which has a physiological or pharmacological activity. These are known to the person skilled in the art. Important proteins can be found in standard text books which are known to the skilled artisan.

Relevant therapeutic proteins and polypeptides which can be encapsulated according to the present invention are: ACTH, adenosine deaminase, agalsidase, albumin, alfa-1 antitrypsin (AAT), alfa-1 proteinase inhibitor (API), alteplase, anistreplase, ancrod serine protease, antibodies (monoclonal or polyclonal, and fragments or fusions), antithrombin antitrypsins, aprotinin, asparaginases, biphalin, bone-morphogenic proteins, calcitonin (salmon), collagenase, DNase, endorphins, enfuvirtide, enkephalins, erythropoietins, factor VIla, factor VIII, factor VIIIa, factor IX, fibrinolysin, fusion proteins, follicle-stimulating hormones, granulocyte colony stimulating factor (G-CSF), galactosidase, glucagon, glucocerebrosidase, granulocyte macrophage colony stimulating factor (GM-CSF), gonadotropin chorionic (hCG), hemoglobins, hepatitis B vaccines, hirudin, hyaluronidases, idumonidase, immune globulins, influenza vaccines, interleukins (1 alfa, 1 beta, 2, 3, 4, 6, 10, 11, 12), IL-1 receptor antagonist (rhIL-1ra), insulins, interferons (alfa 2a, alfa 2b, alfa 2c, beta I a, beta 1b, gamma 1a, gamma 1b), keratinocyte growth factor (KGF), lactase, leuprolide, levothyroxine, luteinizing hormone, Lyme vaccine, natriuretic peptide, pancrelipase, papain, parathyroid hormone, PDGF, pepsin, platelet activating factor acetylhydrolase (PAF-AH), prolactin, protein C, octreotide, secretin, sermorelin, superoxide dismutase (SOD), somatropin (growth hormone), somatostatin, streptokinase, sucrase, tetanus toxin fragment, tilactase, thrombins, thymosin, thyroid stimulating hormone, thyrotropin, tumor necrosis factor (TNF), TNF receptor-IgG Fc, tissue plasminogen activator (tPA), TSH, urate oxidase, urokinase, vaccines.

Preferred proteins are antibodies, calcitonin, G-CSF, GM-CSF, mythropoietins, hemoglobins, interleukins, insulins, interferons, SOD, somatropin, TNF, TNF-receptor-IgG Fc.

The most preferred proteins are erythropoietins, interferons, insulins, somatropins and hemoglobins.

It is understood that the invention is not restricted to therapeutic proteins. Protection from aggressive environments is also desirable for other proteins such as amylases, proteases, peptidases, xylanases, lipases, lipoxygenases, cellulases, pectinases, phytases, oxidoreductases applied in industrial processes such as food and animal feed applications, as cleaning compounds in laundry detergents, dishwashing detergents, in the manufacture of chemicals such as alcohol, steroids and antibiotics, amino acids, proteins, triglycerides, phospholipids, and for textile, leather and fur applications, especially in the prebleaching of pulp.

All proteins, in particular those cited beforehand, can be encapsulated in a macrocyclic structure according to the present invention, to result in an MPIC, or in a dendrimer resulting in a DPIC.

The size of the cavity in the EOCs (i.e. the proteophors, macrocyclic structures and dendrimers) according to the present invention needs to be adapted to the proteins diameter. The size should be larger than the diameter of the smallest sphere that can be drawn around a correctly folded protein. From this diameter estimation, the length of the corresponding molecular chain in the EOC host can be calculated. In order to encapsulate insulin (approximately 3 nm diameter), a chain of at least 5 nm length that can fold into a halfcyclic conformation needs to be present in the EOC.

In a preferred embodiment of the present invention, the EMC's according to the formula (II) contain capping groups (C) which are arranged such that a dendritic structure of the EOC results. When such an EMC encloses a protein, dendrimer-protein inclusion compounds DPIC according to the formula (V) wherein a dendrimer (VI) encapsulates the protein result. Such DPICs are a part of the present invention. In the following formulae (V) and (VI) C denotes a capping group as defined beforehand and the other symbols have the meanings defined for formula (I).

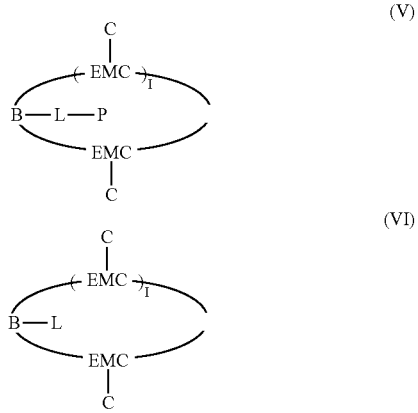

Embodiments of the capped EOCs having three and four EMCs are shown in the formulae (VII) and (VIII) below.

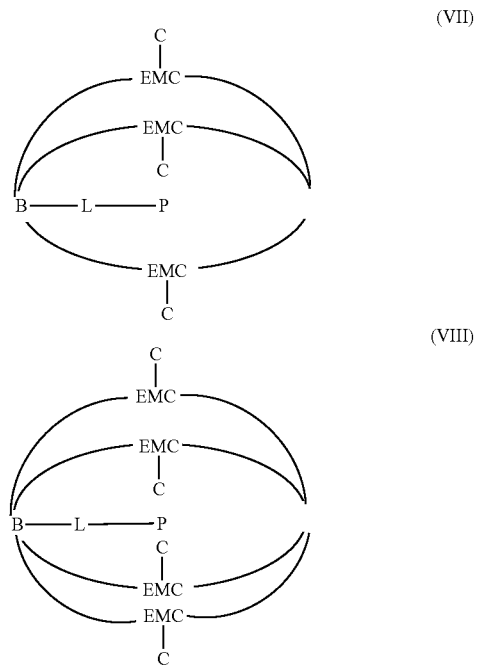

The DPICs according to the general formulae (V) to (VIII) show a 1:1 ratio protein/dendrimer. The DPICs are soluble in water. In general, the cavity of the dendrimer also comprises water, in addition to the protein.

Dendrimers are known to the person skilled in the art. Reference is made to: Dendrimer II Architecture, Nanostructure and Supramolecular Chemistry, Springer Verlag 2000, F. Vögtle Editor. Dendrimers are based on repeating hyperbranched structures emanating from a central core (U.S. Pat. No. 4,507,466). These synthetic macromolecules are assembled in a stepwise fashion, with each reaction cycle adding another layer of branches (dubbed "generation"). Dendrimers are synthetically accessed by stepwise, divergent "bottom-up" or convergent "top-down" synthesis. Central structural component is the core unit from which hyperbranched dendrimers extend in a radially symmetric fashion.

The dendrimers according to the present invention may contain, in the capping groups, centers branching into two, three, four, or more directions, preferably two.

The length of dendritic chains may be identical or vary between chains of one dendrimer. Preferred chain lengths for individual dendrimers are up to 5000 bonds.

By the choice of appropriate capping groups, it is perfectly possible to protect the encapsulated protein form the attack of e.g. antibodies or the elimination by the kidney or the liver.

The capping groups C have been defined above, which definition also applies here.

In all formulae (V) to (VIII) shown beforehand, an EMC can carry one capping group C (as shown in the formulae) or more than one, i.e. 2, 3, 4, 5, 6, 7, 8, 9, 10, 11, 12 or even more capping groups C.

In a preferred embodiment of the present invention, some capping groups in dendrimers according to the invention contain branched heterofunctional units carrying at least one thio-succinimido moiety. Thio-succinimido groups are the result of a reaction between a maleimido and a thiol group and can be obtained under mild conditions, proving useful for the synthesis of hyperbranched or dendritic structures. Further units which can be used in the synthesis of the dendrimers according to the present invention comprise tris-(2-maleimidoethy)amine and hydroxysuccinimide ester (EP-A 0 618 192).

Most useful for the divergent assembly of hyperbranches or dendrimers are heterofunctional reagents carrying both a maleimido as well as a protected thiol group. Such reagents may be employed for repeated stepwise synthesis in a similar fashion as for instance protected amino acids or protected nucleosides.

It was found that the dendrimers according to the present invention can efficiently be formed of multidentate compounds containing only one maleimide group and a number of protected thiols, in a divergent synthesis approach. The monomaleimido-tetrathio-dendrimer compounds according to the present invention are of the general formula M-A-(S-Pg)$_n$, with the following meanings: M: maleimido, A: spacer, S: sulfur, Pg: thiol protecting group, n: 2 to 200.

Suitable thiol protecting groups: benzyl, 4-methoxybenzyl, 2,4-dimethoxybenzyl-, 2,4,6-trimethoxybenzyl-(Tmob), 4,4'-dimethoxyphenylmethyl-(diMpm), trityl-, 4-methoxytrityl(Mmt), 4,4'-dimethoxytrithyl-(DMTr), 4,4',4''-trimethoxytrityl-(TMTr), tert.-butyl-MeCONHCH$_2$-(Acm), PhCH$_2$CONHCH$_2$— (PhAcm), MeOCOS-(Scm), BzlO-COS— (SZ) PhN(Me)COS-(5 nm), TrtS-, 2-pyridinesulfenyl-, 2-(3-nitropyridinesulfenyl), 4,5,6-trimethoxy-2,3-dihydro-7-benzofuranylmethyl-(Tmbf), 2-(2,4-dinitrophenyl)ethyl-(Dnpe), 9H-xanthen-9-yl-(Xan), 2-methoxy-9H-xanthen-9-yl-(Moxan), Fmoc-S-sulfonate.

Multidentate compounds are water soluble and the conjugation reactions will not compromise the biomolecule's structural integrity or bioactivity.

According to the present invention, the core of the DPIC is formed by the protein to be encapsulated which is connected (conjugated) to the polymer backbone by a suitable linker, in general one of the linkers listed above.

After the cleavage of the linker, a DPIC results in which the protein is not connected to the dendrimer via a linker (a chemical bond), but the protein is held within the cavity defined by the dendrimer. The resulting DPICs are an object of the present invention. It depends on the release kinetics of the protein if the DPIC having no bond between the protein and the dendrimer can be isolated as such.

In a further embodiment of the present invention, the EOCs comprise a second branching group B identical or different from the first branching group B to which the EMCs are connected, resulting in a cavity which is horizontally locked and vertically open. Thus, the encapsulation is realized by a macrocycle-protein inclusion compound WIC according to the formula (IX)

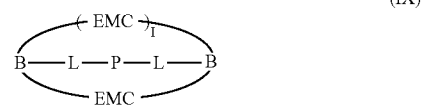

(IX)

containing a protein P and a macrocyclic structure encapsulating the protein totally or partially according to the general formula (X)

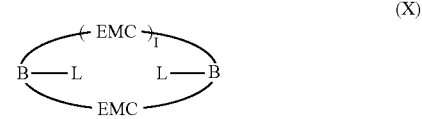

(X)

wherein the symbols in formulae (IX) and (X) have the following meanings:

B: branching unit (basic unit, core) containing at least one branching center Bc and at least two branching functional groups Bfg connected to or capable of reacting with an encapsulating unit EMC;

EMC: encapsulating molecular chain;

L: linker containing at least one functional group Lfg which is connected to the protein P or capable of connecting with functional groups present on the protein P under the formation of a chemical bond;

l: 1, 2, 3, 4, 5, 6, 7, 8 or 9, preferably 1, 2, 3, 4 or 5, in particular 1, 2 or 3;

P: pharmacologically active protein.

The MPICs according to the general formula (IX) show a 1:1 ratio protein/macrocyclic structure. The MPICs are soluble in water. In general, the cavity of the macrocyclic structure also comprises water, in addition to the protein.

The EMCs contain hydrophilic groups, in an appropriate ratio and amount with respect to hydrophobic groups which may be present in the macrocyclic structure, to render the latter water soluble.

B, EMC, L and P are in accordance with the definitions given above.

The macrocyclic structure and the MPIC according to the present invention comprise at least two EMCs (l=1). The macrocyclic structure can however comprise 3 (l=2), 4 (l=3), 5 (l=4), 6 (l=5) or even up to 10 EMCs. Some embodiments are depicted in the formulae (XI) and (XII) below.

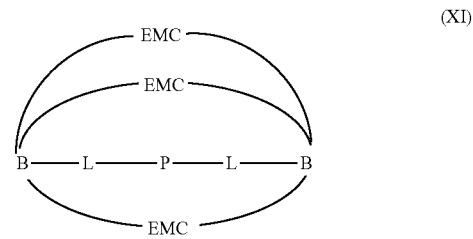

(XI)

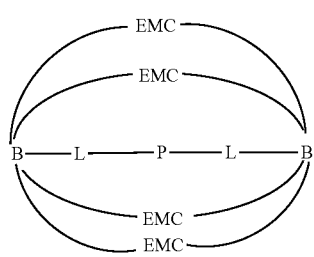
(XII)

The EMCs can all be identical, partly identical (partly different) or entirely different from each other.

The EMCs can carry capping groups C, as defined above, on their backbone. Appropriate capping groups are sterically demanding groups. The macrocyclic structures of the present invention are not rigid, and the EMCs, due to the rotation around the bonds connecting them to the branching units B, may swing to one side, resulting in a staggering and crowding on one side of the macrocyclic structure, and opening of one or more sides of the cavity. Capping groups prevent sterical proximity of the EMCs. If the EMCs come too close to one another, insufficient protection of the encapsulated protein from the attack of enzymes, antibodies or the like may result. Furthermore, the protein may leave the cavity (if the linker is broken) through the gap, resulting in an undesired release kinetics of the protein. In case capping groups are present, the following structures (XIII) and (XIV) result.

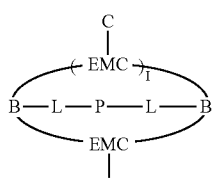
(XIII)

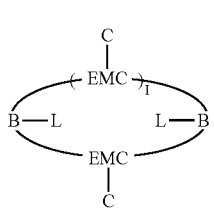
(XIV)

The figures (XV) and (XVI below show macrocyclic structures having capping groups on the three and four EMCs of the respective macrocyclic structure.

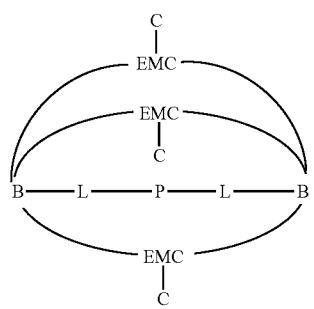
(XV)

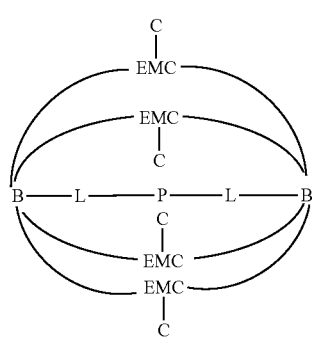
(XVI)

In all formulae (XI) to (XVI) shown beforehand, an EMC can carry one capping group C (as shown in the formulae) or more than one, i.e. 2, 3, 4, 5 or even more capping groups C.

Examples for EPICs, DPICs and MPICs wherein the linker has been cleaved and the protein is not held within the cavity by covalent bonds are depicted in the formulae (XVII) to (XX) below, which include examples in which traces of the linker remain at the EOC, dendrimer or macrocyclic structure, and examples wherein the linker has totally been removed.

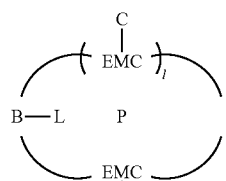
(XVII)

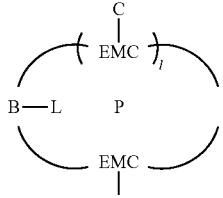
(XVIII)

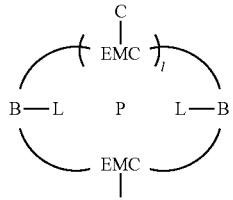
(XIX)

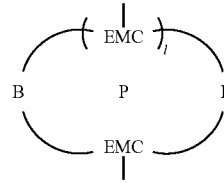
(XX)

Modified proteins containing a linker are a part of the present invention. Within this embodiment, it is preferred if the linker is a prodrug linker or a traceless linker, more preferably traceless prodrug linker.

After the cleavage of the linker, a MPIC results in which the protein is not connected to the macrocyclic structure via a linker (a chemical bond), but the protein is held within the cavity defined by the macrocyclic structure. The resulting MPICs are an object of the present invention. It depends on the release kinetics of the protein if the MPIC having no bond between the protein and the macrocyclic structure can be isolated as such.

The EPICs, MPICs and the DPICs of the present invention are synthesized from the protein and the EOC, macrocyclic structure and dendrimer, respectively, by a combination of solid-phase and solution synthesis methods known to the person skilled in the art.

The host molecule may be equipped with the linker moiety and be attached to the protein in one single reaction step (convergent synthesis). Alternatively, the linker-protein conjugate may be reacted with the branching unit B contained in the EOC, dendrimer or macrocyclic backbone structure. In another, divergent manifestation of the process, protein-linker-branching unit conjugate is reacted with presynthesized EOCs, macrocyclic structures or dendrimers. In an even more divergent approach, the dendrimers, macrocyclic structures or EOCs are assembled in a stepwise fashion in an extension of the central protein-linker-branching unit structure.

Efficient encapsulation is demonstrated by antibody binding studies. Antibodies against therapeutic proteins are high-affinity, high-selectivity probes. Steric shielding of the protein prevents access of the antibodies to the epitopes for molecular recognition. Antibody binding may be conveniently and reliably measured by methods known to the person skilled in the art, preferably immunoprecipitation or, as exemplified here, by label-free surface plasmon resonance scanning. In a study involving various insulin derivatives including insulins conjugated to different PEG reagents, and three monoclonal anti-insulins, complete prevention of antibody recognition was only achieved if insulin was complexed with a macrocyclic structure according to the present invention. In order to eliminate any bias by insulin release, non-cleavable covalent PEG or EOC conjugates were employed respectively.

The resulting EOC self-organizes into a biomolecule-containing void by conformationally folding around the protein. This arrangement may be driven by sterical constraints or by chemical reactions or both.

Eventually, the linker is cleaved, and a host-guest complex is obtained. Linker cleavage may be performed in vitro to generate a non-covalent complex. Alternatively, linker cleavage may occur in a prodrug approach in vivo after administration. Dissociation kinetics of the complex may be governed by linker hydrolysis or protein effusion through the molecular matrix of the EOC, dendrimer, or macrocyclic structure, or a combination of both.

In the presence of the protein, the complex is characterized by a well-defined cavity-forming chemical structure and precise stoichiometry. After protein release, the host molecule may adopt various conformations due to its structural flexibility, for which reason protein release is essentially irreversible.

The formulae (XXI) to (XXIV) below show DPICs and MPICs wherein the bond between the linker and the protein has been cleaved; in two cases, traces of the linker remain at the EOC, dendrimer or macrocyclic structure, and in two cases the linker has totally been removed.

(XXI)

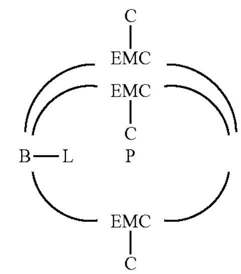

(XXII)

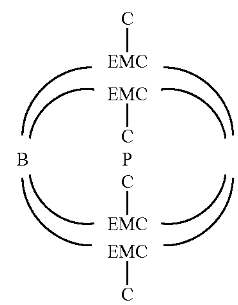

(XXIII)

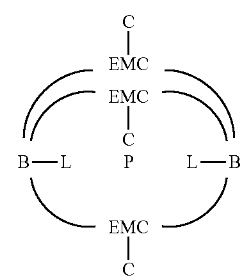

(XXIV)

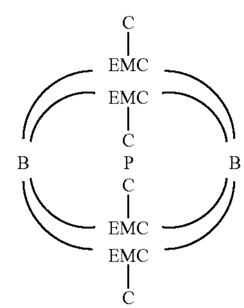

The present invention also relates to method for selectively delivering a protein to a target, which method comprises providing an encapsulated protein;

bringing the encapsulated protein into contact with a body liquid containing the target.

The encapsulated protein can be formulated into a drug, optionally together with one or more pharmaceutically acceptable carriers. The drug can contain one or more encapsulated protein types.

Drug containing at least one encapsulated protein according to the present invention and optionally one or more pharmaceutically acceptable carriers are also an object of the present invention The present invention will now be illustrated by the following, non-limiting examples.

EXAMPLES

Materials and Methods

Materials

Figure 1:
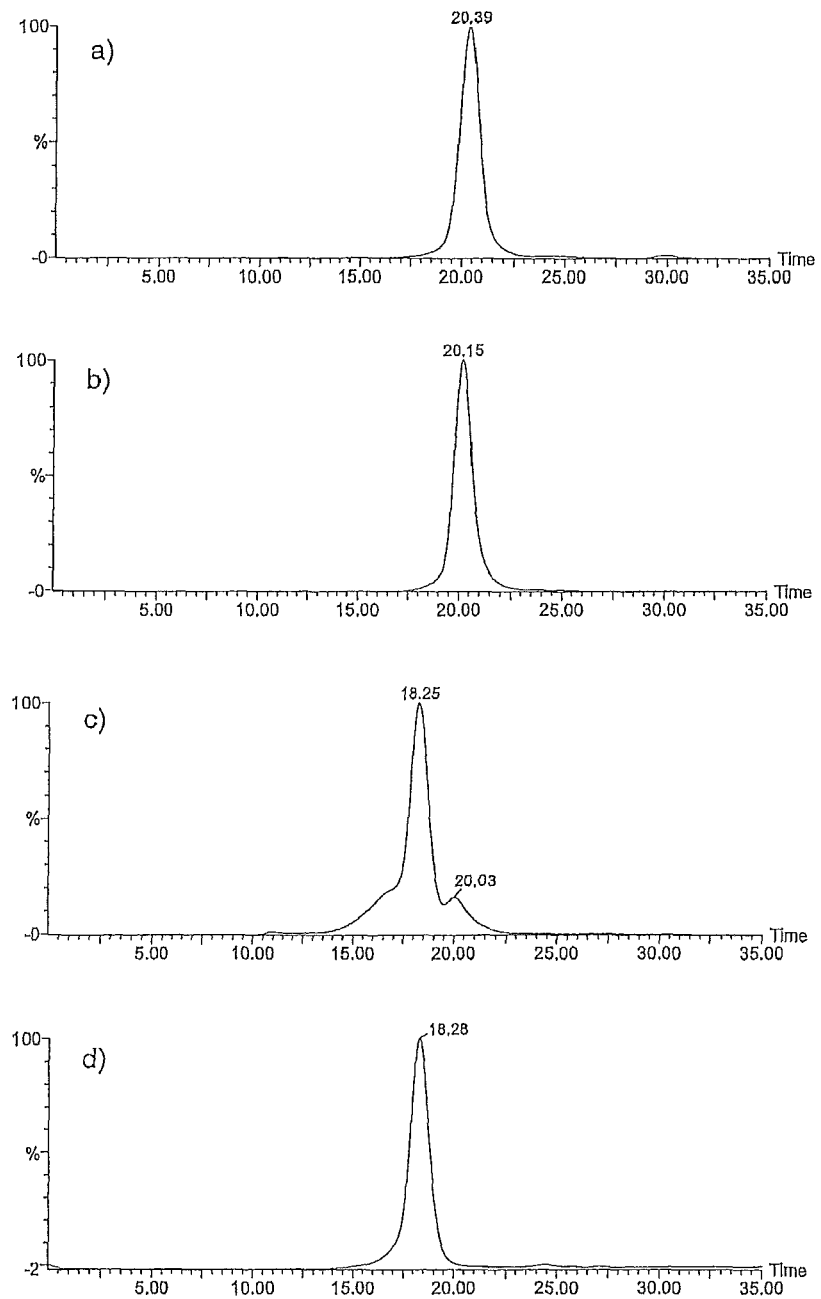
FIG. 1: Size exclusion chromatograms of a) native Hb, b) 39, c) reaction mixture 40, and d) purified covalent Hemoglobin MPIC 40. UV signals were recorded at 280 nm.

Fmoc-amino acids, resins and TBTU were purchased from Novabiochem and are named according to the catalogue. Fmoc-Ado-OH was obtained from Neosystem (France) and Fmoc-PP—OH from Polypure (Norway). All additional chemicals were purchased from Sigma Aldrich. Human insulin was from ICN Biomedicals (USA). Maleimide-PEG5k, Maleimide-PEG20k and Maleimide-PEG2×20k were obtained from Nektar.

Reaction Medium

Solid phase synthesis was performed on TentaGel TGR or Sieber amide resin with a loading of 0.2 mmol/g or 0.5 mmol/g, respectively. Syringes equipped with polypropylene fits were used as reaction vessels.

Standard Coupling Cycle for Fmoc-Protected Amino Acids

For Fmoc protecting-group removal, resin was repeatedly (three times, 4 min each) agitated with 2/2/96 (v/v/v) piperidine/DBU/DMF and repeatedly (six times) washed with DMF. Coupling of Fmoc-protected amino acids to resin was achieved by agitating the resin with 3 equivalents (eq) of Fmoc-amino acid, 3 eq TBTU and 6 eq DIEA in DMF for 60 min. Finally, the resin was repeatedly (five times) washed with DMF.

Standard Cleavage Protocol for TentaGel TGR Resin

Upon completed synthesis, resin was washed with DCM, dried in vacuo and treated with 95/5 (v/v) TFA/TES. After evaporation, compounds were purified by preparative RP-HPLC (Waters 600).

Analysis

Mass spectrometry (MS) was performed on a waters ZQ 4000 ESI instrument and spectra were, if necessary, interpreted by waters software MaxEnt. Size exclusion chromatography were performed using a Waters 600 systems equipped with either a Superdex 75 or Superdex 200 column (Pharmacia) or manually using a PD10 column (Pharmacia).

I—Synthesis of Bifunctional Linkers

I-1) Synthesis of Linker 1

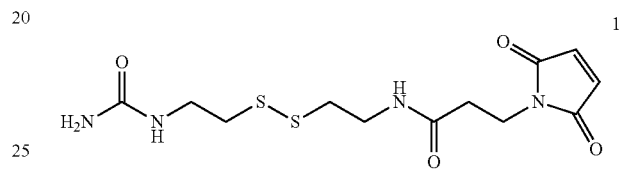

0.7 g TentaGel TGR resin was soaked in THF and incubated for 60 min with a solution of 4 ml of 0.5 M chloroformic acid-4-nitrophenyl ester and 0.5 M DIEA in THF, washed with THF and dried. 4 ml of a suspension of 0.3 M cystamine-dihydrochloride and 0.7 M DIEA in DMSO were added to the resin and agitated for min. Resin was washed with DMSO and DMF, and 3 eq maleimidopropionic acid and 3 eq DIC in DMF were added and agitated for 60 min.

After washing the resin with DMF and DCM, compound 1 was cleaved from the resin and purified by RP-HPLC.

MS (MW calculated) 1: 346 g/mol (346.4 g/mol)

I-2) Synthesis of Linker 2

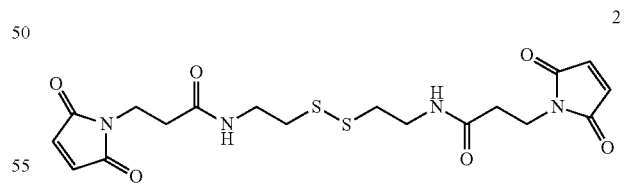

Cystamine-dihydrochloride was suspended in 1/1 (v/v) DMSO/DMF and mixed with 2 eq maleimidopropionic acid, 2 eq DIC and 2 eq DIEA. The suspension was agitated for 2 h at room temperature (RT) and after acidification with formic acid, compound 2 was purified by RP-HPLC.

MS (MW calculated) 2: 454 g/mol (454.5 g/mol)

I-3) Synthesis of Linker 5

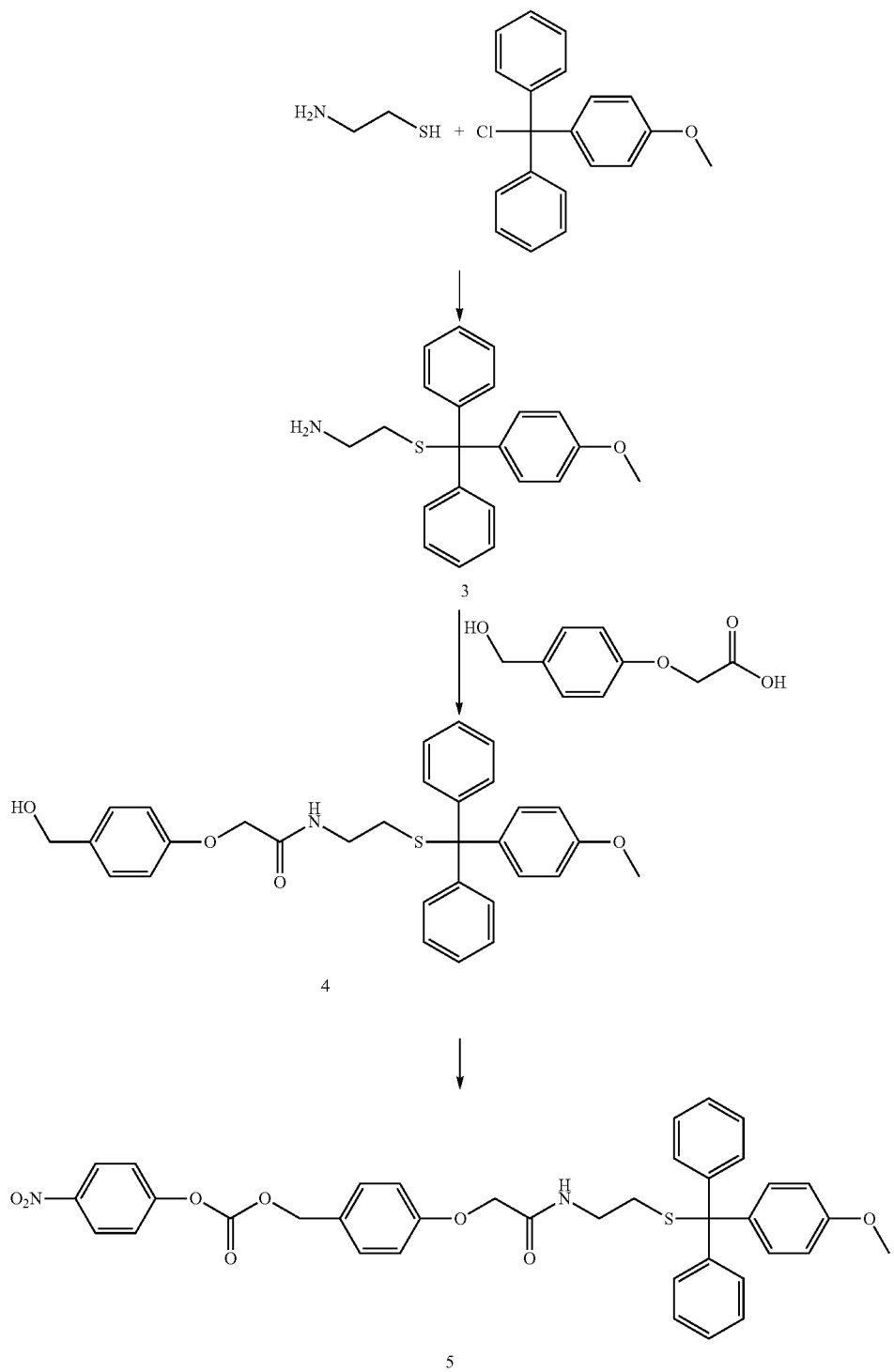

Cysteamine hydrochloride was dissolved in TFA and 0.5 eq Mmt-chloride were added. After 30 min, TFA was removed under nitrogen flow and the residue was taken up in pyridine. After adding a solution of 0.2 M $Na_2CO_3$, product was extracted with ether and dried over $Na_2SO_4$. Following filtration, solvents were removed using a rotary evaporator and compound 3 was obtained as a highly viscous oil.

3 was reacted with 4-hydroxymethyl-phenoxyacetic acid (HPMA) and 1 eq HOBT/DIC for 30 min. After purification by RP-HPLC, compound 4 was neutralized by DIEA and lyophilized.

4 was reacted with 5 eq chloroformic acid-4-nitrophenyl ester and 10 eq DIEA in dioxane for 2 h. Subsequent purification by RP-HPLC gave product 5.

MS [MNa]⁺ (MW+Na calculated) 5: 700 g/mol (701 g/mol)

I-4) Synthesis of Linker 6

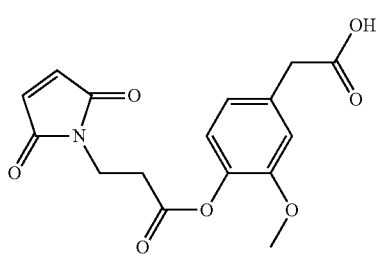

6

300 mg of 4-hydroxy-3-methoxy-phenylacetic acid and 570 μl DIEA were dissolved in 5 ml DCM and added to 0.5 g 2-chlorotrityl-chloride resin (1.5 mmol/g). The suspension was agitated for 1 h at RT and resin was washed with DCM. Resin was resuspended in a solution of 190 mg 3-maleimidopropionic acid, 333 mg MSNT and 73 μl N-methyl imidazole in 3 ml DCM and agitated for 1 h. After washing of the resin with DCM, cleavage was performed by agitation of the resin for 30 min in 10 ml 4/1 (v/v) DCM/TFA. Solvent was removed under nitrogen flow and compound 6 was purified by RP-HPLC.

MS [MNa]⁺ (MW+Na calculated): 356 g/mol (356 g/mol)

I-5) Synthesis of linker 7

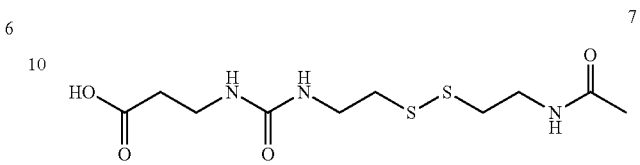

7

512 mg Fmoc-3-aminopropionic acid and 570 μl DIEA were dissolved in 5 ml DCM and added to 0.5 g 2-chlorotrityl-chloride resin (1.5 mmol/g). The suspension was agitated for 1 h at RT and resin was washed with DCM. After Fmoc-removal with 96/2/2 (v/v/v) DMF/DBU/piperidine and washing of the resin with THF, 4 ml of a solution of 0.5 M chloroformic acid-4-nitrophenyl ester and 0.5 M DIEA in THF were incubated with the resin for 30 min Resin was washed with THF and DMF. Subsequently, resin was agitated for 15 min in a solution of 2/1/1 (v/v/v) DMF/acetic anhydride/pyridine. After washing the resin with DMF and DCM, compound 7 was cleaved by agitation for 30 min in 10 ml of 4/1 (v/v) DCM/TFA. After evaporation of solvent under nitrogen flow, product 7 was purified by RP-HPLC.

MS (MW calculated): 309 g/mol (309 g/mol)

I-6) Synthesis of Linker 11

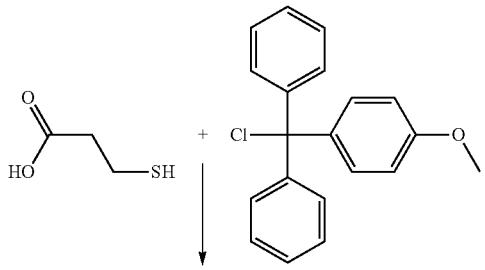

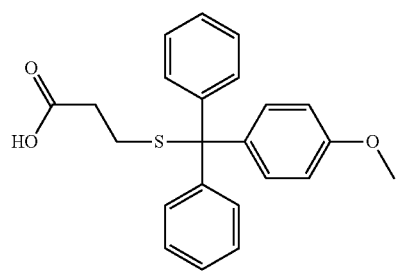

8

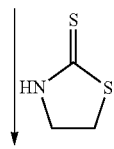

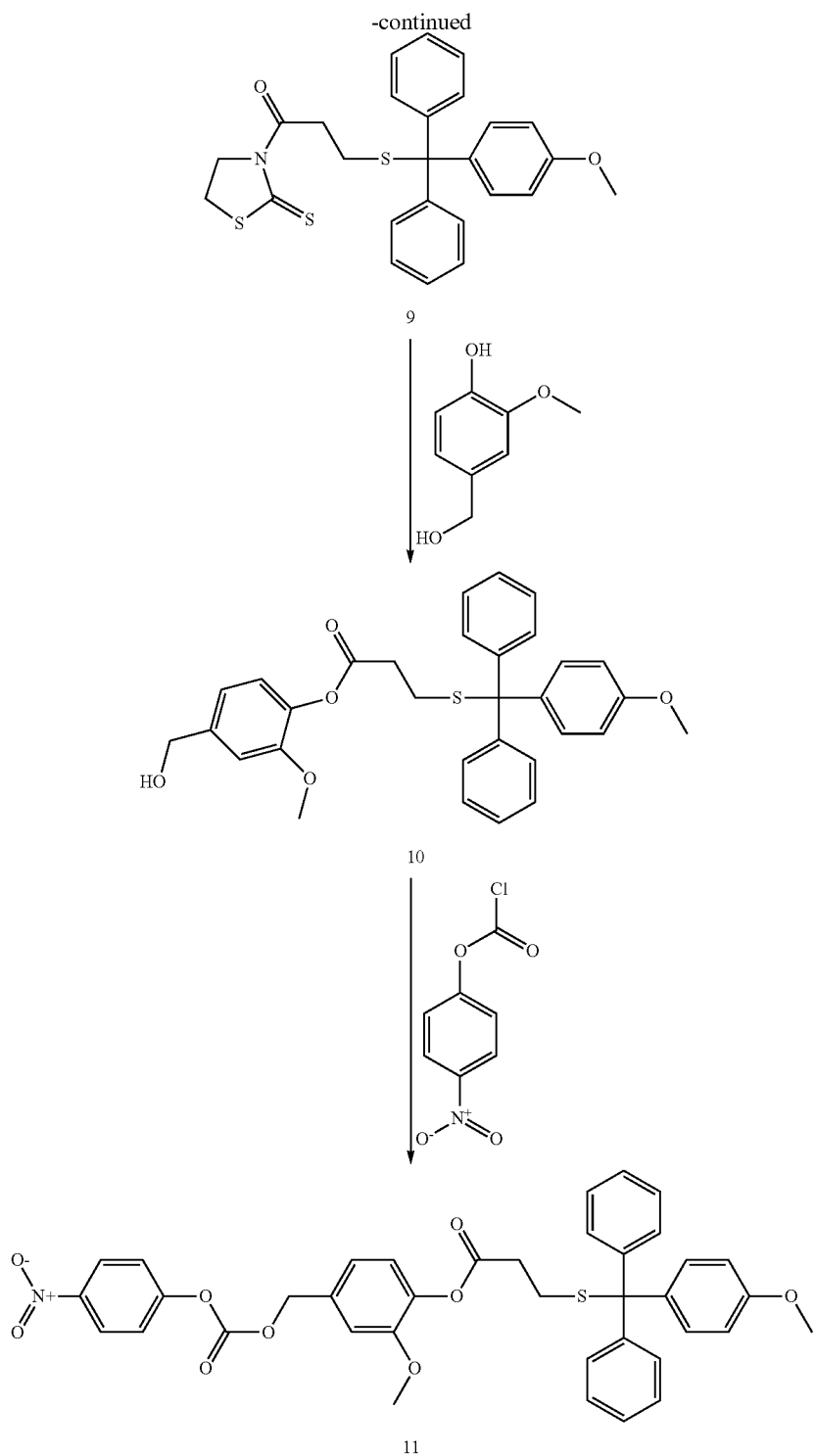

Mmt-chloride (1 eq) and mercaptopropionic acid (1.1 eq) were taken up in TFA and incubated for 30 min. TFA was removed under nitrogen flow. The product was dissolved in pyridine, diluted in water, acidified by acetic acid and extracted in ether. The ether phase was separated and dried over $Na_2SO_4$. Solvent was removed and product 8 was purified by RP-HPLC.

Compound 8 and DMAP (2.5 eq) were dissolved in dry DCM and 2 eq of EDC HCl were added at 0° C. The solution was stirred for 14 hat RT and washed with sodium acetate buffer (0.25 M, pH 4.5). The organic phase was dried over $Na_2SO_4$, concentrated and compound 9 was purified by silica gel column chromatography using heptane/acetic acid ester (1/1) as mobile phase.

MS (MW calculated) 9: 479 g/mol (479.7 g/mol)

Compound 9,4-hydroxy-3-methoxy benzylalcohol (7 eq) and DMAP (7 eq) were refluxed in DCM for 2 h under nitrogen atmosphere. After neutralization with acetic acid, the solution was concentrated and compound 10 was purified by RP-HPLC:

MS [M+Na]$^+$ (MW+Na calculated) 10:537 g/mol (537.6 g/mol)

Compound 10, chloroformic acid-4-nitrophenyl ester (10 eq), and DI FA (20 eq) were stirred in dry dioxane for 3 h at 40° C. under nitrogen atmosphere. After addition of acetic acid (25 eq) the mixture was concentrated and compound 11 purified by RP-HPLC:

MS [M+Na]$^+$ (MW+Na calculated) 11: 702 g/mol (702.7 g/mol)

II—Synthesis of Bifunctional Macrocyclic Structures

II-1) Synthesis of bis-maleimido-macrocyclic Structure 18

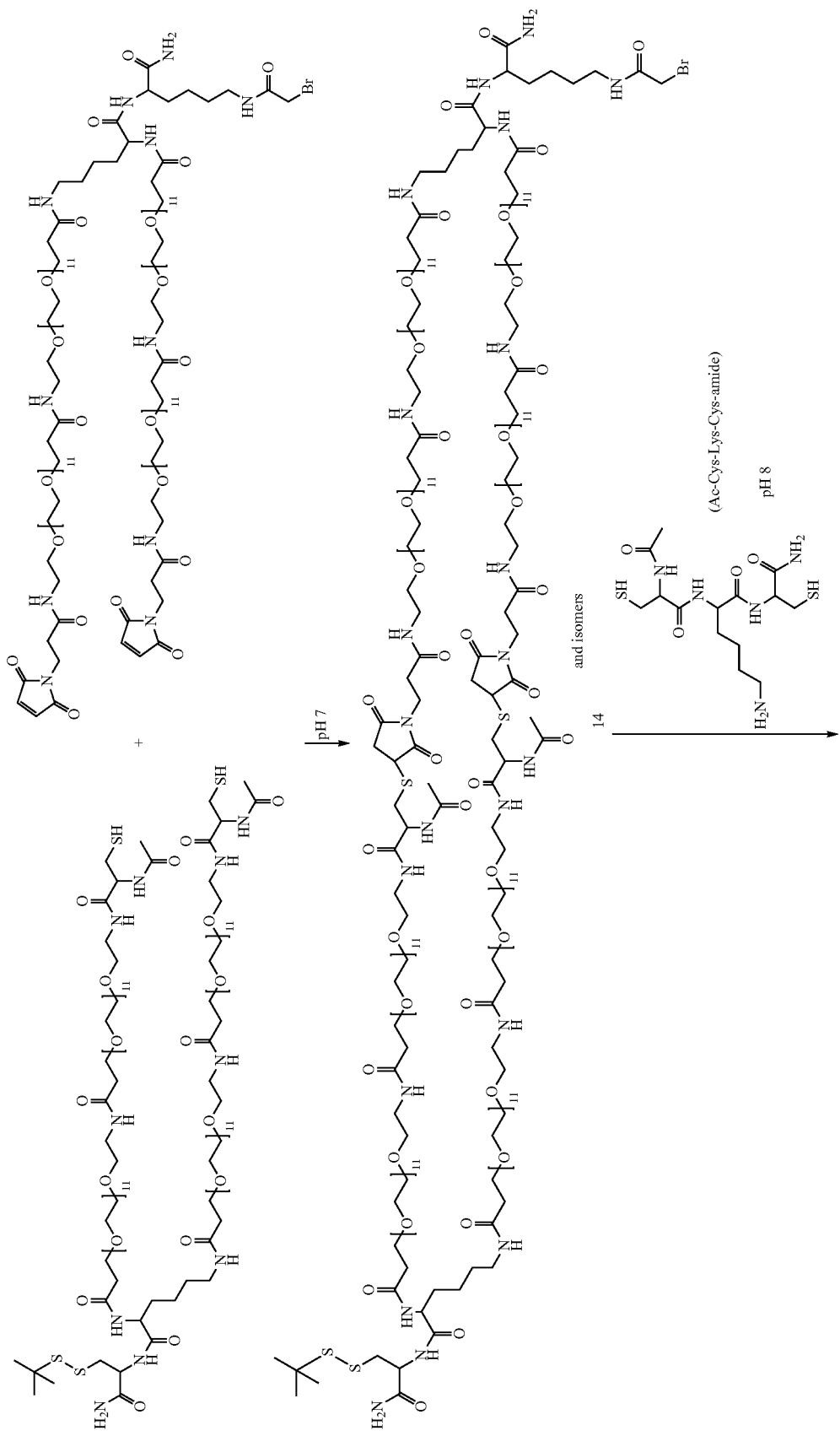

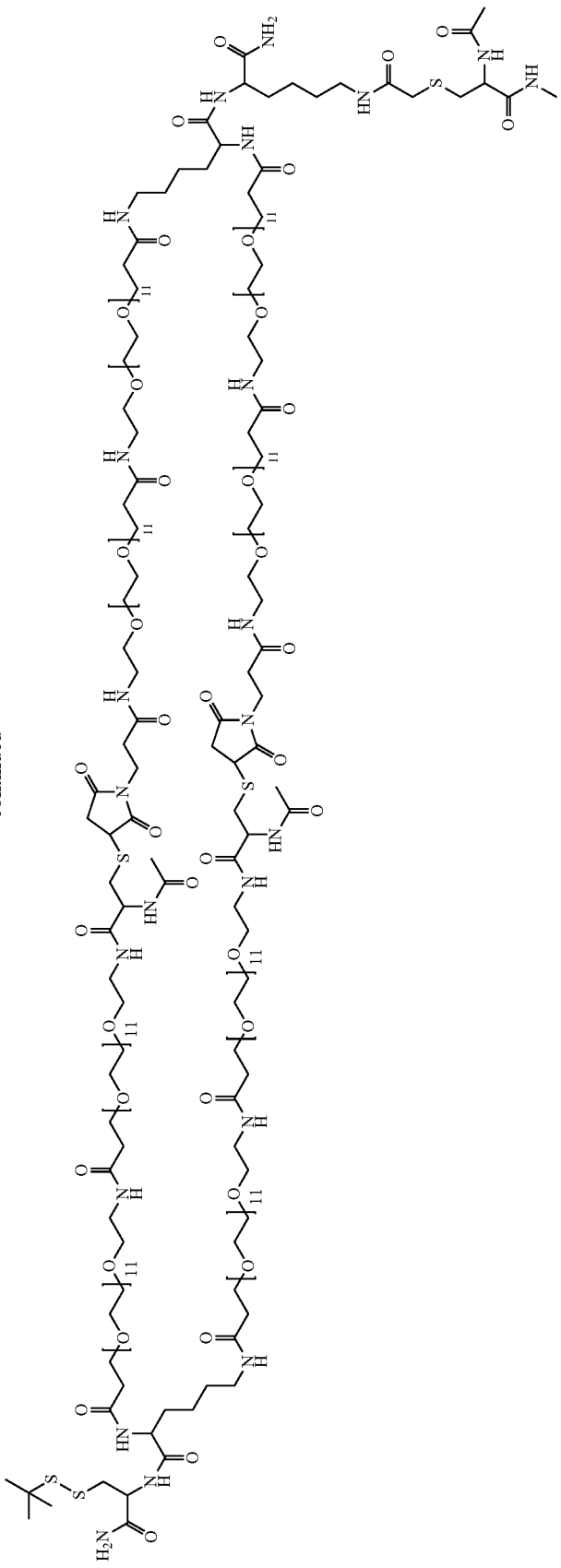

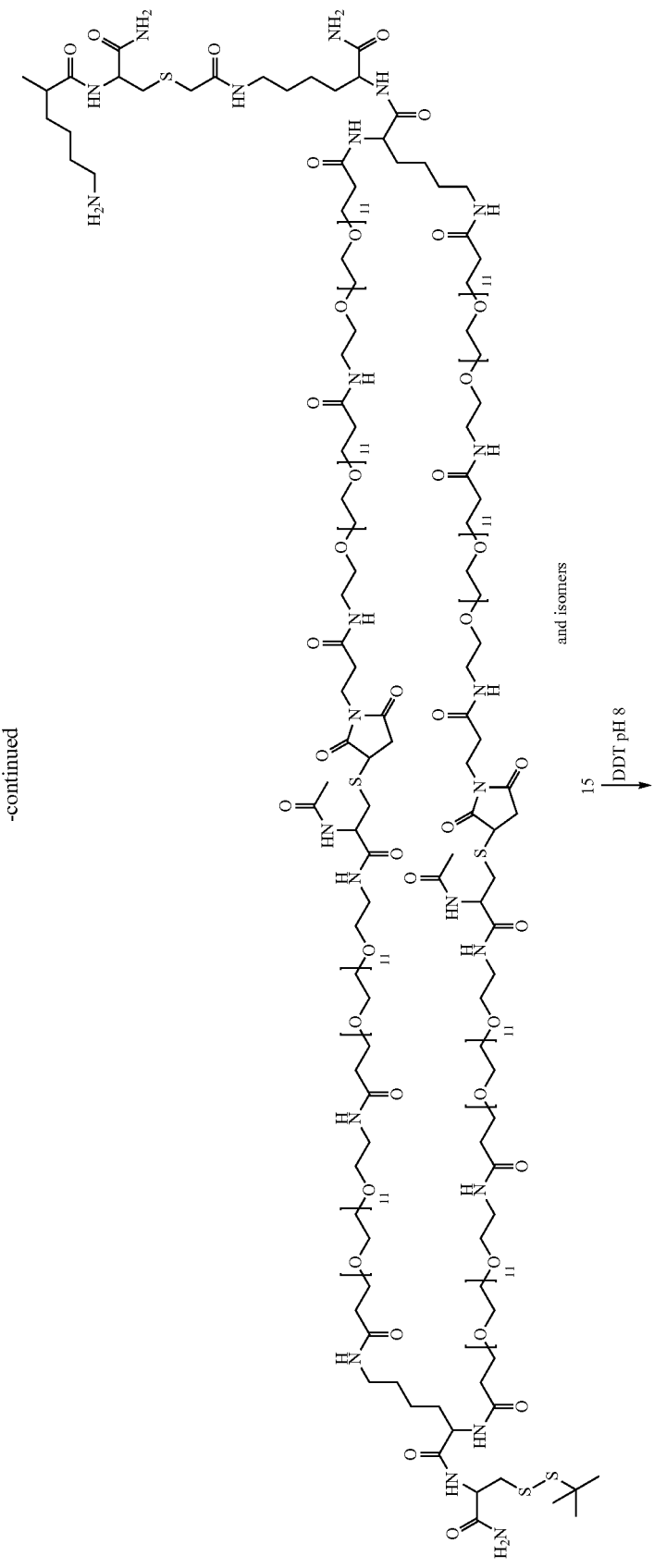

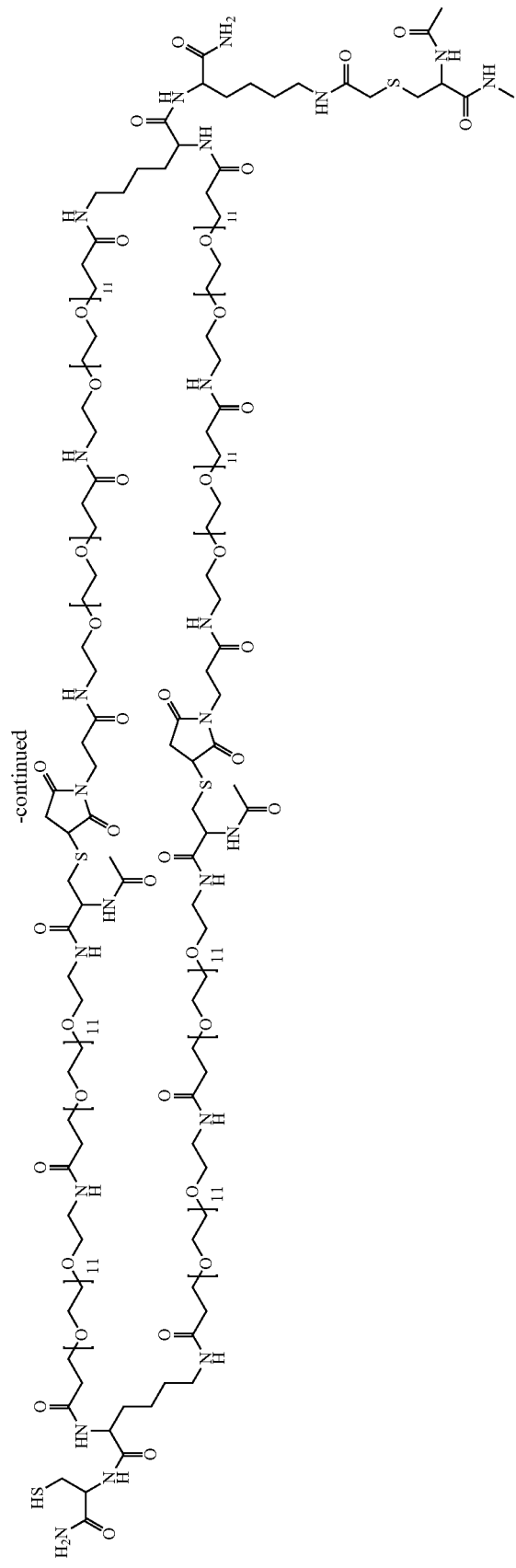

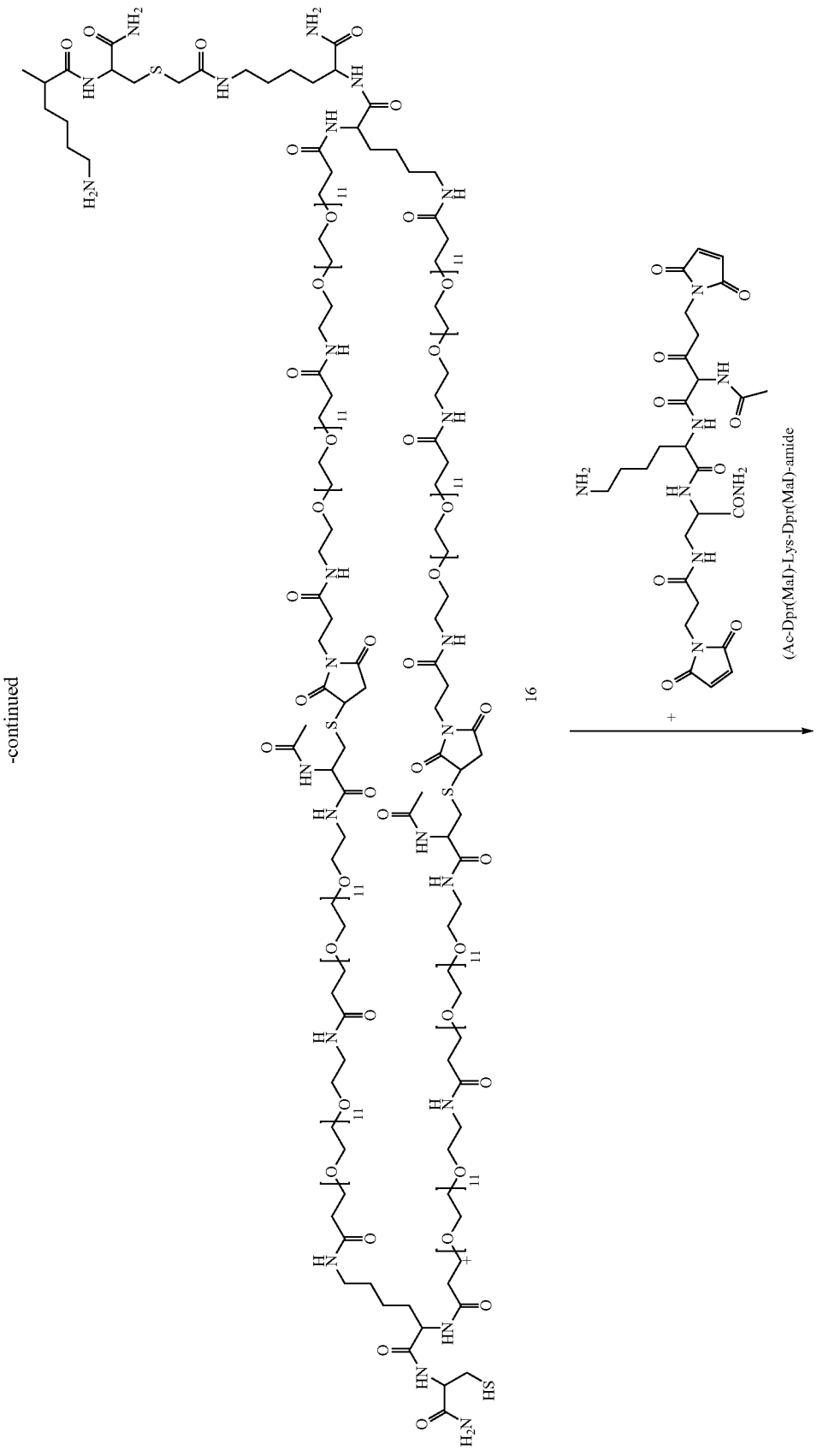

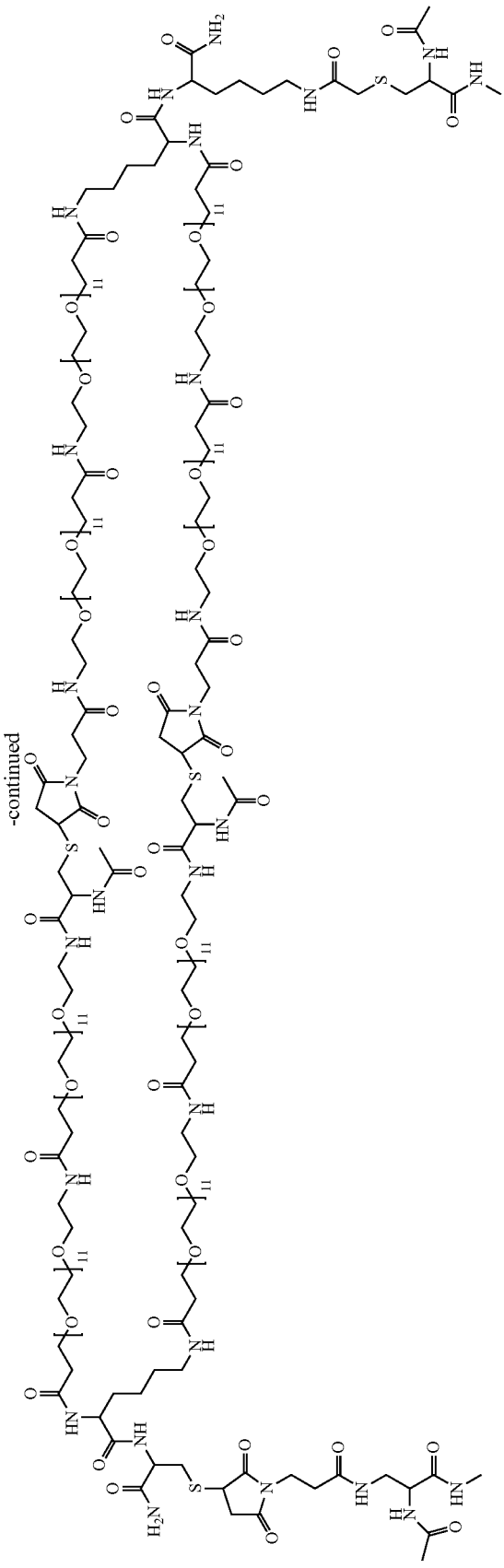

-continued
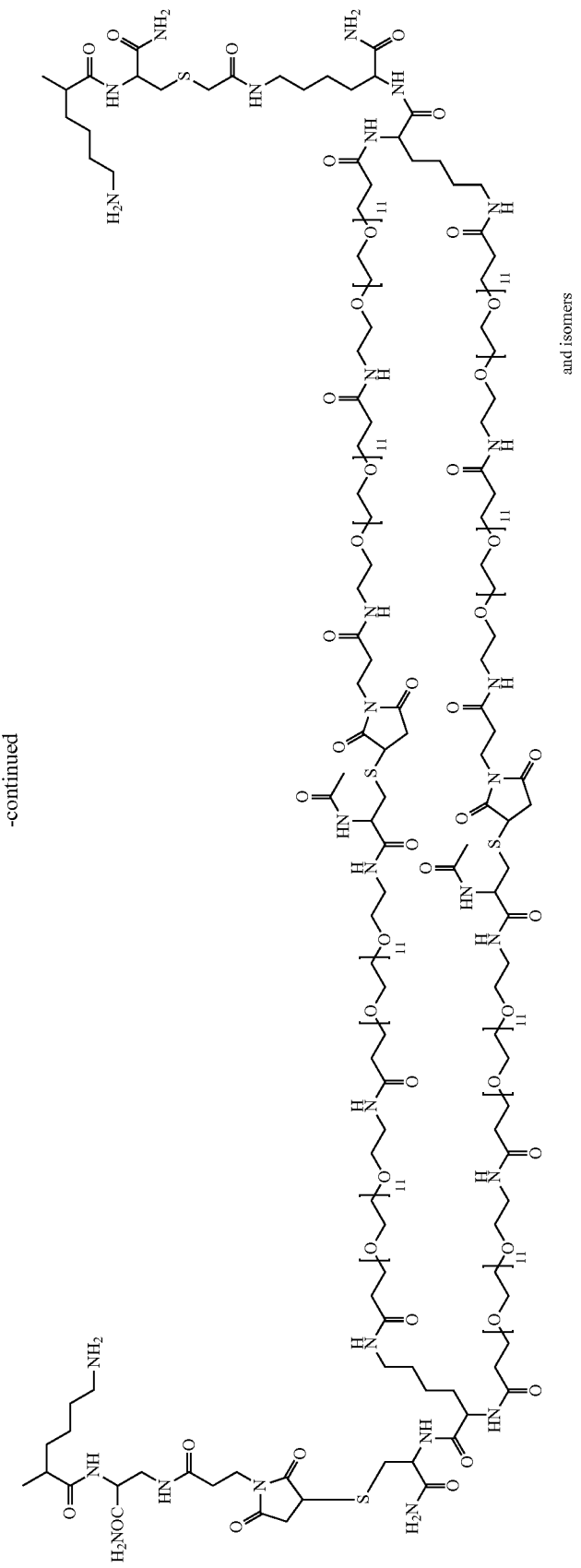
and isomers

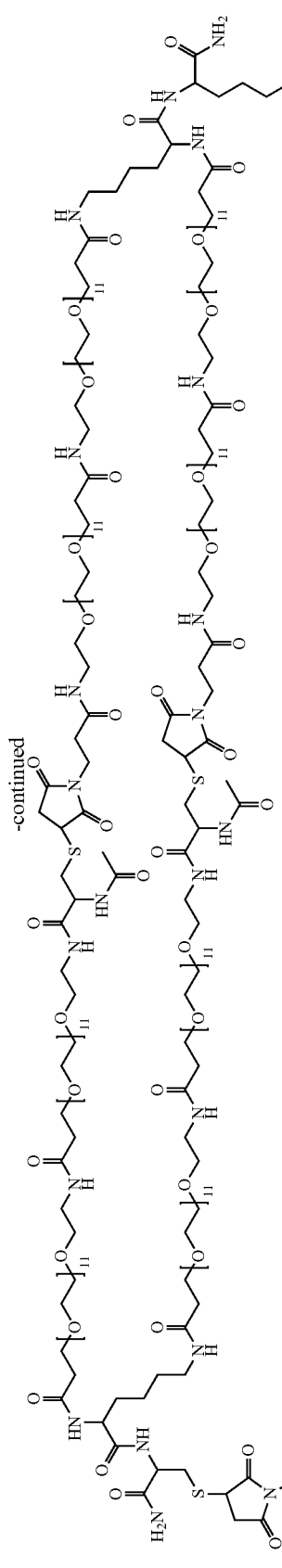
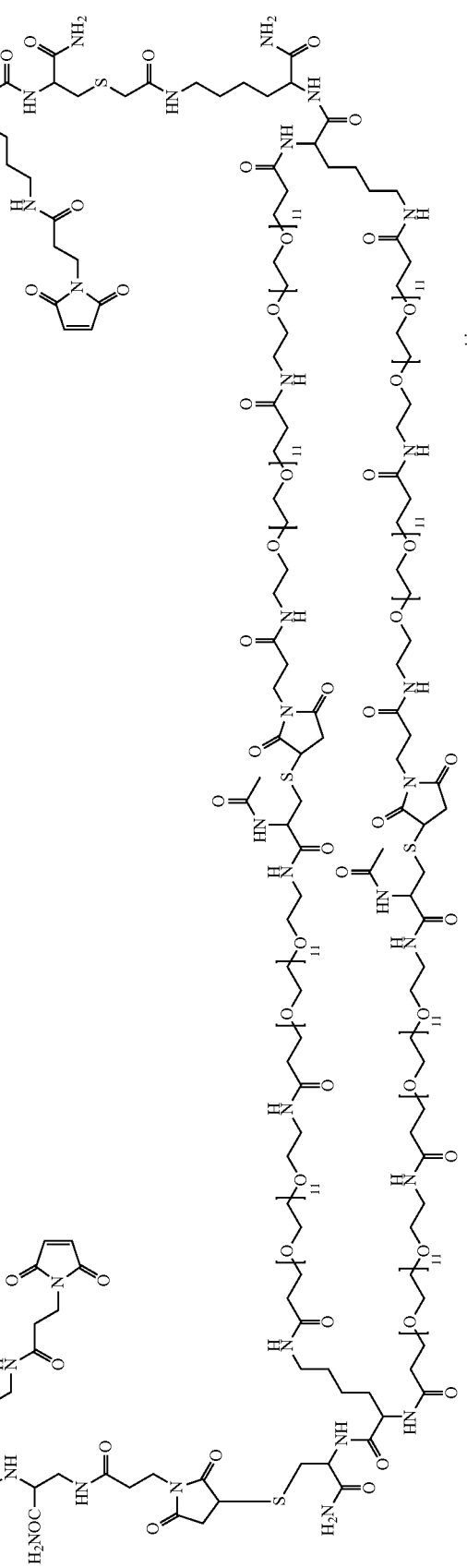
and isomers
18

Employing the standard protocol for solid-phase synthesis, the amino acids Fmoc-Cys(S-tBu)-OH, Fmoc-Lys(Fmoc)-OH, two units of Fmoc-PP—OH and Fmoc-Cys(Trt)-OH were coupled to TGR resin. After final Fmoc-removal, resin was treated with 2/1/1 (v/v/v) DMF/acetic anhydride/pyridine for 15 min. Compound 12 was cleaved from the resin and purified by RP-HPLC.

MS (MW calculated) 12:3024.8 g/mol (3025.8 g/mol)

Employing the standard protocol for solid-phase synthesis, the amino acids Fmoc-Lys(Mtt)-OH, Fmoc-Lys(Fmoc) and two units of Fmoc-PP—OH were coupled to TGR resin. After final Fmoc removal, the resin was treated for 30 min with 5 eq maleimidopropionic acid and 5 eq DIC in DMF. Removal of the Mtt-protecting group was achieved by repeated washing of the resin with 99/1 (v/v) DCM/TFA until the solution remained colorless. Resin was washed with DCM, 1% DIEA in DMF (briefly) and DMF. Subsequently, resin was incubated for 25 min with a solution of 0.5 M bromoacetic acid and 0.5 M DIC in DMF. After cleavage, compound 13 was purified by RP-HPLC.

MS (MW calculated) 13:3095.2 g/mol (3095.5 g/mol)

12 and 13 were mixed at an equimolar ratio and concentration was adjusted to 35 µM by addition of 0.1% aqueous TFA. The pH of the solution was adjusted to 7.5 with 0.1 M phosphate buffer (pH 7.5). After 20 min the pH of the mixture was brought to 2.0 by addition of formic acid, and product 14 was purified by RP-HPLC and lyophilized.

MS (MW calculated) 14:6120 g/mol (6121.1 g/mol).

2 eq 14 were mixed with 1 eq Ac-Cys-Lys-Cys-NH$_2$ (obtained according to the standard protocol for solid phase synthesis) at a concentration of 350 µM and the pH of the solution was adjusted to 8.0 with phosphate buffer. After 90 min the reaction was quenched by acidification with acetic acid, and product 15 was purified by RP-HPLC.

MS (MW calculated) 15: 12472 g/mol (12474.2 g/mol)

S-tBu protecting groups in 15 were removed by reduction with 100 mM DTT in phosphate buffer (pH 8.0). After 3 h the pH of the solution was adjusted to 2.0, and compound 16 was purified by RP-HPLC.

MS (MW calculated) 16: 12295 g/mol (12297.8 g/mol) 16 was mixed with 1 eq Ac-Dpr(Mal)-Lys-Dpr(Mal)-NH$_2$ (obtained according to the standard protocol for solid phase synthesis using Fmoc-Dpr(ivDde)-OH) and concentrations were adjusted by addition of water to 15 µM. Subsequently, pH was adjusted to 7.5 with 0.1 M phosphate buffer (pH 7.5) and stirred for 20 min. The pH of the solution was brought to 2.0 by formic acid, and compound 17 was purified by RP-HPLC and lyophilized.

MS (MW calculated) 17: 12955 g/mol (12959.5 g/mol)

17 was dissolved in DMF and agitated for 30 min with a solution of 20 eq maleimidopropionic acid, 30 eq DIEA and 20 eq DIC in DMF. Subsequently, the solution was acidified with formic acid, diluted with water and 18 was purified by RP-HPLC and lyophilized.

MS (MW calculated) 18: 13257 g/mol (13261.7 g/mol)

II-2) Synthesis of Bis-Thiol-macrocyclic Structure 19

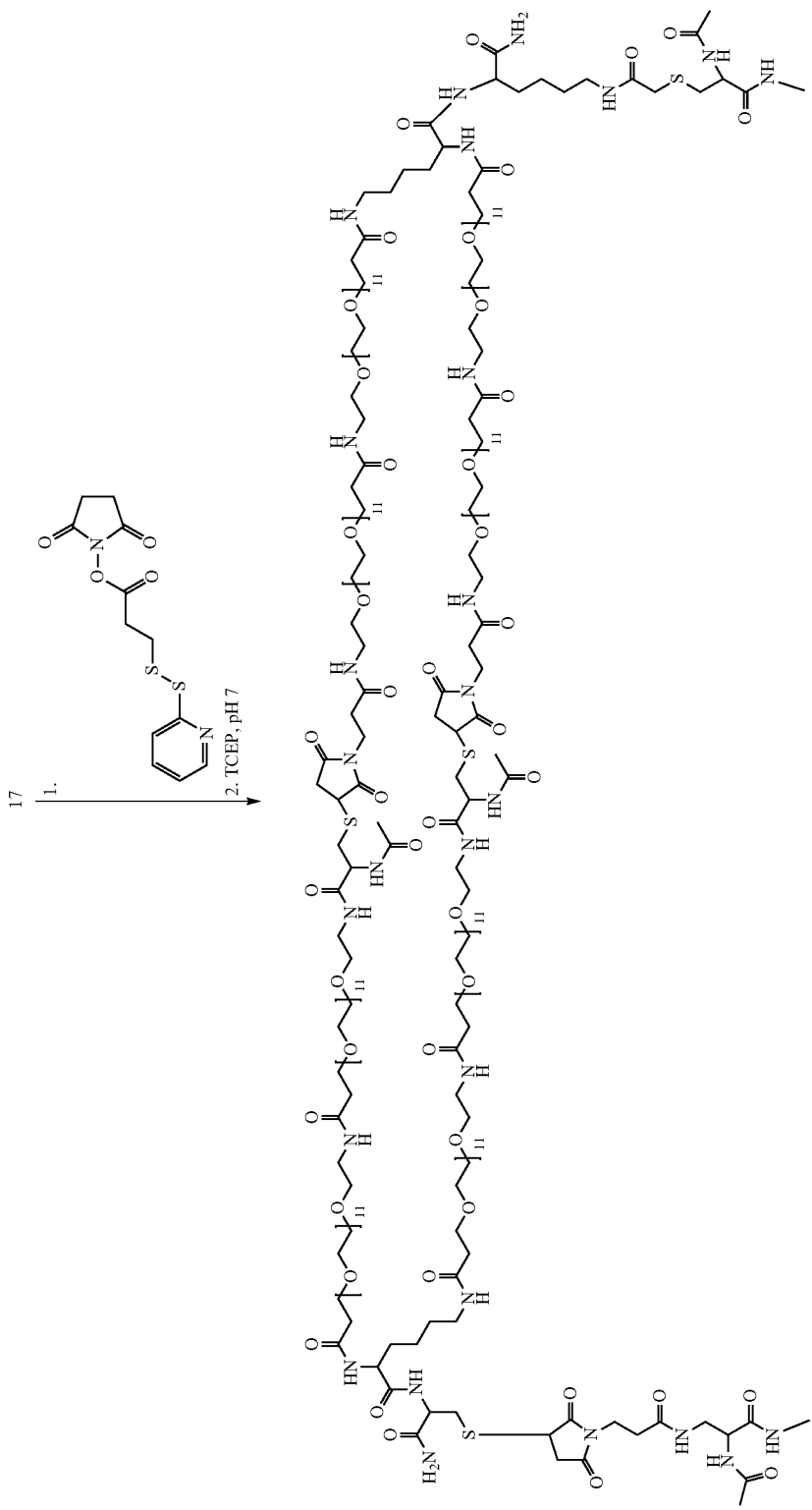

-continued
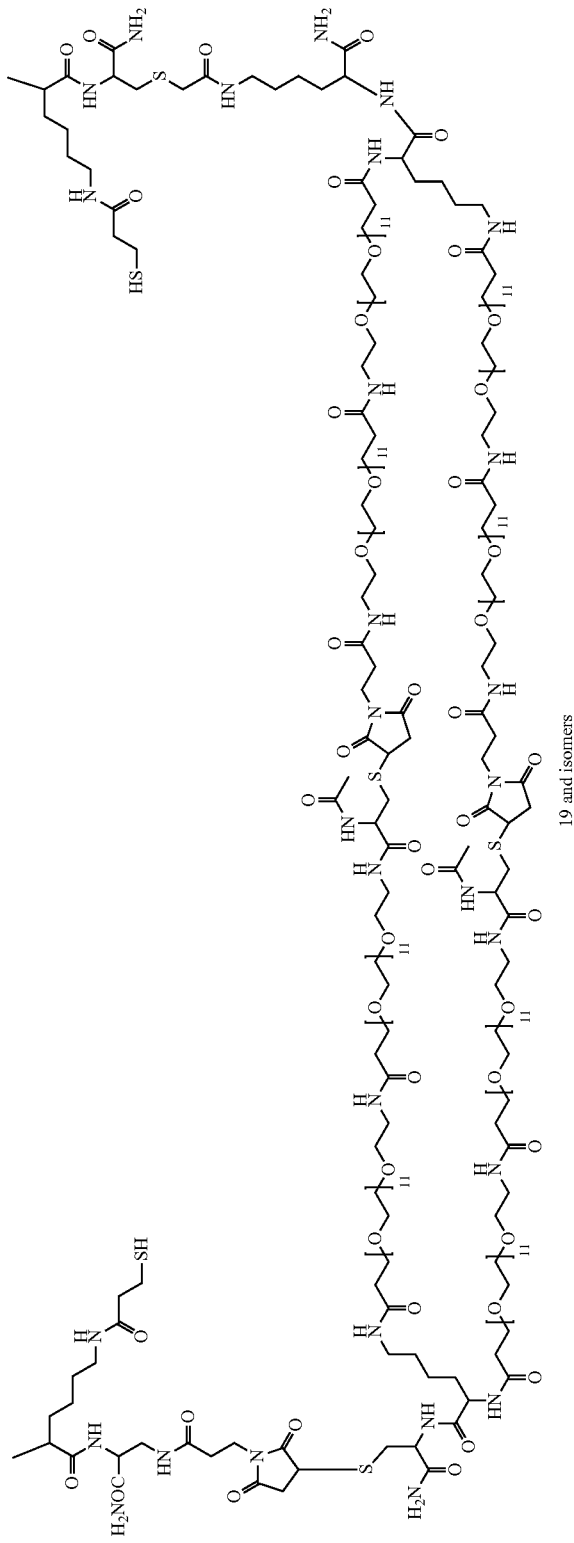
19 and isomers 17 was adjusted to a concentration of 300 μM in 0.1 M phosphate buffer (pH 7.0) and 15 eq SPDP in DMSO were added. The resulting suspension was agitated for 20 min at RT. 10 mM TCEP were added, and the cocktail was agitated for another 20 min at RT. Product 19 was purified by RP-HPLC.

MS (MW calculated) 19: 13132 g/mol (13135.7 g/mol)

II-3) Synthesis of bis-maleimido-macrocyclic Structures 25a and 25b

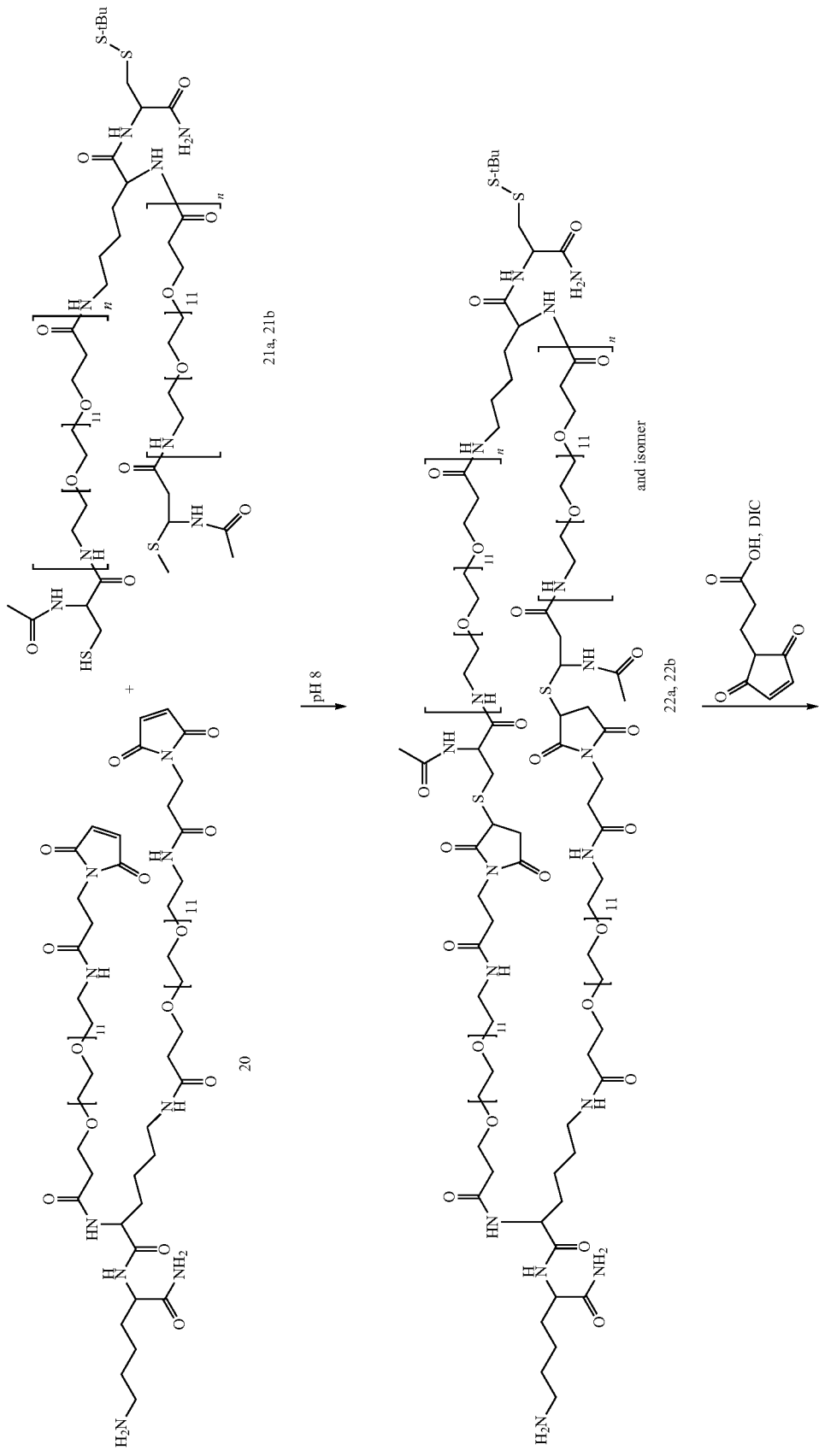

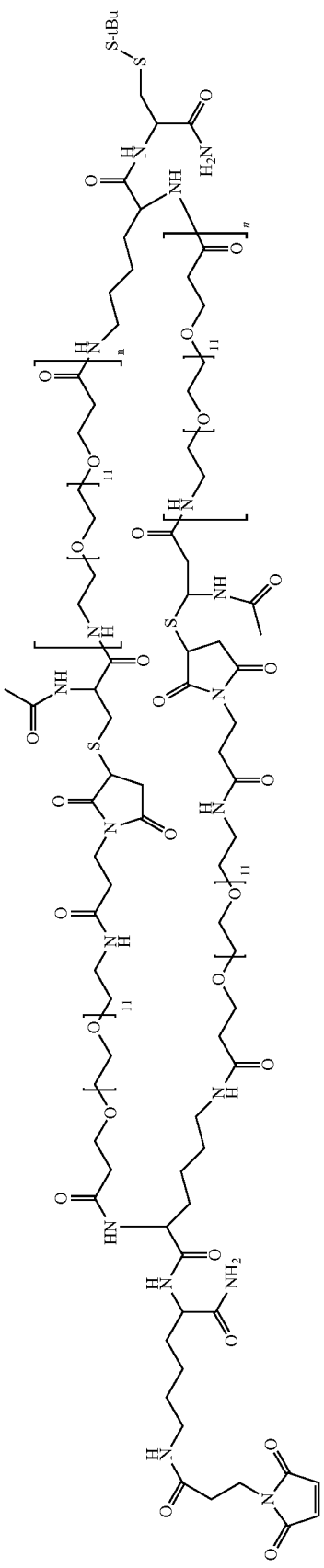
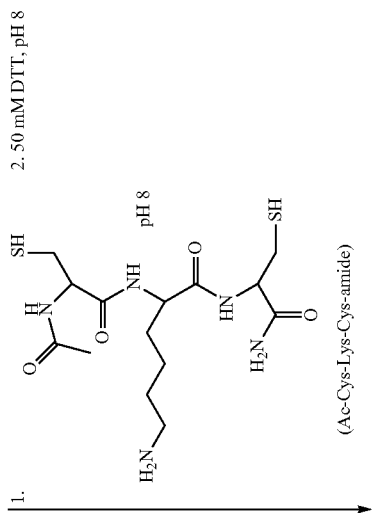

-continued
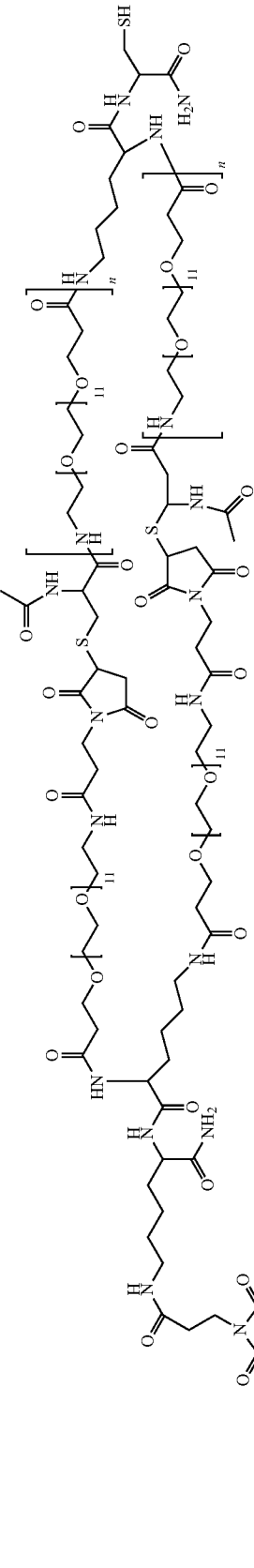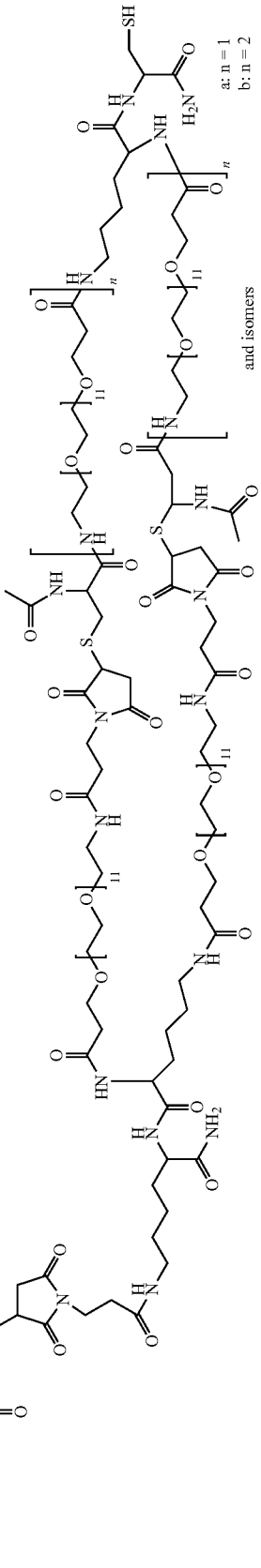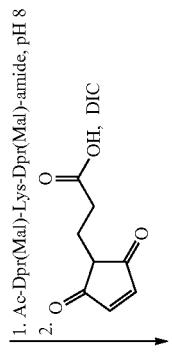
a: n = 1
b: n = 2
and isomers
24a, 24b
1. Ac-Dpr(Mal)-Lys-Dpr(Mal)-amide, pH 8
2. OH, DIC -continued
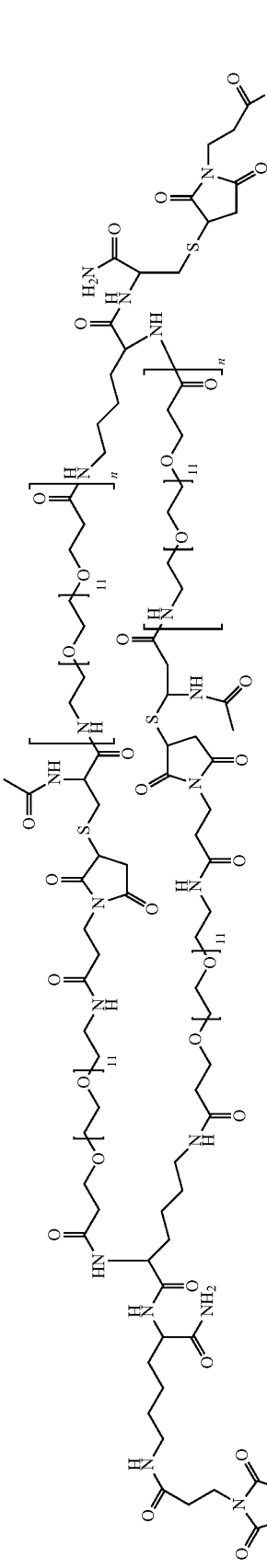
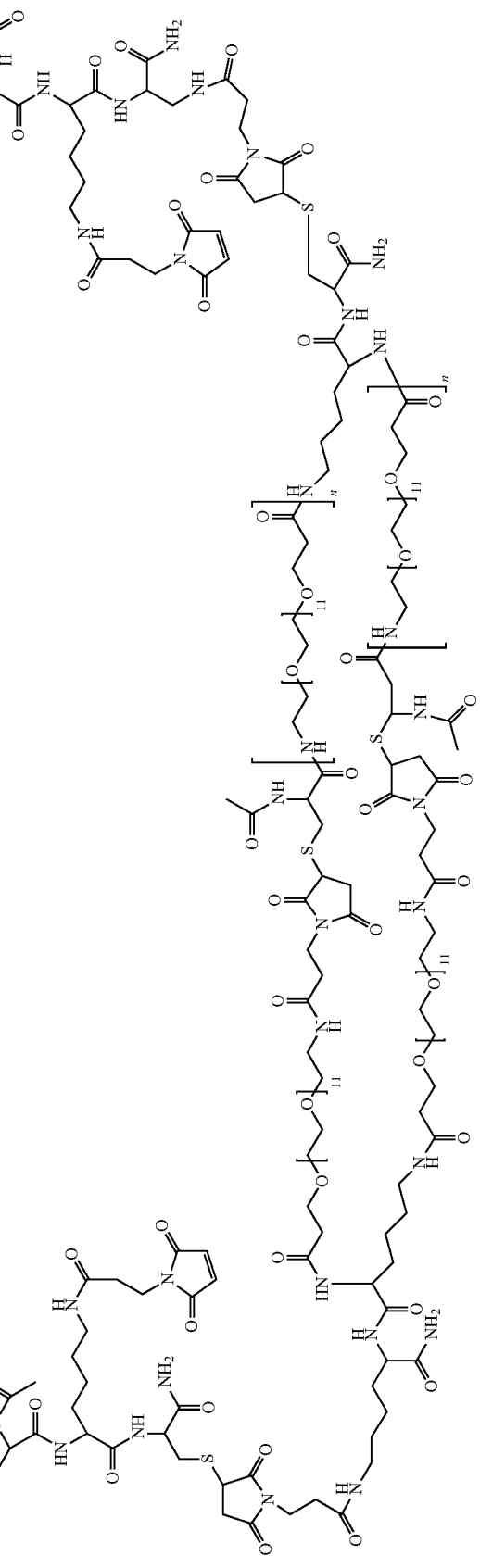
a: n = 1
b: n = 2
and isomers
25a, 25b Fmoc-Lys(Mtt)-OH, Fmoc-Lys(Fmoc)-OH and Fmoc-PP—OH were coupled according to the standard protocol for solid phase synthesis. After Fmoc removal, resin was incubated with 6 eq maleimidopropionic acid and 6 eq DIC for 30 min. Following cleavage from resin, compound 20 was purified by RP-HPLC.

MS (MW calculated) 20:1774 g/mol (1775 g/mol)

Compounds 21a and 21b were obtained by solid phase synthesis according to protocol II-1) for product 12.

MS (MW calculated) 21a: 1825 g/mol (1826 g/mol)
MS (MW calculated) 21b: 3024 g/mol (3026 g/mol)

Reactions of educts 20 and 21a to product 22a, and educts 20 and 21b to product 22b were performed according to protocol II-1) in analogy to the reaction of compounds 12 and 13 to product 14.

MS (MW calculated) 22a: 3600 g/mol (3601 g/mol)
MS (MW calculated) 22b: 4800 g/mol (4801 g/mol)

Compounds 22a or 22b, respectively, were dissolved in DMF and pH was adjusted to 8.0 with DIEA. 6 eq Maleimidopropionic acid and 6 eq DIC were added and mixtures were incubated for 30 min to yield compounds 23a and 23h, respectively. Purification was performed by RP-HPLC.

MS (MW calculated) 23a: 3752 g/mol (3753 g/mol)
MS (MW calculated) 23b: 4950 g/mol (4952 g/mol)

2 eq of compound 23a or 23b respectively were mixed with 1 eq Ac-Cys-Lys-Cys-amide (obtained according to the standard protocol for solid phase synthesis). After adjusting the pH to 8.0 by addition of 0.5 M phosphate buffer (pH 8.0) the solution was agitated for 10 min. The reaction was quenched by addition of 10 eq DTT. After lyophilization the residue was taken up in 1:1 (v/v) acetonitrile/50 mM phosphate buffer (pH 8.0). Removal of the S-tBu protecting group by reduction with 50 mM DTT for 2 h yielded products 24a and 24b, respectively. Purification was by RP-HPLC.

MS (MW calculated) 24a: 7719 g/mol (7722 g/mol)
MS (MW calculated) 24b: 10120 g/mol (10121 g/mol)

Compounds 24a or 24b, respectively, were subjected to two additional reaction steps to yield 25a or 25b, respectively, according to protocol II-1 and in analogy to the reaction of compounds 16 and 17 to product 18.

MS (MW calculated) 25a: 8686 g/mol (8686 g/mol)
MS (MW calculated) 25b: 11085 g/mol (11085 g/mol)

II-4) Synthesis of bis-maleimido-core-macrocyclic Structure 31

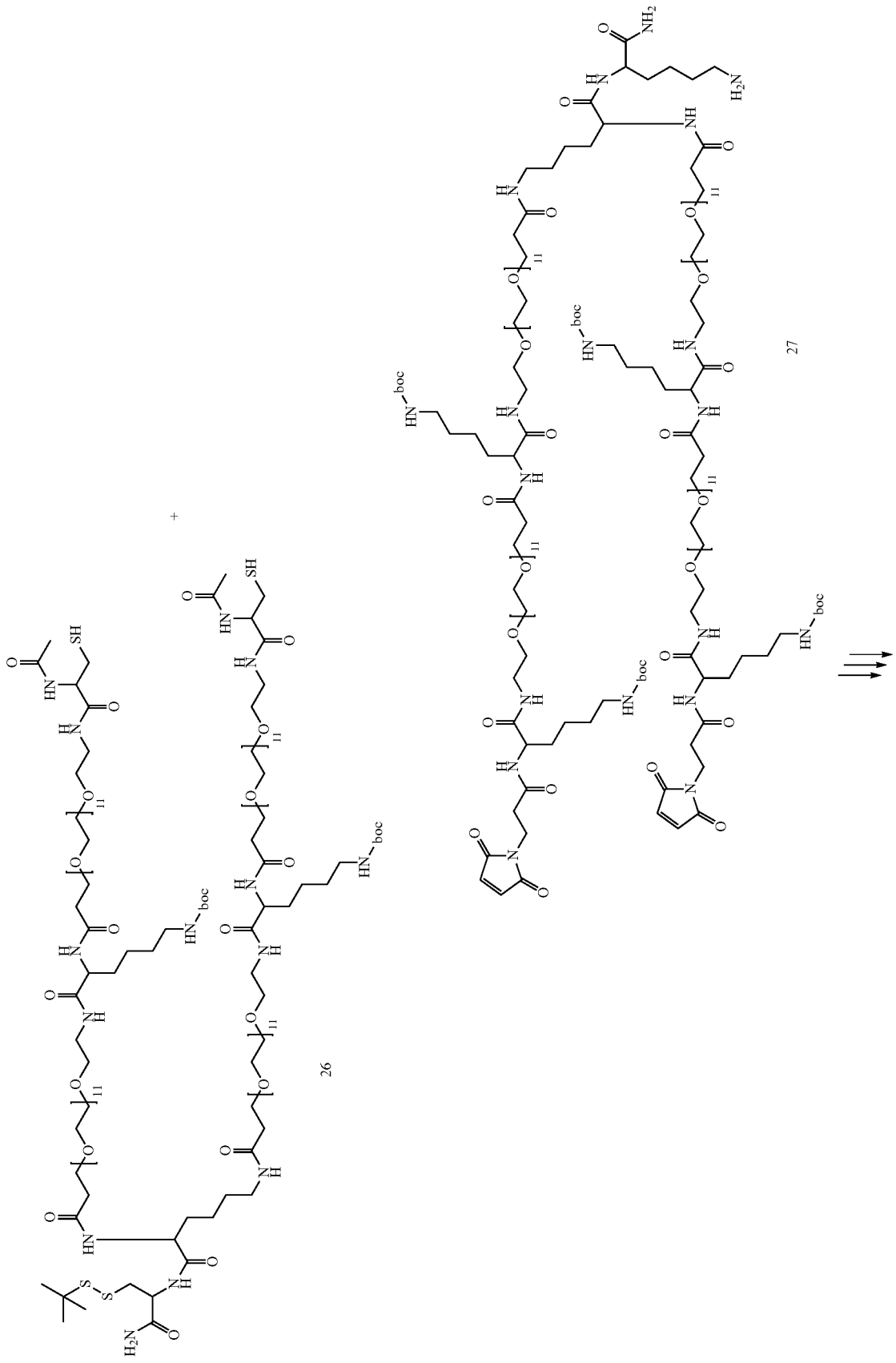

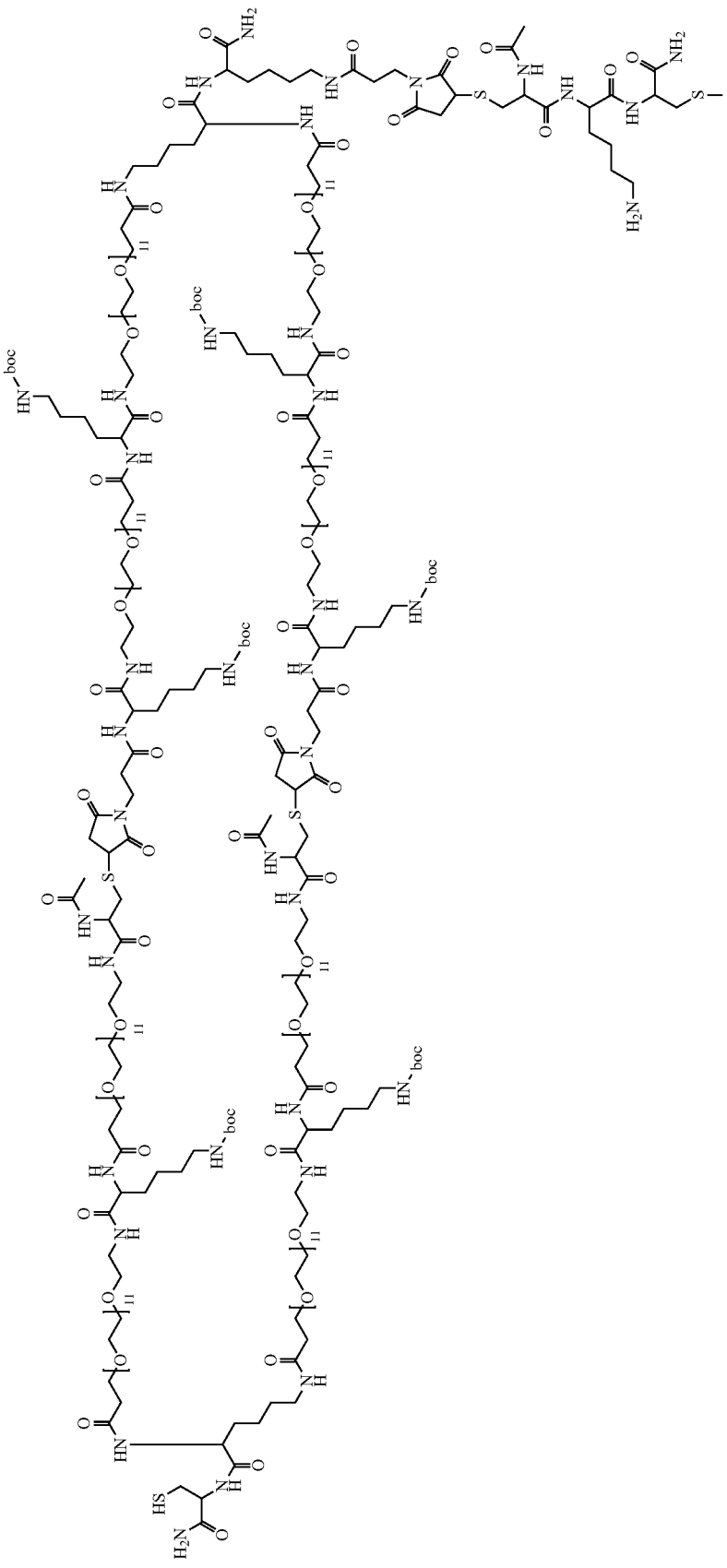

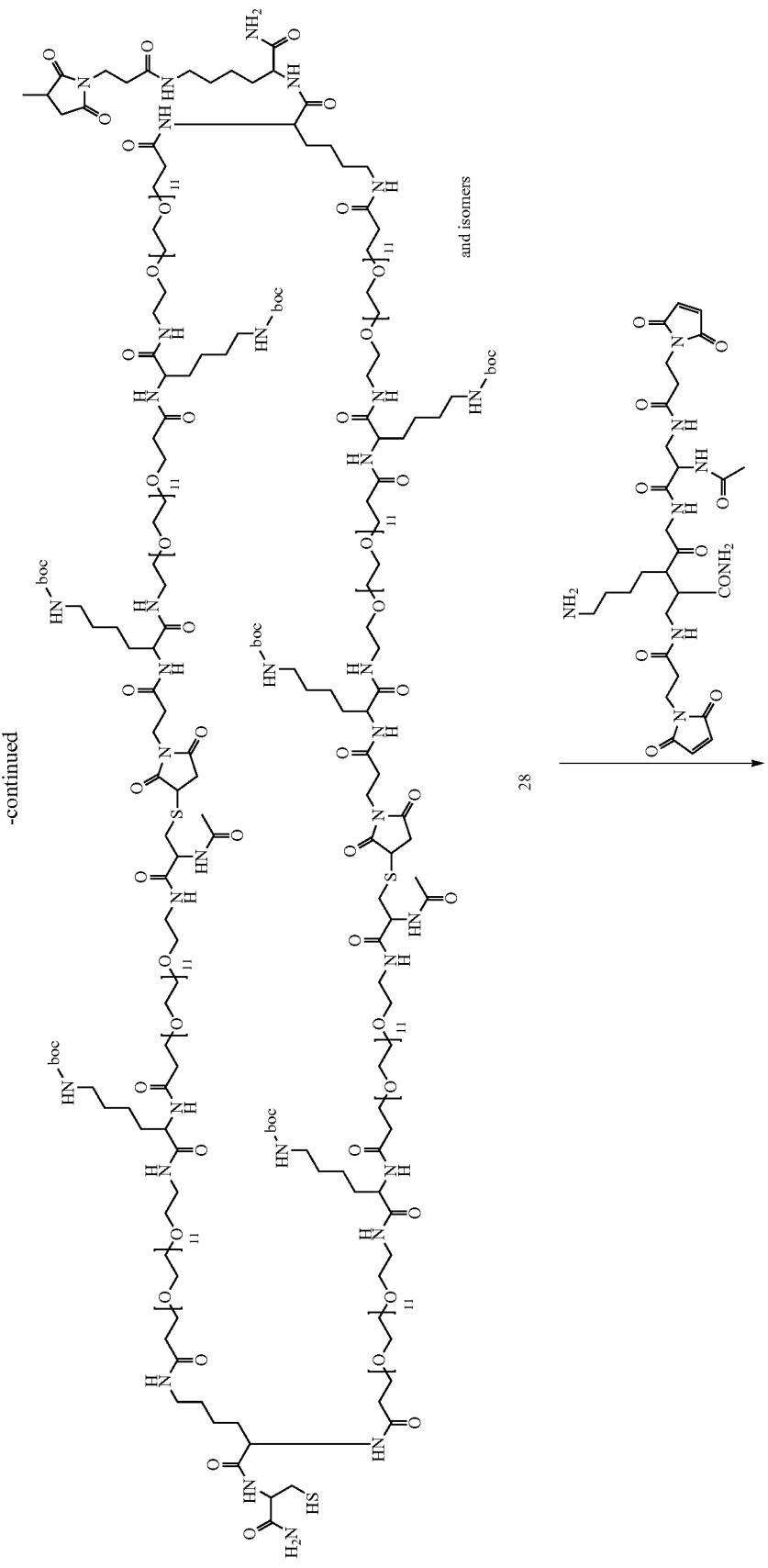
-continued
and isomers
28

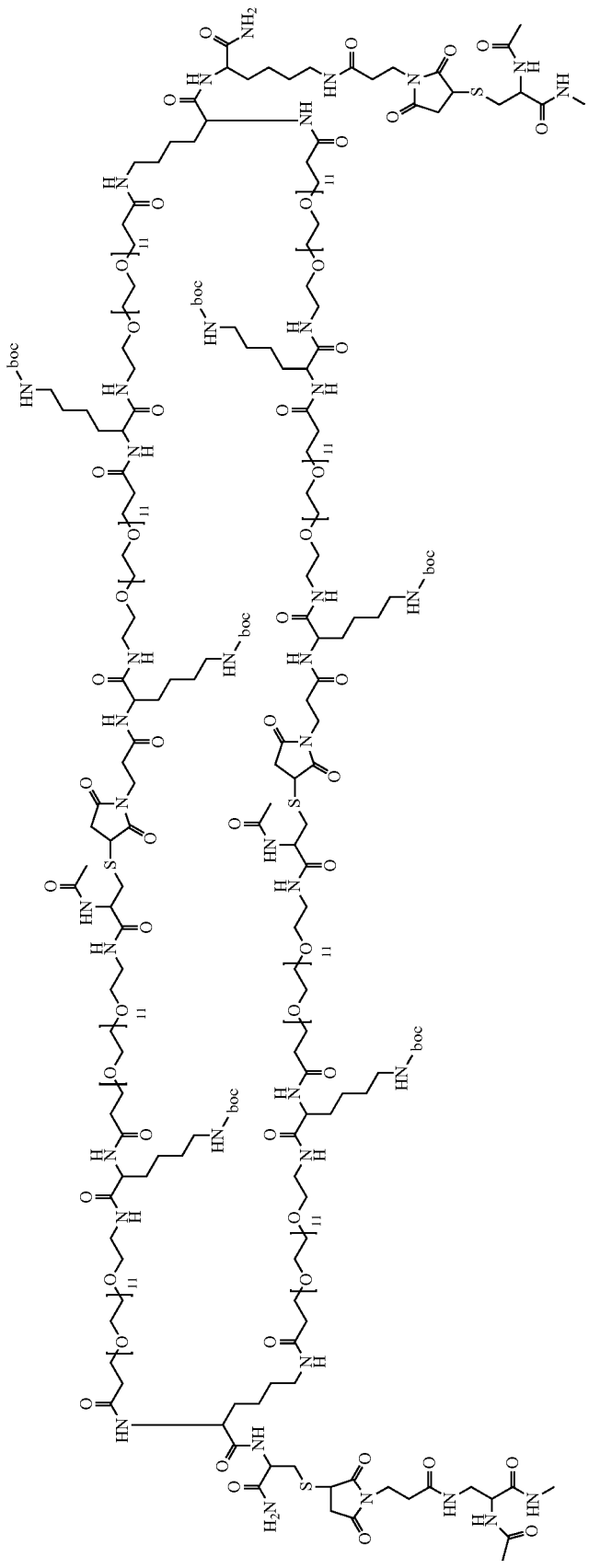

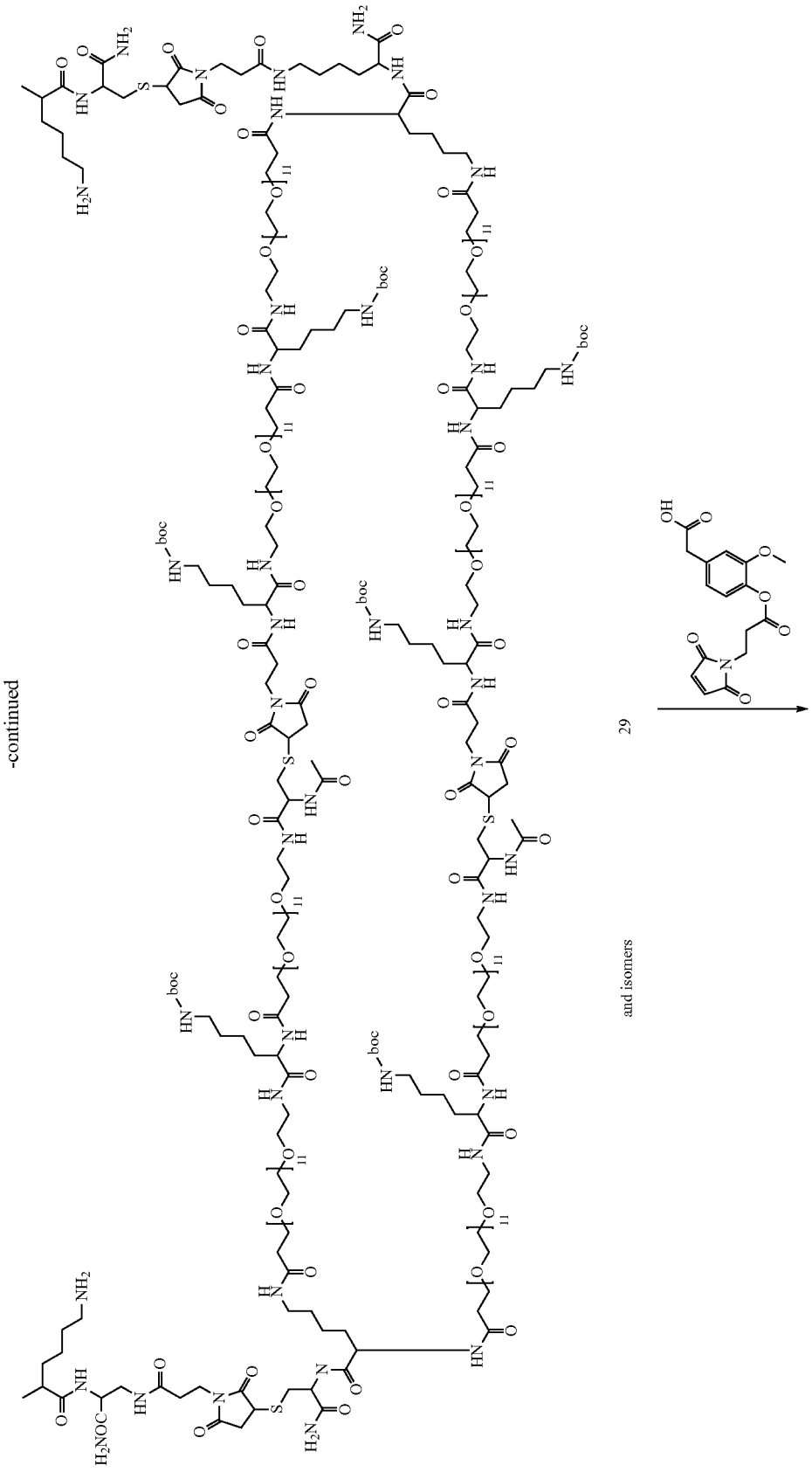

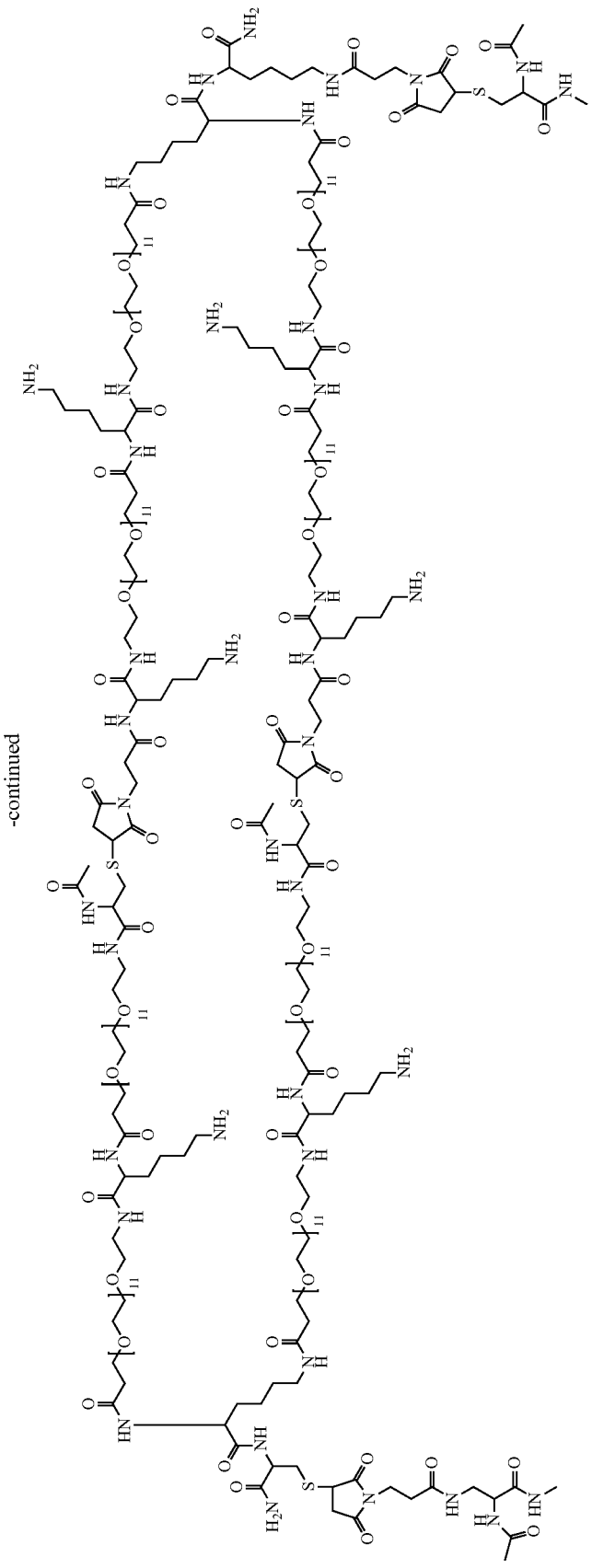

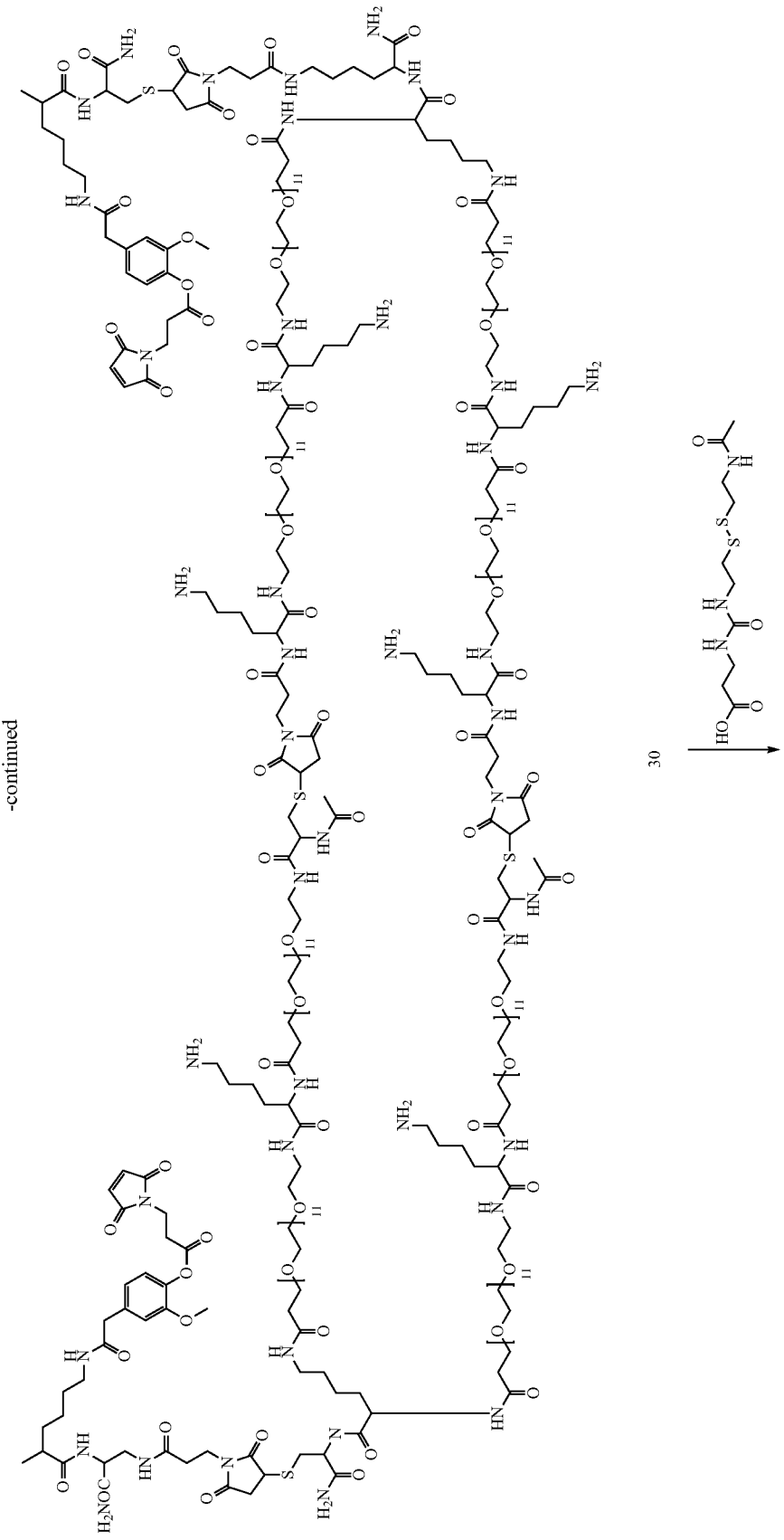

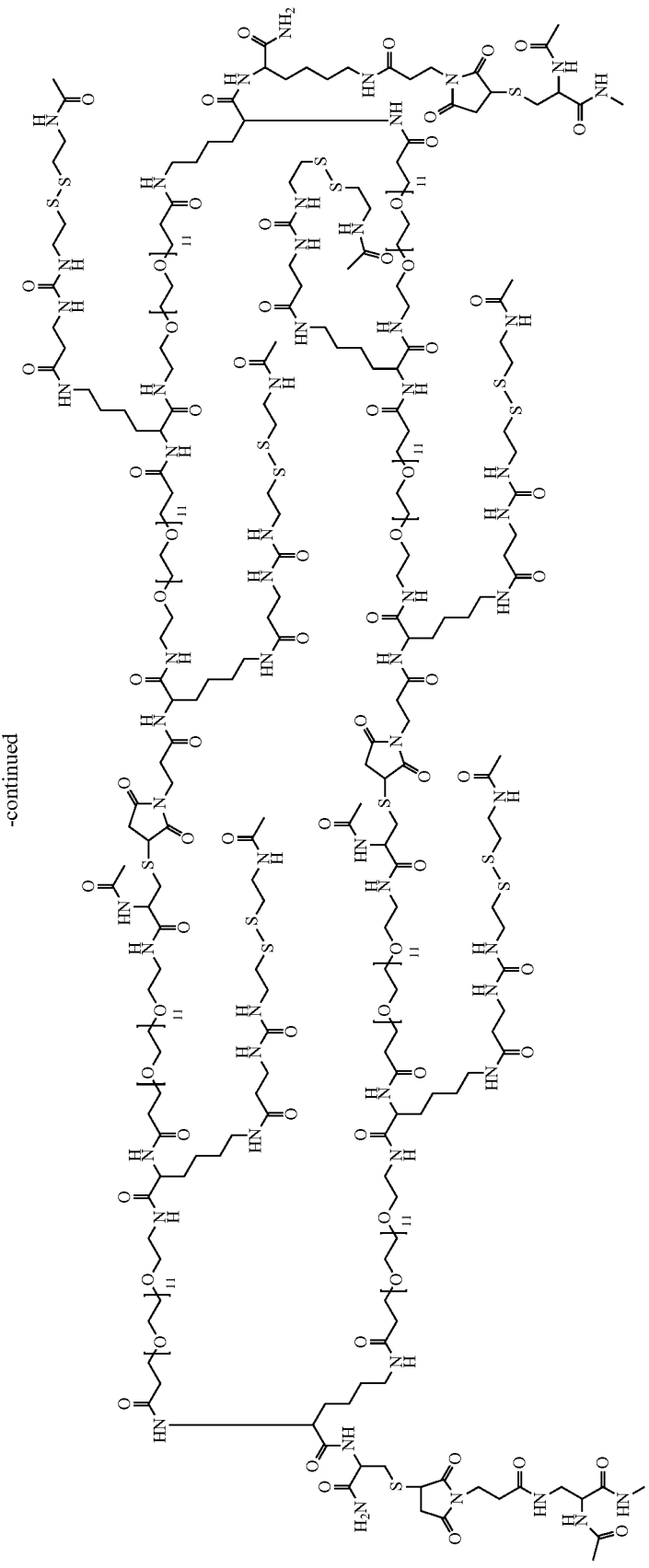

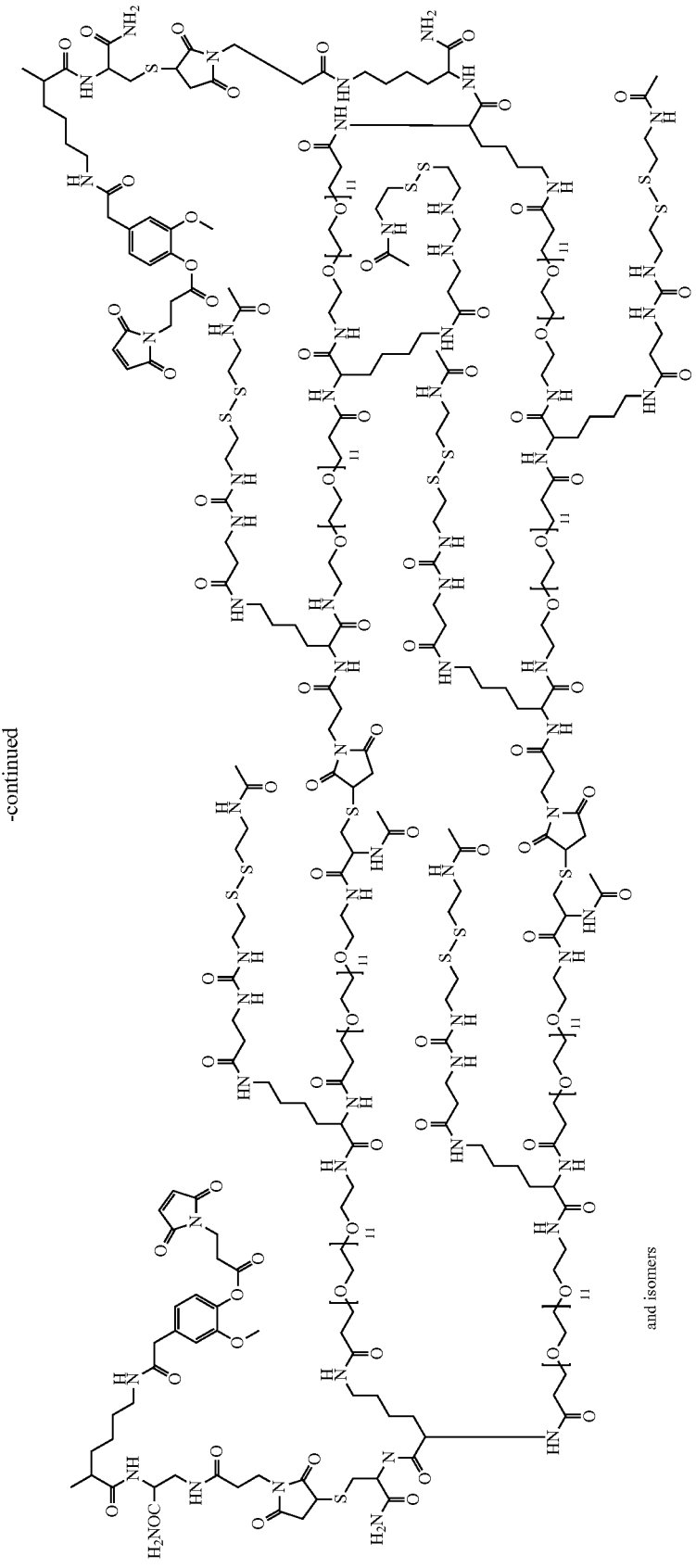
-continued
31
and isomers

Compound 26 was obtained according to the standard protocol for solid phase synthesis. The amino acids Fmoc-Cys(StBu)-OH, Fmoc-Lys(Fmoc)-OH, Fmoc-PP—OH, Fmoc-Lys(Boc)-OH, Fmoc-PP—OH and Fmoc-Cys(Mmt) were coupled to Sieber amide resin. After final Fmoc-removal, resin was treated with a solution of 2/1/1 (v/v/v) DMF/acetic acid anhydride/pyridine for 15 min, washed with dichloromethane and dried in vacuo. Cleavage was performed by repeated treatment (15 times) of the resin for 2 min with a solution of 97/1/2 (v/v/v) dichloromethane/TFA/TES. Collected supernatant was mixed and buffered with 1 eq pyridine (vs. TFA). After concentrating the mixture, compound 26 was purified by RP-HPLC.

MS (MW calculated) 26:3482 g/mol (3482 g/mol)

Compound 27 was obtained according to the standard protocol for solid phase synthesis. Starting from Sieber amide resin, the amino acid sequence Fmoc-Lys(Mtt)-OH, Fmoc-Lys(Fmoc)-OH, Fmoc-PP—OH, Fmoc-Lys(Boc)-OH, Fmoc-PP—OH and Fmoc-Lys(Boc)-OH was assembled. After final Fmoc-removal, the resin was reacted for 30 min with 6 eq maleimidopropionic acid and 6 eq DIC, washed with dichloromethane and dried in vacuo. Cleavage was performed by repeated (15 times) treatment of the resin for 2 min with a solution of 97/1/2 (v/v/v) dichloromethane/TFA/TES. Collected supernatant was mixed and buffered with 1 eq pyridine versus TFA. After concentrating the mixture, compound 27 was purified by RP-HPLC.

MS (MW calculated) 27:3888 g/mol (3887 g/mol)

Compound 28 was obtained from educts 26 and 27 in analogy to the synthesis of 24 from educts 20 and 21 according to protocol II-3.

Cyclization of 28 to 29 was performed in analogy to cyclization of compound 16 according to protocol II-1.

For analysis, a sample was treated with TFA to effect removal of the Boc-protecting groups.

MS (MW calculated without Boc-groups) 29: 14717 g/mol (14720 g/mol)

29 were reacted with 10 eq 6 and 10 eq DIC in DMF for 30 min. Product was purified by RP-HPLC and lyophilized Boc-protecting groups were removed by incubation for 30 min in 1/1 (v/v) TFA/DCM. Solvent was evaporated under nitrogen flow. Extraction of the residue with water and subsequent lyophilization yielded 30.

MS (MW calculated): 15352 g/mol (15360 g/mol)

Product 31 was obtained by reacting 30 with 30 eq 7 and 30 eq DIC in DMF for 45 min Product was purified by RP-HPLC and lyophilized.

MS (MW calculated): 18851 g/mol (18847 g/mol)

II-5) Synthesis of bis-maleimido-core-Maerocyclic Structure 34

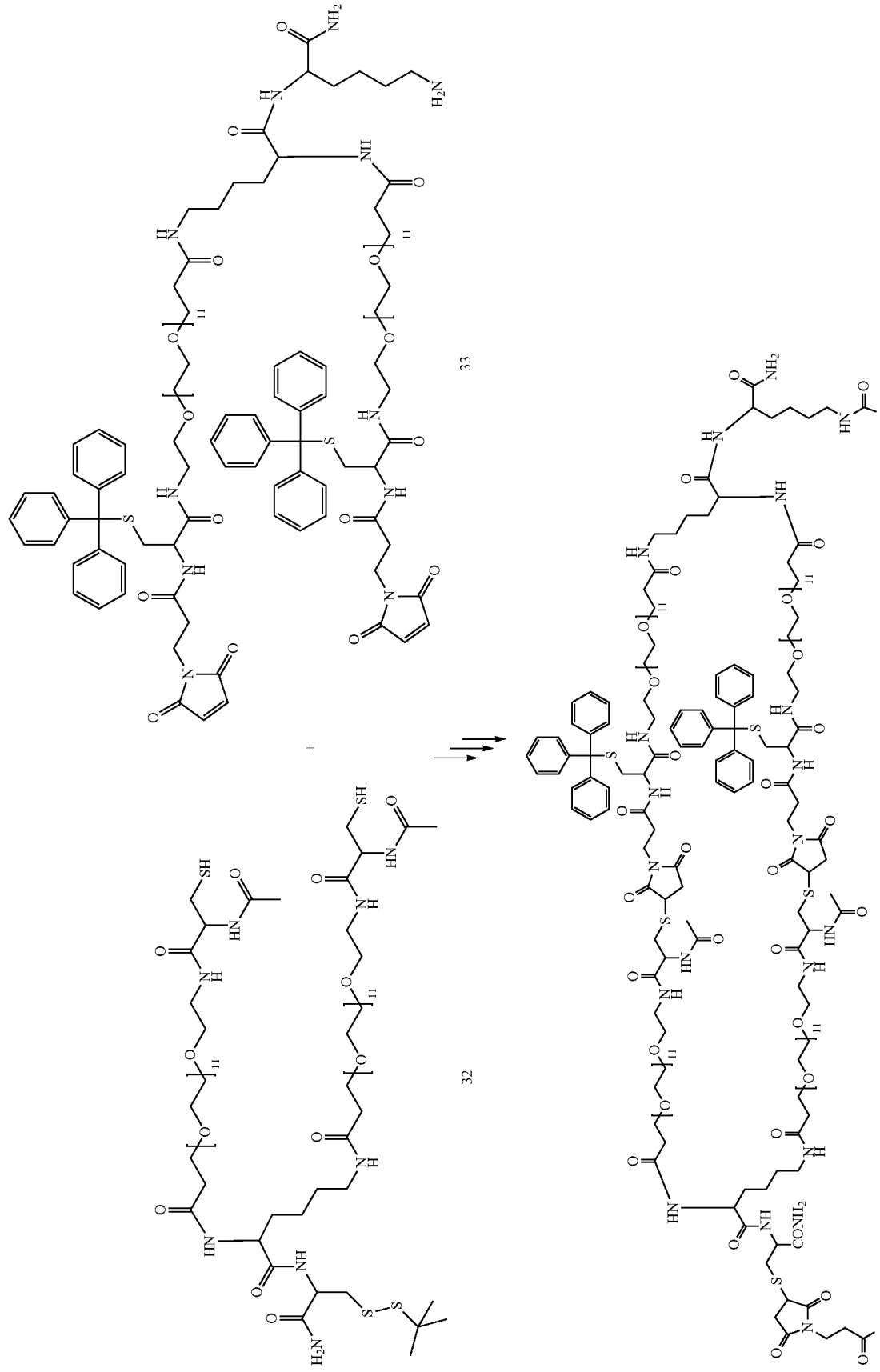

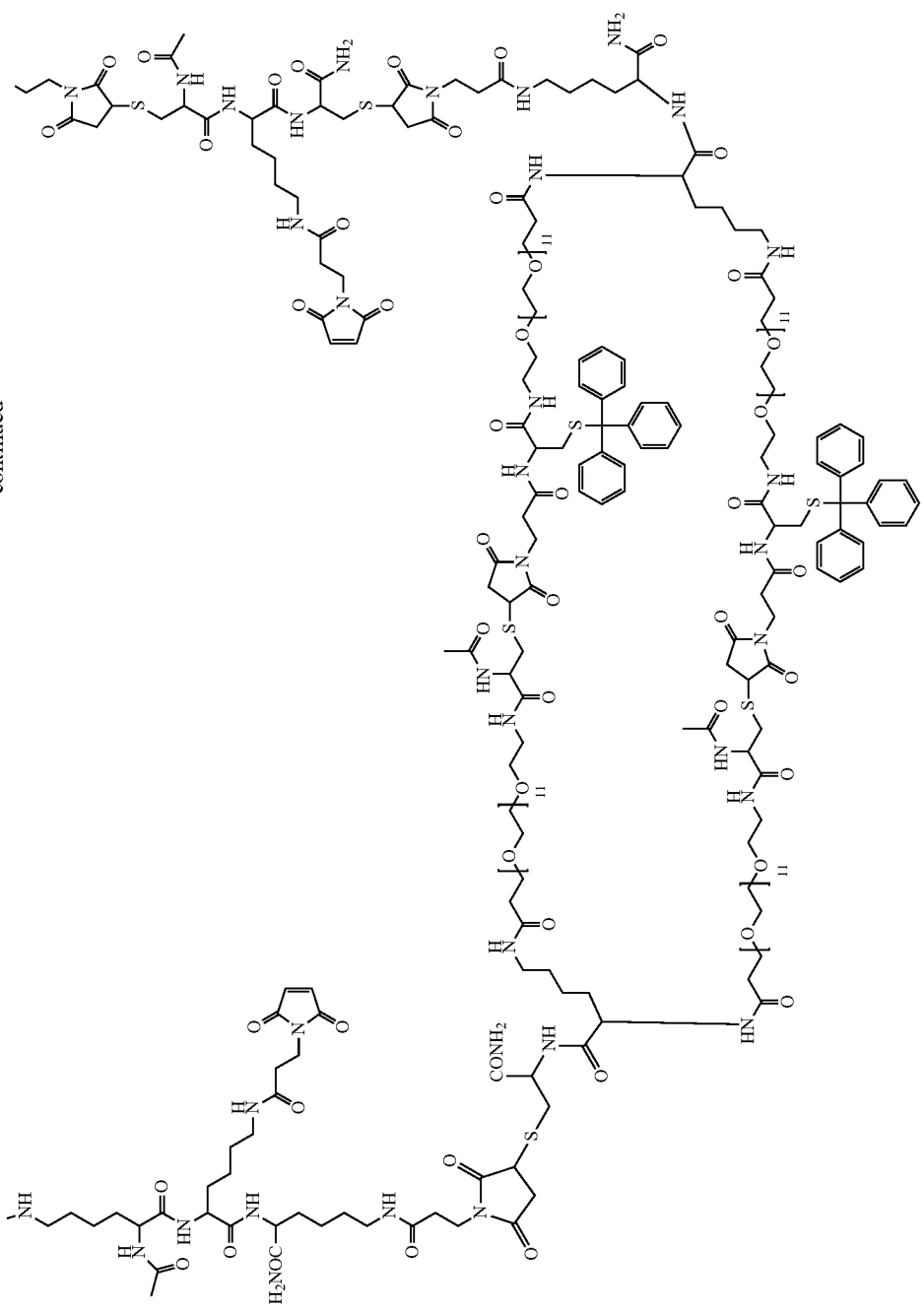

Compound 32 was obtained according to the standard protocol for solid phase synthesis. The amino acids Fmoc-Cys (StBu)-OH, Fmoc-Lys(Fmoc)-OH, Fmoc-PP—OH and Fmoc-Cys(Mmt)-OH were coupled to Sieber amide resin. After final Fmoc-removal, the resin was incubated with a solution of 2/1/1 (v/v/v) DMF/acetic acid anhydride/pyridine for 15 min, washed with dichloromethane, and dried in vacuo. Cleavage from the resin was afforded by treatment with 97/1/2 (v/v/v) Dichlormethan/ TFA/TES for 30 min. After concentration, product 32 was purified by RP-HPLC Compound 33 was obtained according to the standard protocol for solid phase synthesis. The amino acids Fmoc-Lys (Mtt)-OH, Fmoc-Lys(Fmoc)-OH, Fmoc-PP—OH and Fmoc-Cys(Trt)-OH were coupled with Sieber amide resin. After final Fmoc-removal, the resin was incubated with 6 eq maleimidopropionic acid and 6 eq DIC for 30 min, washed with dichloromethane, and dried in vacuo. Cleavage from the resin was afforded by treatment with 99/1/(v/v) dichloromethane/ TFA for 15 min and repeated washing with DCM. Pooled eluates were buffered with 0.75 eq pyridine (versus TFA) and solvent was removed in vacuo. Product was purified by RP-HPLC.

MS (MW calculated) 33:2466 g/mol (2466 g/mol)

Synthesis of 34 was performed in analogy to the cyclization of compound 25 according to protocol II-3, except for the use of Ac-Lys(Mal)-Lys-Lys(Mal)-$NH_2$ instead of Ac-Dpr (Mal)-Lys-Dpr(Mal)-$NH_2$. For analysis, a sample of 34 was treated with 48/50/2 (v/v/v) TFA/DCM/TES for 10 min to effect removal of the Trt-protecting groups.

MS (MW calculated without Trt groups) 34: 9183 g/mol (9183 g/mol)

III—Synthesis of Proteophore-Capping Reagents

III-1) Synthesis of Mal-PEG4×5k (37)

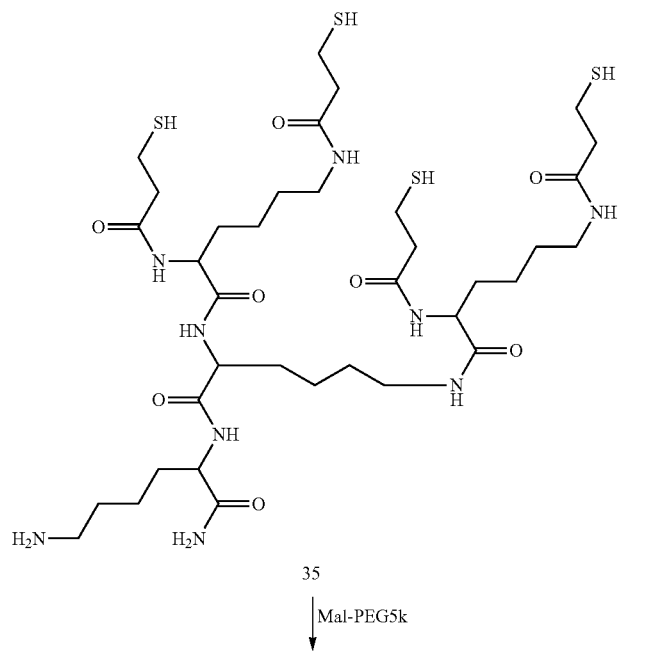

35

↓ Mal-PEG5k

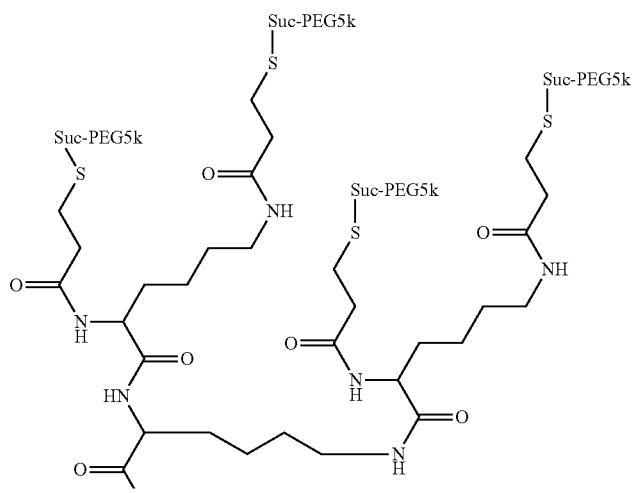

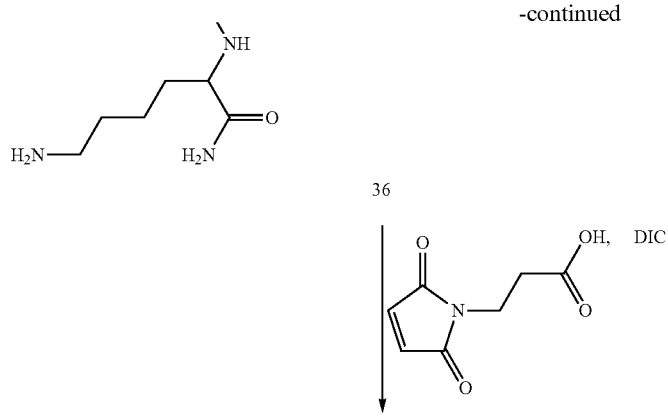

36

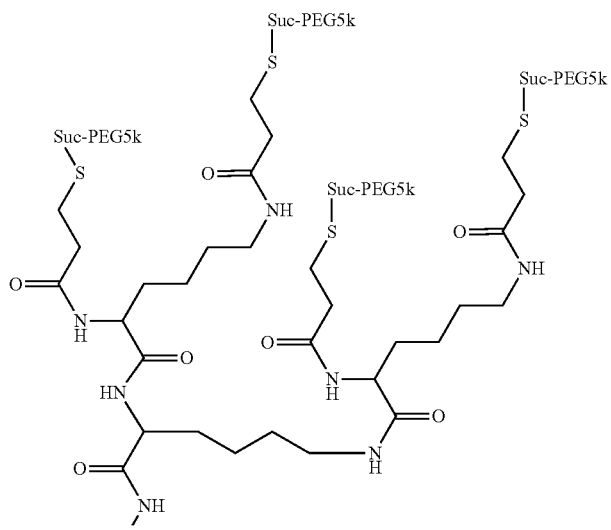

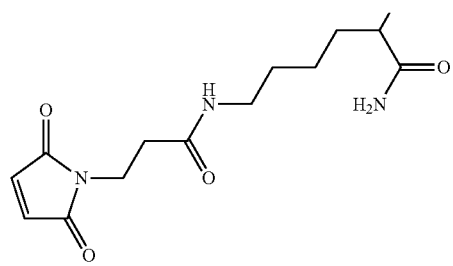

37

Compound 35 was obtained according to the standard protocol for solid phase synthesis. The amino acids Fmoc-Lys(Boc)-OH, Fmoc-Lys(Fmoc)-OH and Fmoc-Lys(Fmoc)-OH were coupled to TGR resin, and Mmt-3-mercaptopropionic (8) acid was used as the terminal building block. After resin cleavage, product was purified by RP-HPLC.

MS (MW calculated) 35: 881.5 g/mol (882 g/mol)

Compound 35 and 4.1 eq Maleimide-PEG5k were dissolved in 0.1 M sodium phosphate buffer (pH 7.0) and stirred for 30 min. Excess Maleimide-PEG5k was reacted with mercaptoethanol and product 36 was purified by RP-HPLC and lyophilized.

Compound 36 was taken up in DMF, 6 eq maleimidopropionic acid and 6 eq DIC in DMF were added and the mixture was agitated for 30 min. The product was purified by RP-HPLC and characterized by size exclusion chromatography (Superdex 200 column, flow rate: 0.75 ml/min)

SEC (retention time) 36: 16 min

III-2) Synthesis of Mal-PP4×1.25 k (38)

38
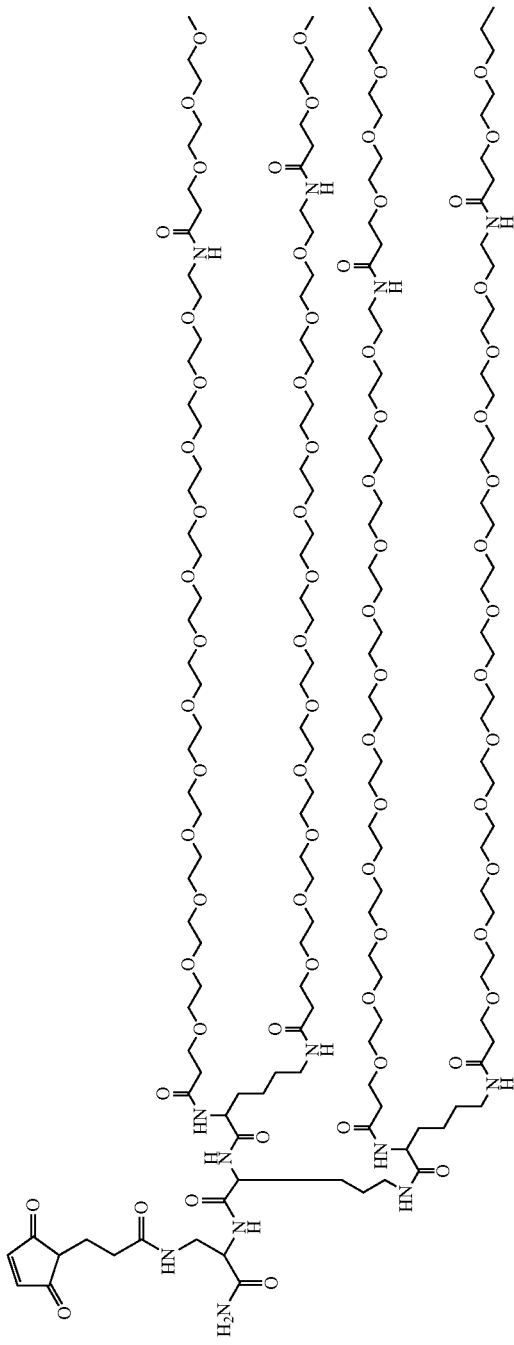
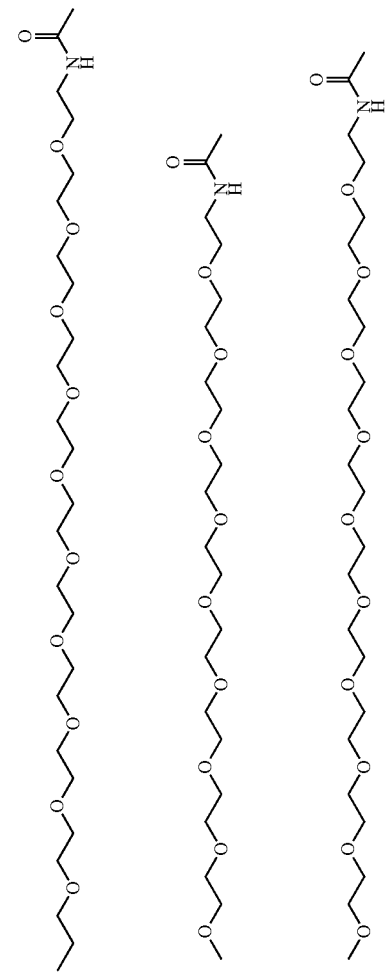

Compound 38 was obtained according to the standard protocol for solid phase synthesis. The amino acids Fmoc-Dpr(ivDde)-OH, Fmoc-Lys(Fmoc)-OH, Fmoc-Lys(Fmoc)-OH and two units of Fmoc-PP—OH were coupled to TGR resin. After final Fmoc-removal, resin was incubated with a solution of 2/1/11 (v/v/v)

DMF/acetic acid anhydride/pyridine for 15 min Removal of the ivDde-protecting group was afforded by repeatedly agitating (three times) the resin for 5 min with 98/2 (v/v) DMF/hydrazine. The resin was washed with DMF and treated for 30 min with a solution of 6 eq maleimidopropionic acid and 6 eq DIC in DMF. After cleavage from the resin the product was purified by RP-HPLC.

MS (MW calculated) 38: 5600 g/mol (5603 g/mol)

IV—Synthesis of a Hemogobin MPIC

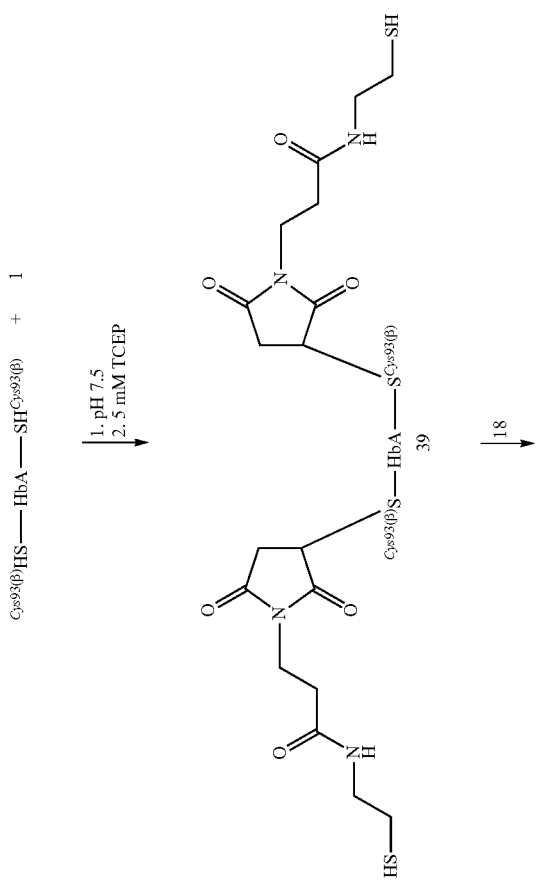

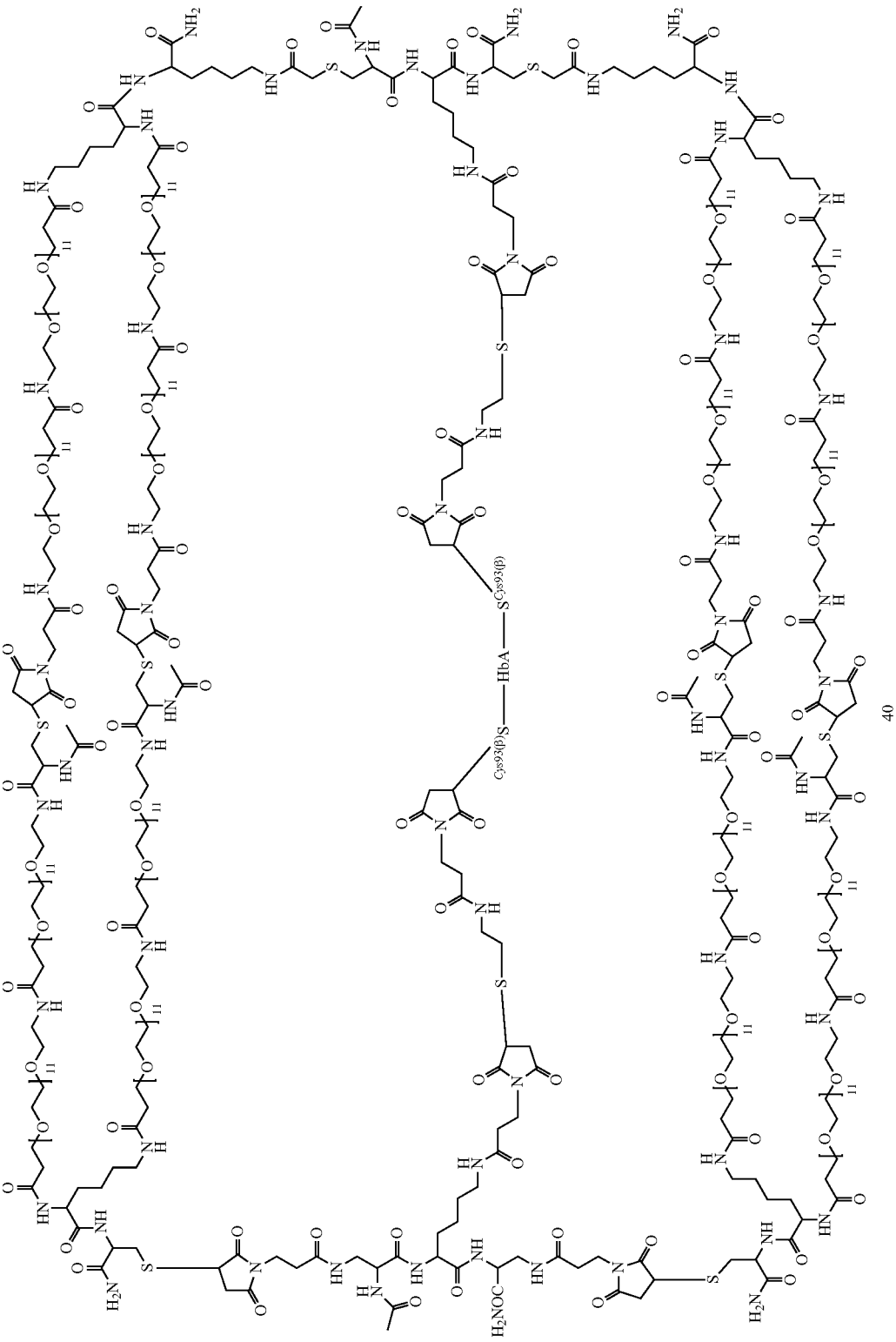

IV-1) Modification of Hb Cys93(β) with Linker 1

Human hemoglobin (Hb) was adjusted to a concentration of 10 mg/ml in 0.1 M sodium phosphate buffer (pH 7.5), 5 eq 1 were added and the mixture was agitated for 30 min at RT. Excess 1 was removed by size exclusion chromatography (PD10 column).

MS alpha-subunit, unmodified (MW calculated): 15121 g/mol (15127 g/mol)

MS beta-subunit (MW calculated): 16208 g/mol (16214 g/mol)

Cleavage of the disulfide bond of the conjugated linker was effected by reduction of the modified Hb for 30 min in 5 mM TCEP (pH 7.5). Product 39 was purified by SEC (Superdex 200).

MS alpha subunit, unmodified (MW calculated) 39: 15121 g/mol (15127 g/mol)

MS beta subunit (MW calculated) 39: 16090 g/mol (16096 g/mol)

IV-2) Conjugation to bis-maleimido-macrocycic Structure 18

Compound 39 was adjusted to a concentration of 20 μM in 0.1 M phosphate buffer (pH 7.5) and 2 eq of 18 were added. After incubation for 20 min at RT, the resulting Hb MPIC 40 was purified by SEC (Superdex 200 column). FIG. 1 displays size exclusion chromatograms of native Hb, 39, the reaction mixture of 39 and Hb, and purified product 40.

MS alpha subunit, unmodified (MW calculated) 40: 15122 g/mol (15127 g/mol)

MS crosslinked beta subunits (MW calculated) 40: 45432 g/mol (45454 g/mol)

V—Synthesis of a Cleavable Hemoglobin MPIC

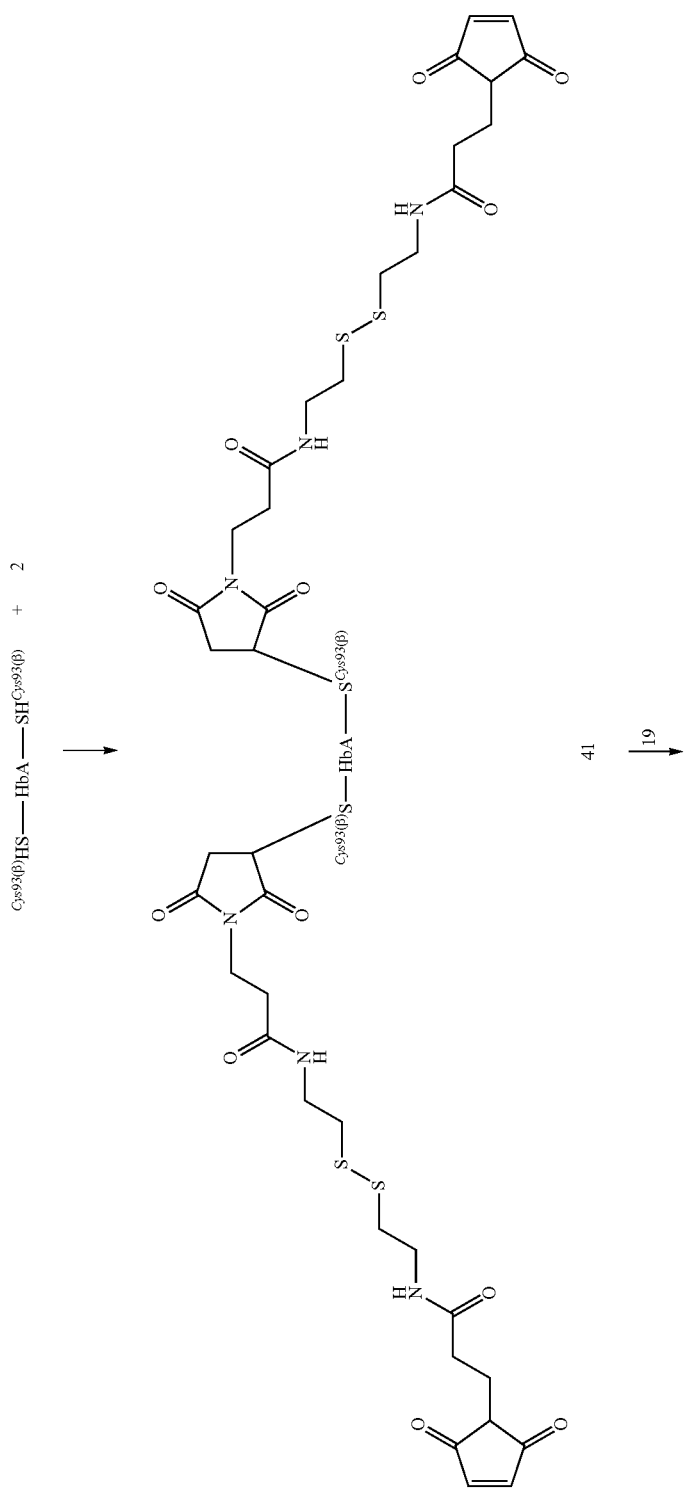

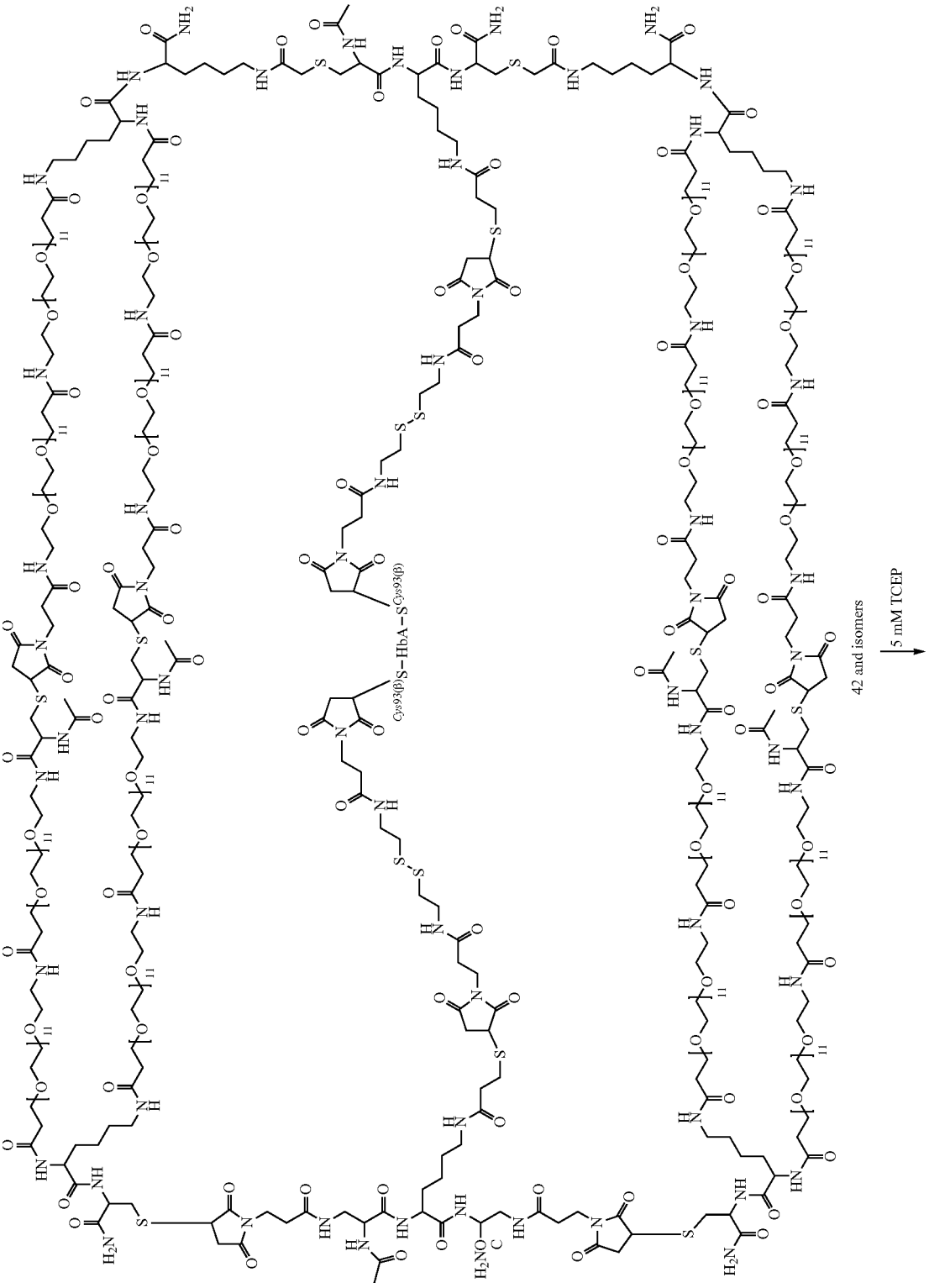

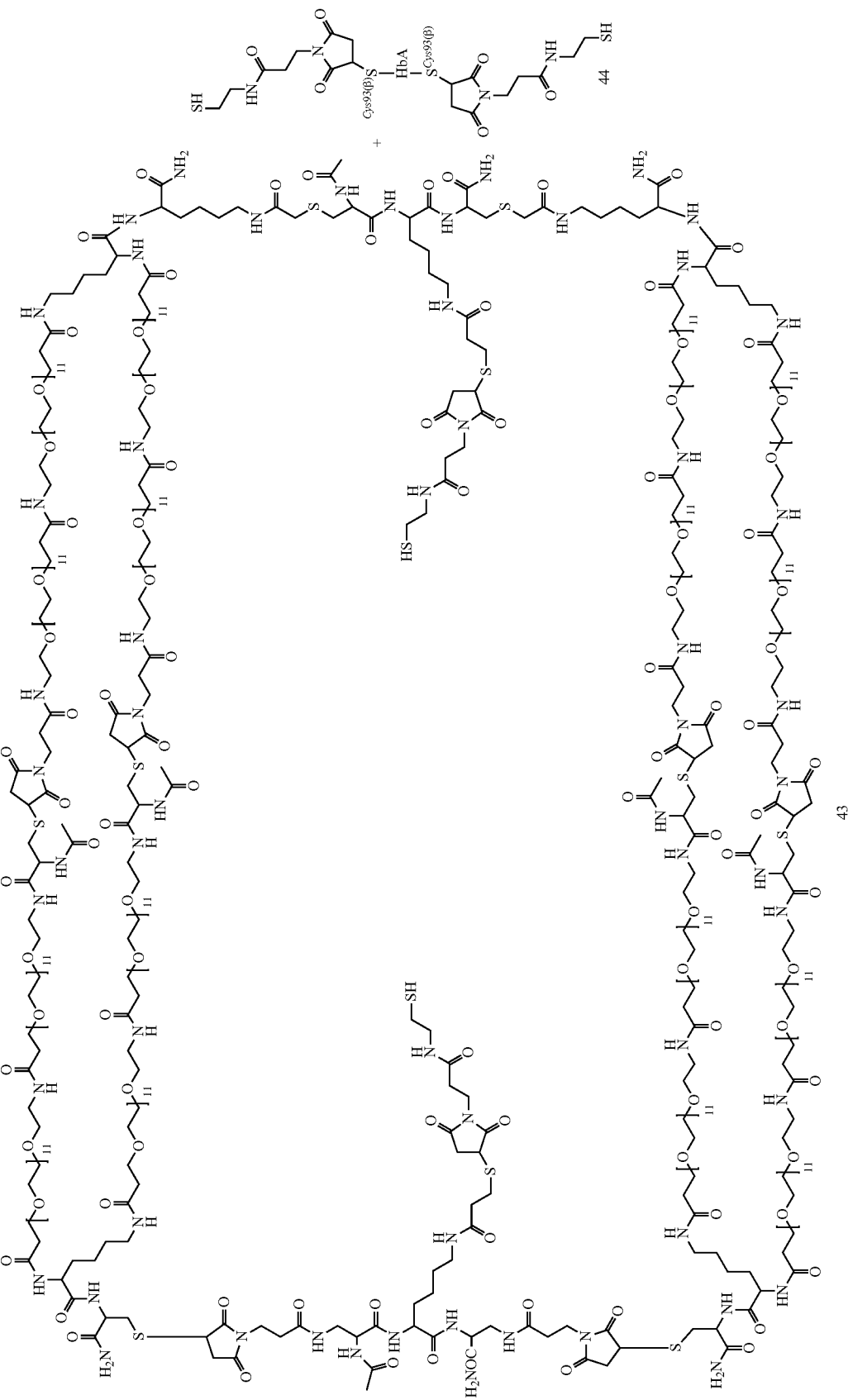

V-1) Modification of Hb Cys93(β) with Linker 2

Hb was adjusted to a concentration of 10 mg/ml in 0.1 M sodium phosphate buffer (pH 7.5). After addition of 10 eq 2 the solution was agitated for 30 min at RT. Hb-conjugate 41 was purified by SEC (Superdex 200).

MS alpha subunit, unmodified (MW calculated) 41: 15123 g/mol (15127 g/mol)

MS beta subunit (MW calculated) 41: 16318 g/mol (16322 g/mol)

V-2—Conjugation to bis-thiol-macrocyclic Structure 19

The concentration of 41 was adjusted to 20 μM in 0.1 M phosphate buffer (pH 7.5). After addition of 2 eq 19 the solution was incubated for 45 min at RT. The Hemoglobin MPIC 42 was purified by SEC (Superdex 200).

MS alpha subunit (MW calculated) 42: 15125 g/mol (15127 g/mol)

MS beta subunit (MW calculated) 42: 45776 g/mol (45780 g/mol)

In order to prove the reversibility of the conjugation, product 42 was treated with 5 mM TCEP in 0.1 M phosphate buffer (pH 7.5). The quantitative release of Hb from the MPIC was assessed by LC/MS.

MS beta subunit (MW calculated) 42: 16091 g/mol (16096 g/mol)

Figure 2:
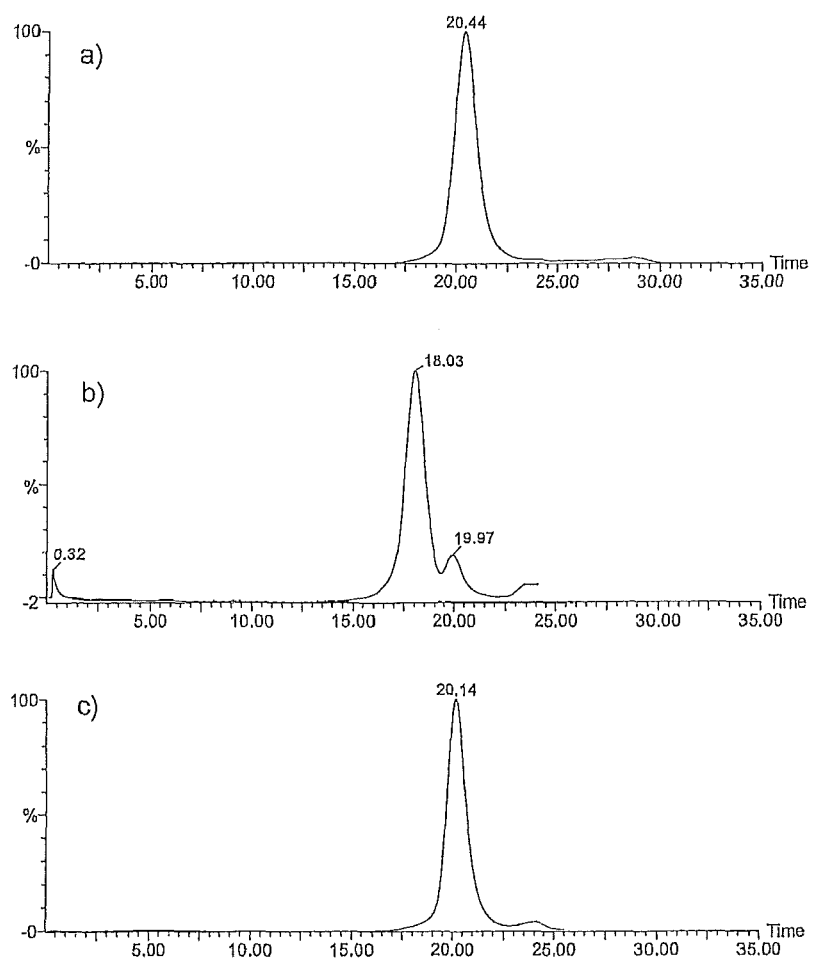
FIG. 2 Size exclusion chromatograms of a) 41, b) 42 and c) Hb released from 42. UV signals were recorded at 280 nm.

FIG. 2 displays size exclusion chromatograms of 41, 42 and of Hb (44) released from 42.

VI—Synthesis of a Hemoglobin MPIC with Capping Reagents

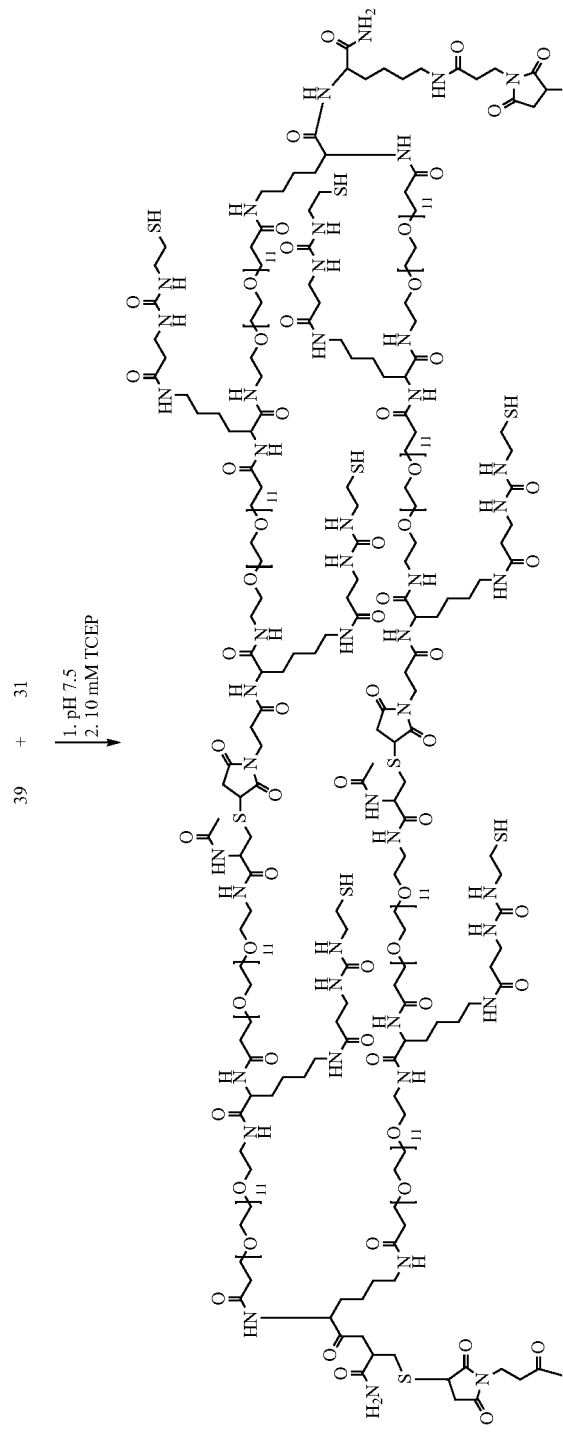

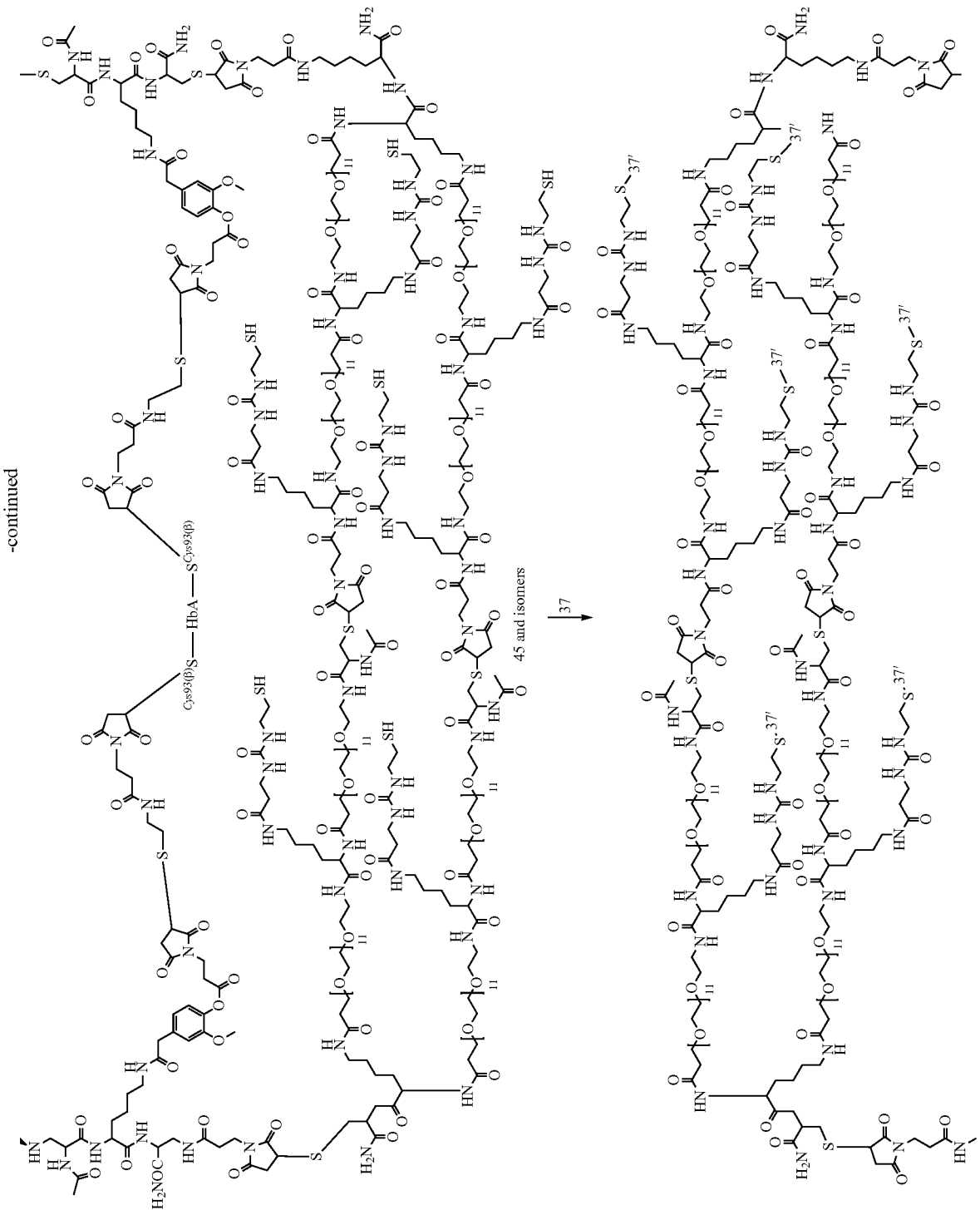

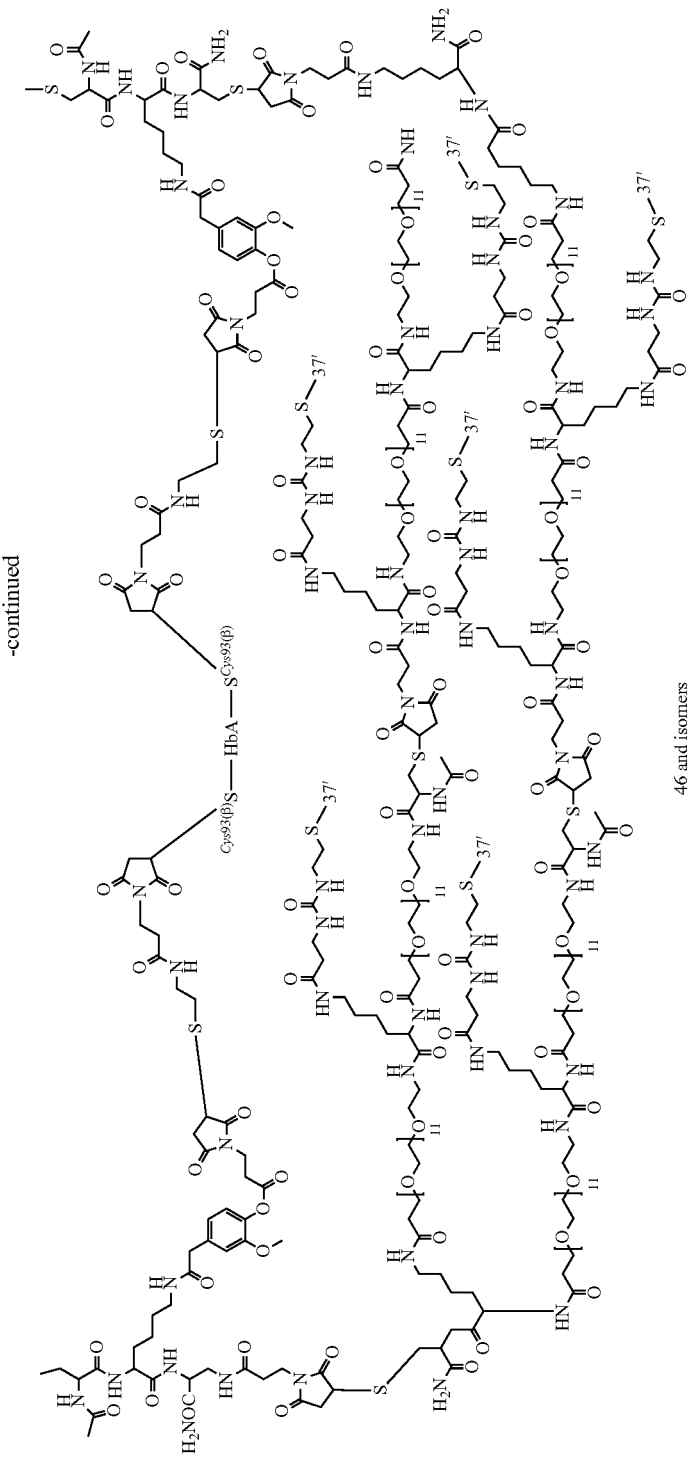
46 and isomers

Structural element 37' represents the succinimidyl-containing product of the Michael addition of the neighboring proteophore thiol to the maleimido group of 37.

VI-1) Conjugation of 39 to bis-maleimide-macrocyclic Structure 31

The conjugation of 39 to 31 was performed according to protocol IV-2 in analogy to the preparation of 40. Disulfide-moieties associated with the proteophore were reduced by incubation in 10 mM TCEP (pH 7.5) for 30 min. Product 45 was purified by SEC (Superdex 200 column).

VI-2) Modification of Hemoglobin MPIC with Mal-PEG4×5k (37)

Compound 45 was reacted with 30 eq 37 for 1 h at RT in 50 mM sodium phosphate buffer (pH17.0) and purified by SEC (Superdex 200, flow rate: 0.75 ml/min).

SEC (retention time) 46: 11.2 min

VII—Synthesis of an Insulin MPIC

VII-1) Synthesis of $N^{\alpha A1}$-Boc-insulin 47

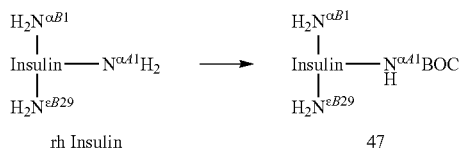

Insulin was dissolved in DMSO and reacted with 1.1 eq $(t\text{-BOC})_2O$ for 60 min to yield $N^{\alpha A1}$-Boc-insulin 47. Purification was achieved by RP-HPLC. Enzymatic digestion of 47 with endo-GluC and subsequent characterisation of the resulting fragments by LCMS confirmed regioselective modification of the amino terminus of the A chain of insulin.

MS (MW calculated) 47: 5907 g/mol (5907 g/mol)

VII-2) Synthesis of $N^{\alpha A1}$-Boc,$N^{\alpha B1}$,$N^{\epsilon B29}$-bis-(thiol-linker)-insulin 49

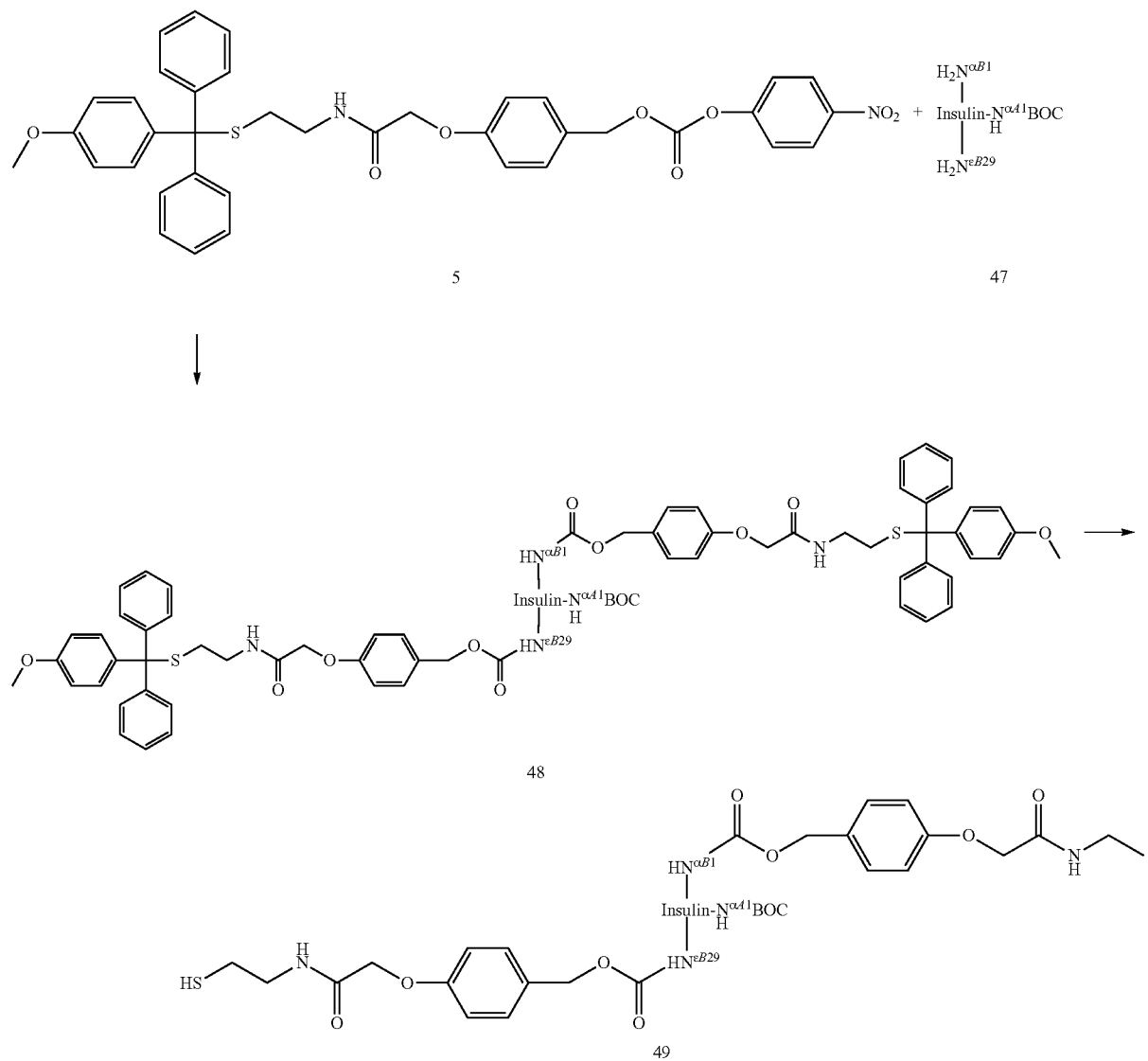

47 was dissolved in DMSO and incubated with 10 eq of activated linker 5 for 5 h at pH 8-9. The pH was adjusted by addition of DIEA, if necessary. Subsequent RP-HPLC purification afforded $N^{\alpha A1}$-Boc,$N^{\alpha B1}$,$N^{\epsilon B29}$-bis-(Mmt-thiol-linker)-insulin 48. After lyophilization, the Mmt-protecting group was removed by incubation for 30 min with 1/99 (v/v) TFA/DCM and product $N^{\alpha A1}$-Boc,$N^{\alpha B1}$,$N^{\epsilon B29}$-bis-(thiol-linker)-insulin 49 was purified by RP-HPLC.

MS (MW calculated) 49: 6450 g/mol (6442 g/mol)

VII-3) Synthesis of macrocyclic Structure-Insulin Conjugates 50a and 50b

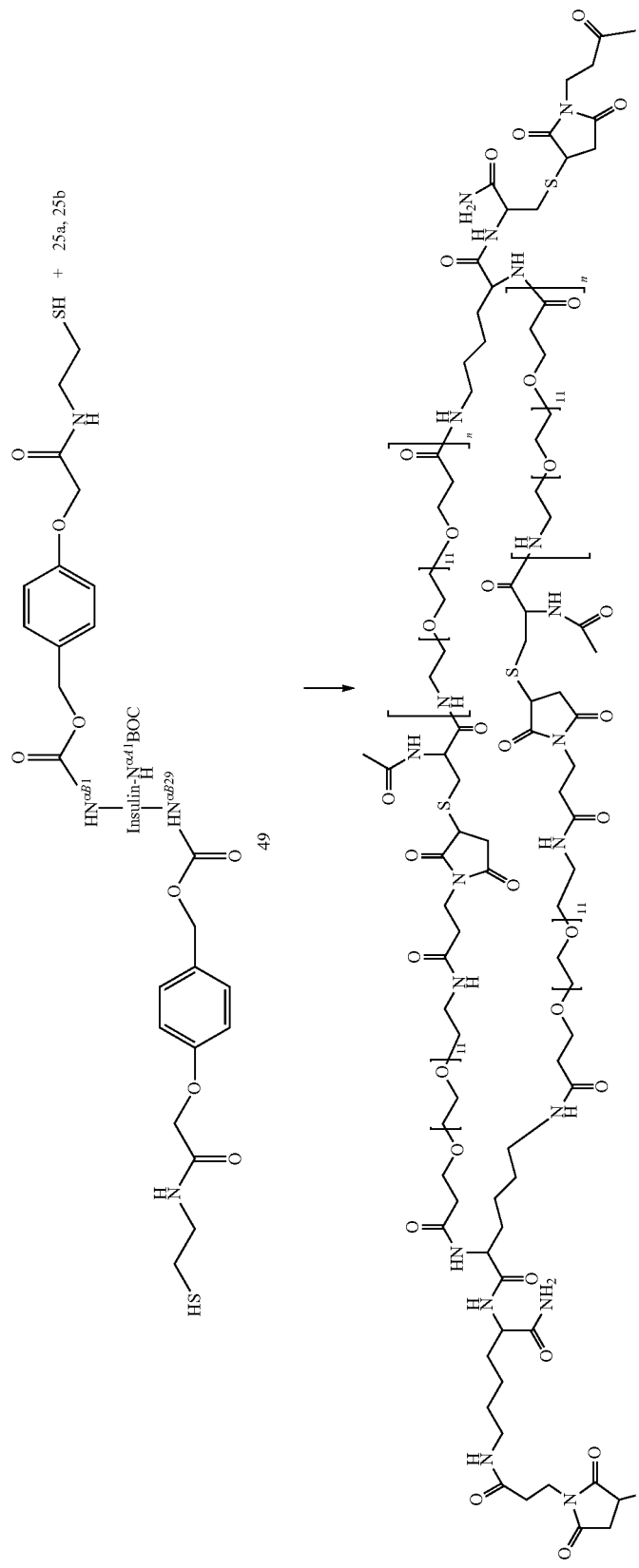

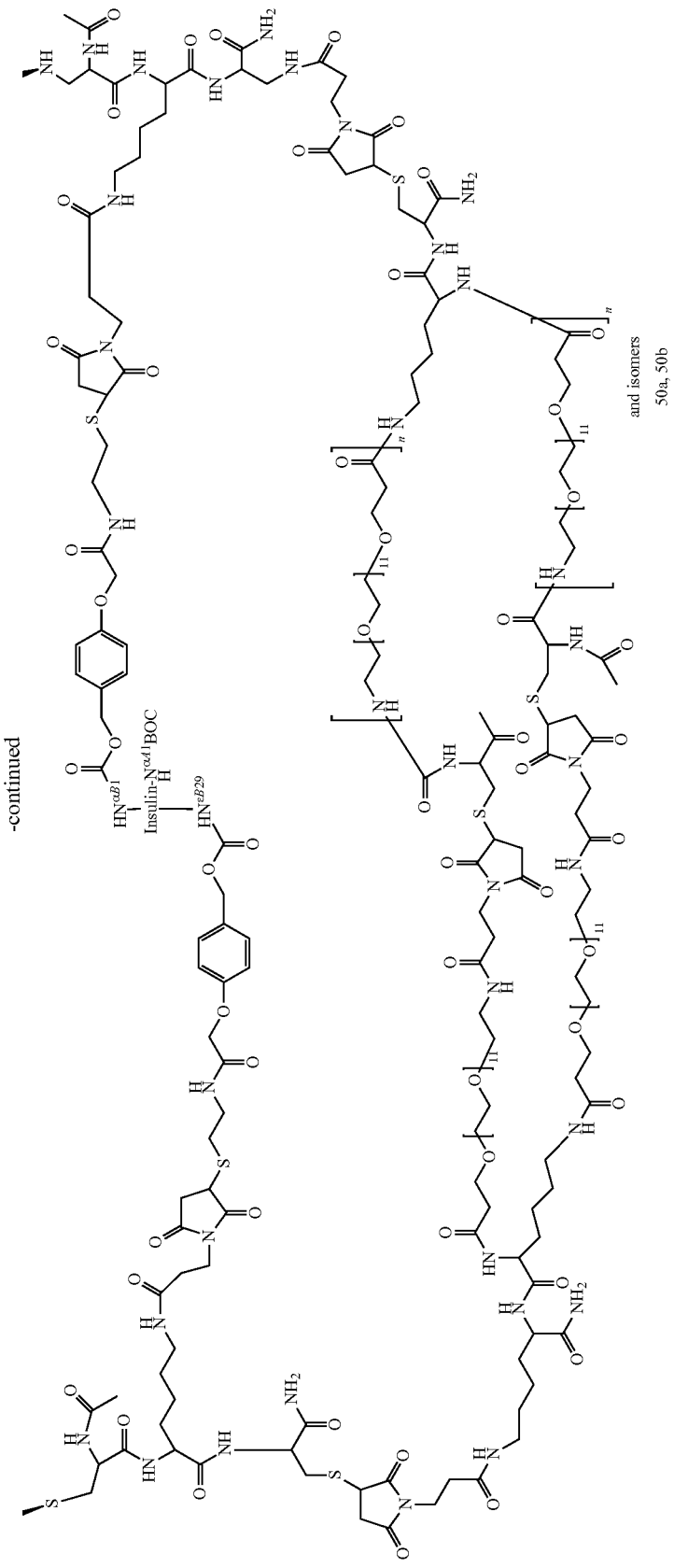

A solution of 49 (20 µM) in 3/1 (v/v) 25 mM phosphate buffer (pH 7.5)/acetonitrile was reacted with 1.1 eq of 25a or 25b, respectively, for 15 mM to yield 50a or 50b, respectively. Purification was achieved by RP-HPLC.

MS (MW calculated) 50a: 15128 g/mol (15128 g/mol)
MS (MW calculated) 50b: 17527 g/mol (17527 g/mol)

VII-4) Release of Insulin from Insulin MPIC 50a/50B

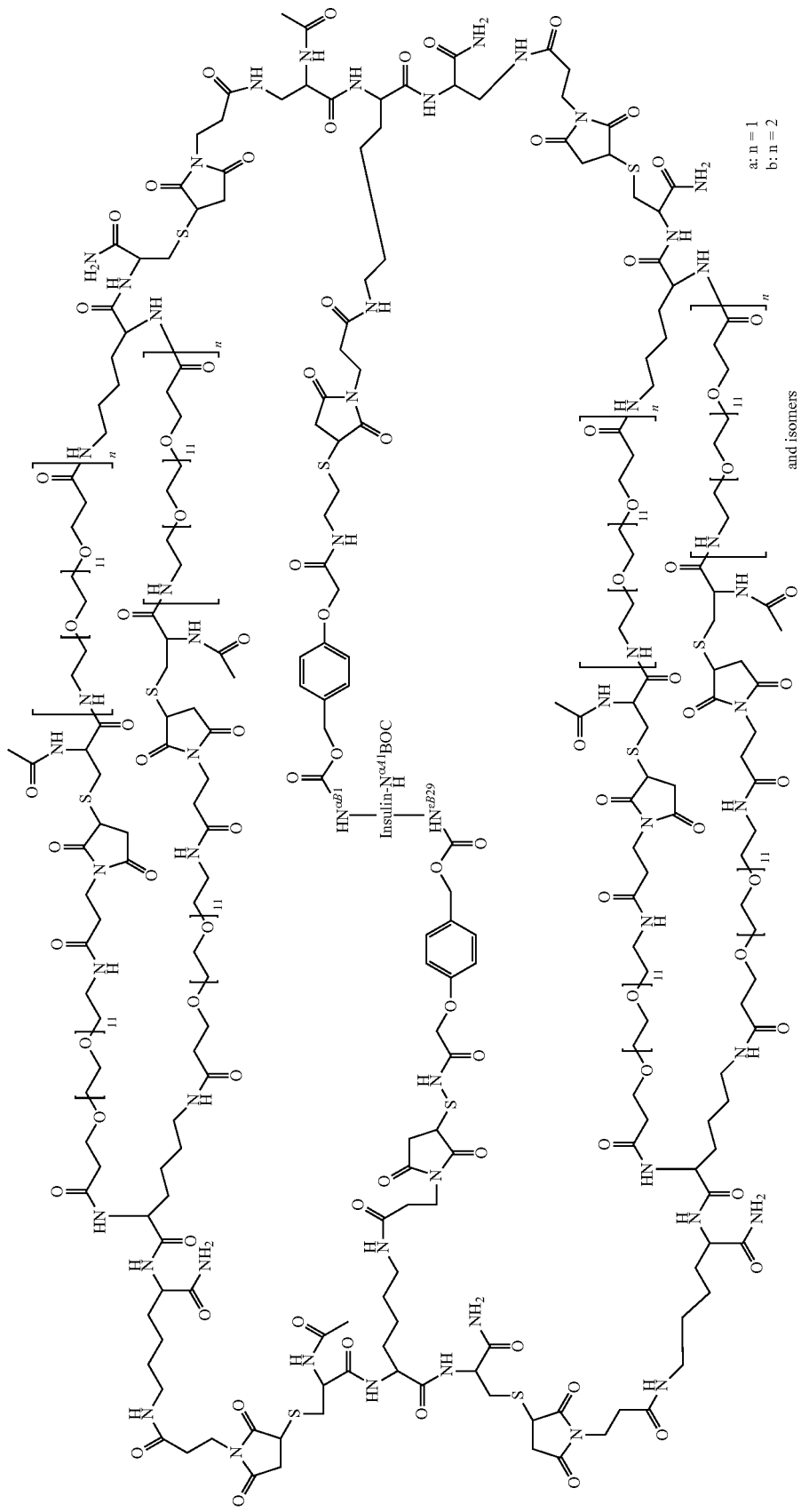

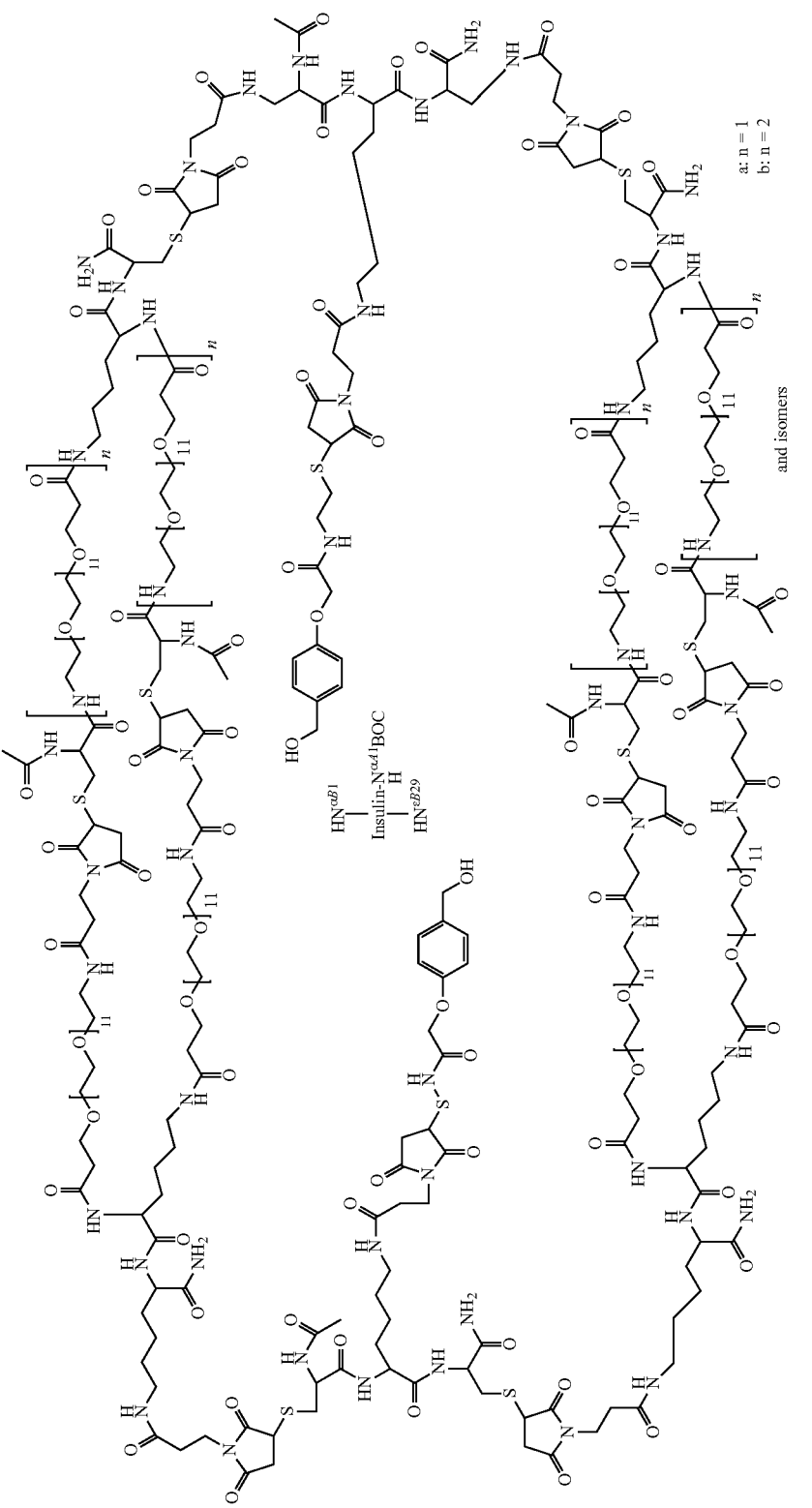

-continued
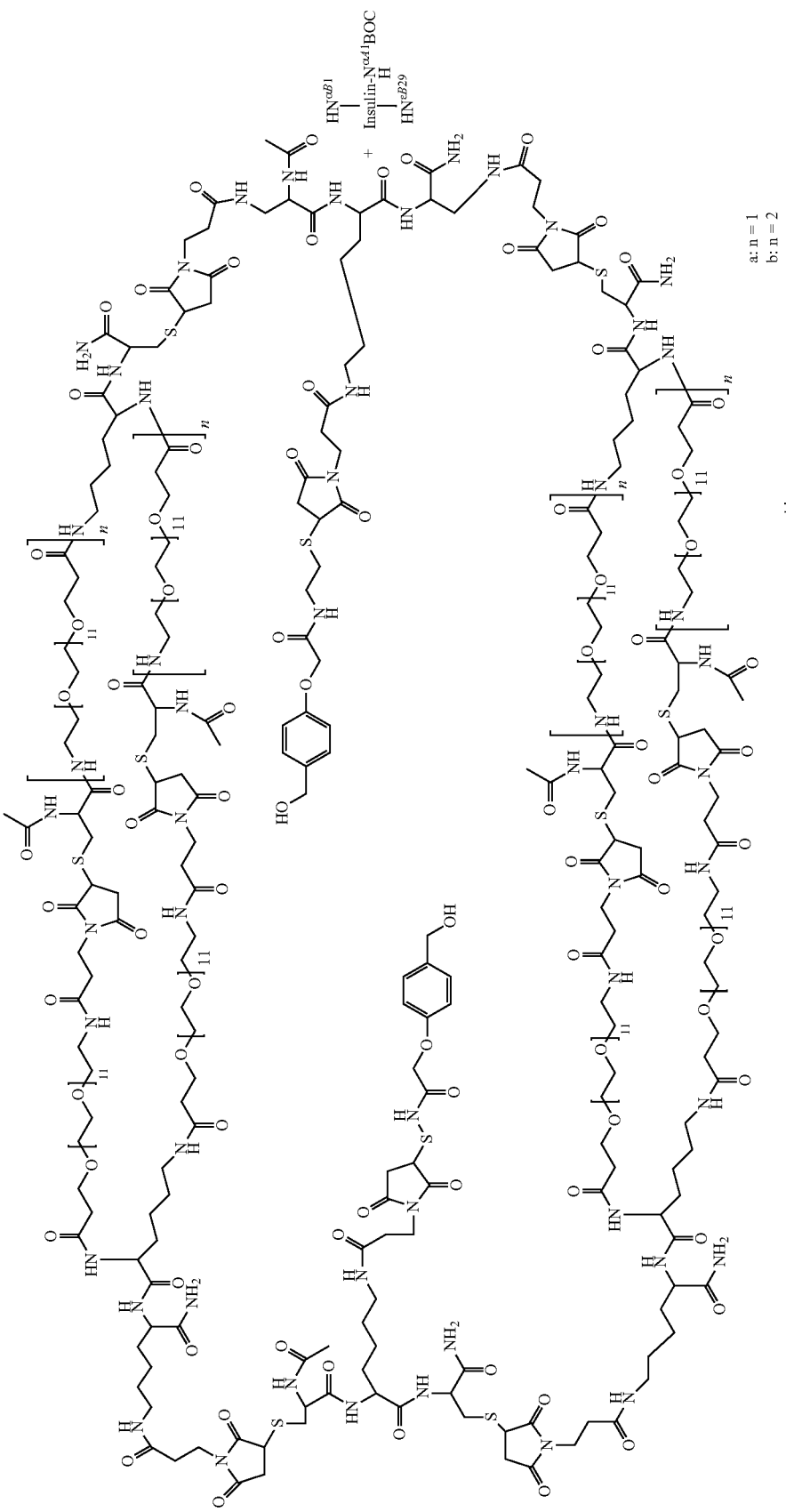
a: n = 1
b: n = 2
and isomers
52a, 52b

Insulin was released from conjugates 50a or 50b, respectively, by cleavage of the linker moieties by incubation with 1:1 (v/v) DCM/TFA for 15 min. These conditions also effected removal of the Boc-protection group on the α-Aminogruppe of the insulin A-chain.

Educts 50a and 50b, linker cleavage mixtures containing released insulin and remaining macrocyclic structures 52a and 52b were characterized by SEC (Superdex 200, flow rate: 0.75 ml/min).

Figure 3:
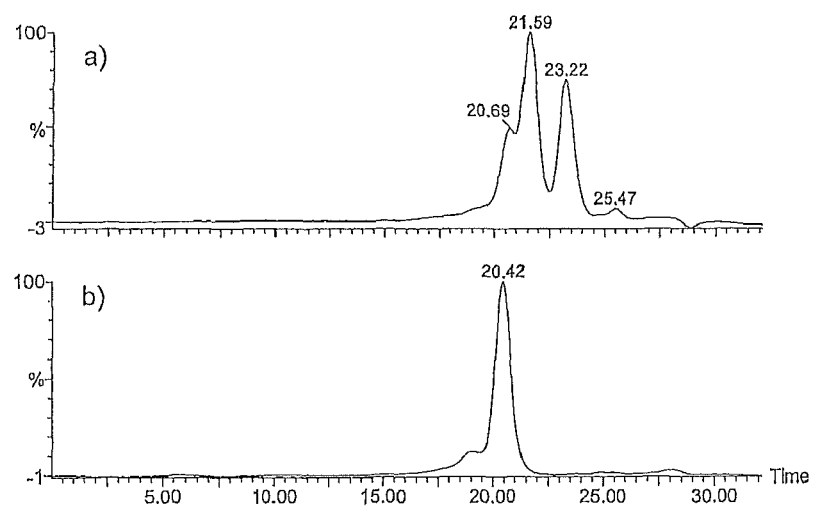
FIG. 3: Size exclusion chromatograms of a) reaction mixture resulting from linker cleavage procedure performed on 50a,b) Insulin MPIC 50a. UV signals were recorded at 280 nm.
Figure 4:
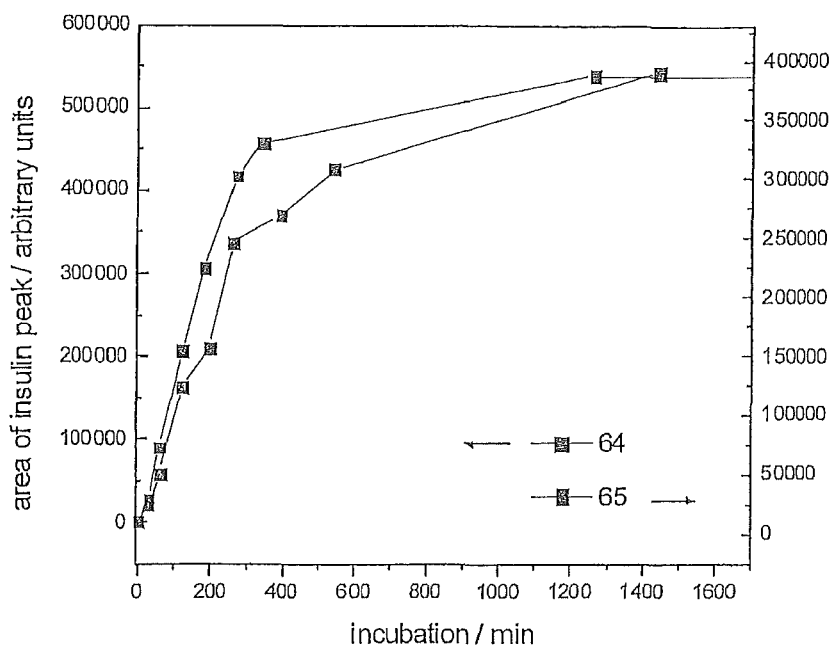
FIG. 4: In vitro release of insulin from Insulin MPIC 64 or 65, respectively. Kinetics were determined by HPLC using UV detection at 215 nm.

FIG. 3 displays size exclusion chromatograms of 50a and products of the linker cleavage procedure. Three peaks were detected and identified by LCMS analysis. The peak at retention time 23.2 min contains insulin, the peak at 21.6 min is EOC 52a. The peak at retention time 20.7 min corresponds to EOC-insulin-monoconjugate.

VIII—Synthesis of Insulin MPIC 57, 58 and 59

VIII-1) Synthesis of $N^{\alpha B1}, N^{\epsilon B29}$-bis-(mercaptopropionyl)-insulin 54

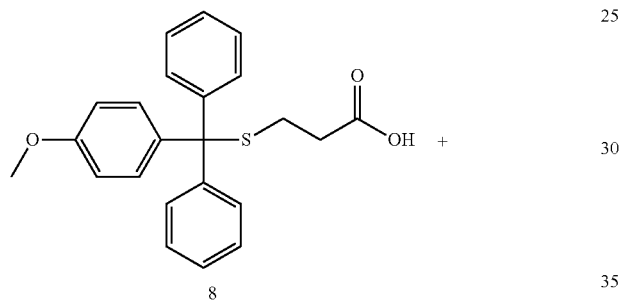

8

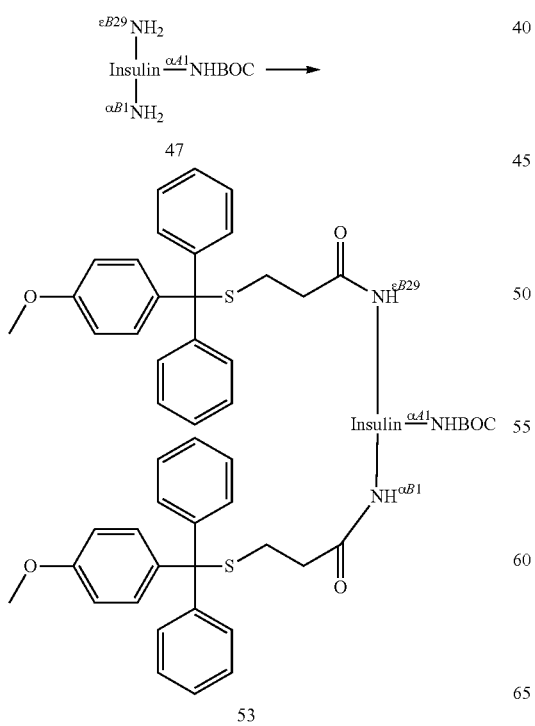

47

53

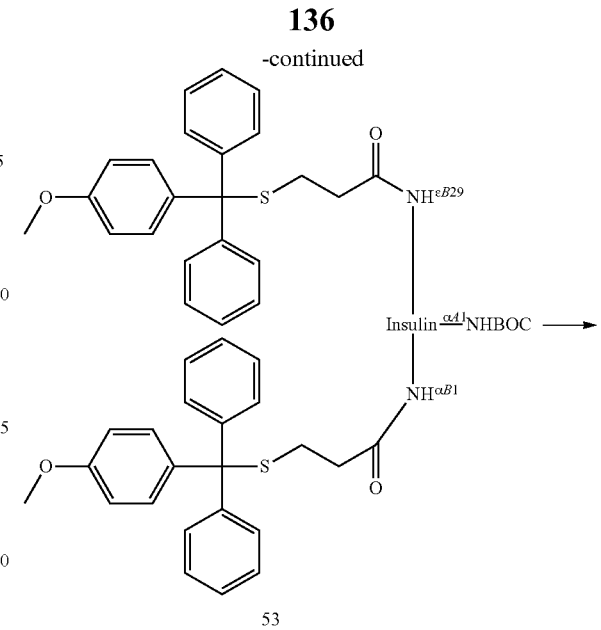

53

240 μl of a solution containing 0.64 M DIC, 0.56 M 8 and 0.29 M N-hydroxysuccinimide in DMF were preincubated for 30 min. 15 mg 47 were dissolved in 1 ml 1/1 (v/v) DMSO/water and mixed with 40 μl DIEA. The mixtures were combined and incubated for 1 h. Compound 53 was purified by RP-HPLC.

MS (MW calculated) 53:6630 g/mol (6627 g/mol)

After lyophilization, Mmt- and Boc-protection groups were removed by incubation with 2/48/50 (v/v/v) TES/TFA/DCM for 30 min. Product 54 was purified by RP-HPLC.

MS (MW calculated) 54: 5981 g/mol (5983 g/mol)

VIII-2) Synthesis of Insulin MPIC 56

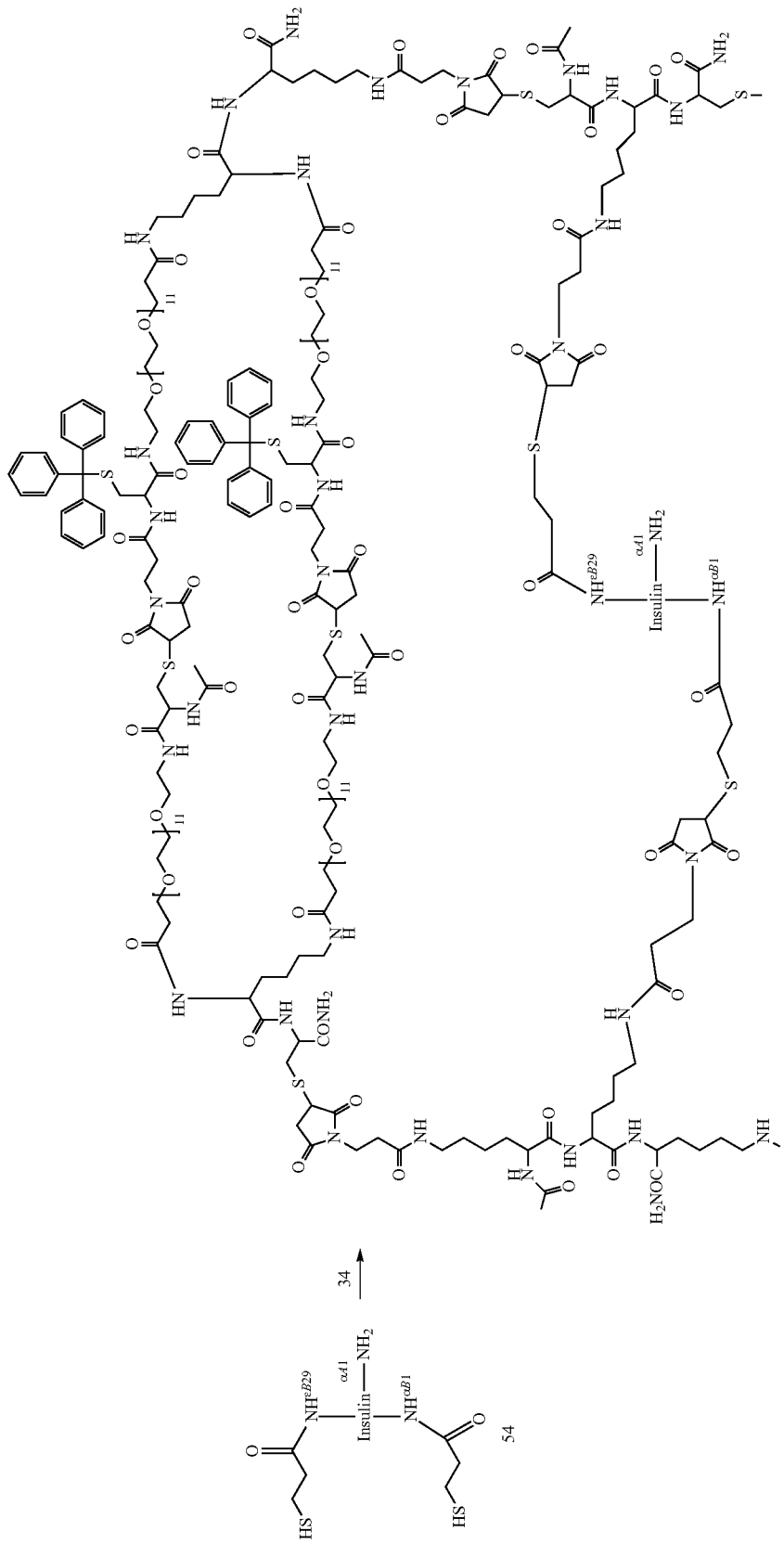

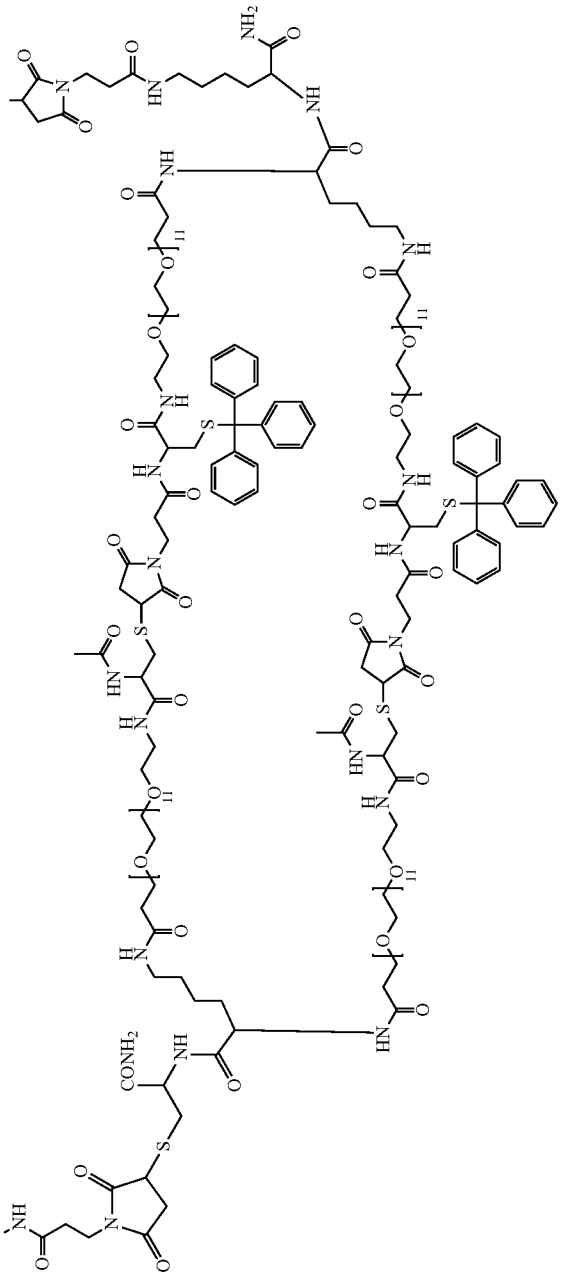
55 and isomers

150 μl of a 3 mM solution of compound 54 in 1/1 (v/v) water/acetonitrile were mixed with 270 μl of a 1.5 mM solution of macrocyclic structure 34 in 1/1 (v/v) water/acetonitrile and diluted with 20/80 (v/v) acetonitrile/water to a total volume of 22 ml. Subsequently, pH was adjusted to 7.5 by addition of 0.5 M phosphate buffer pH 8.0. After 15 min incubation, compound 55 was purified by RP-HPLC and lyophilized.

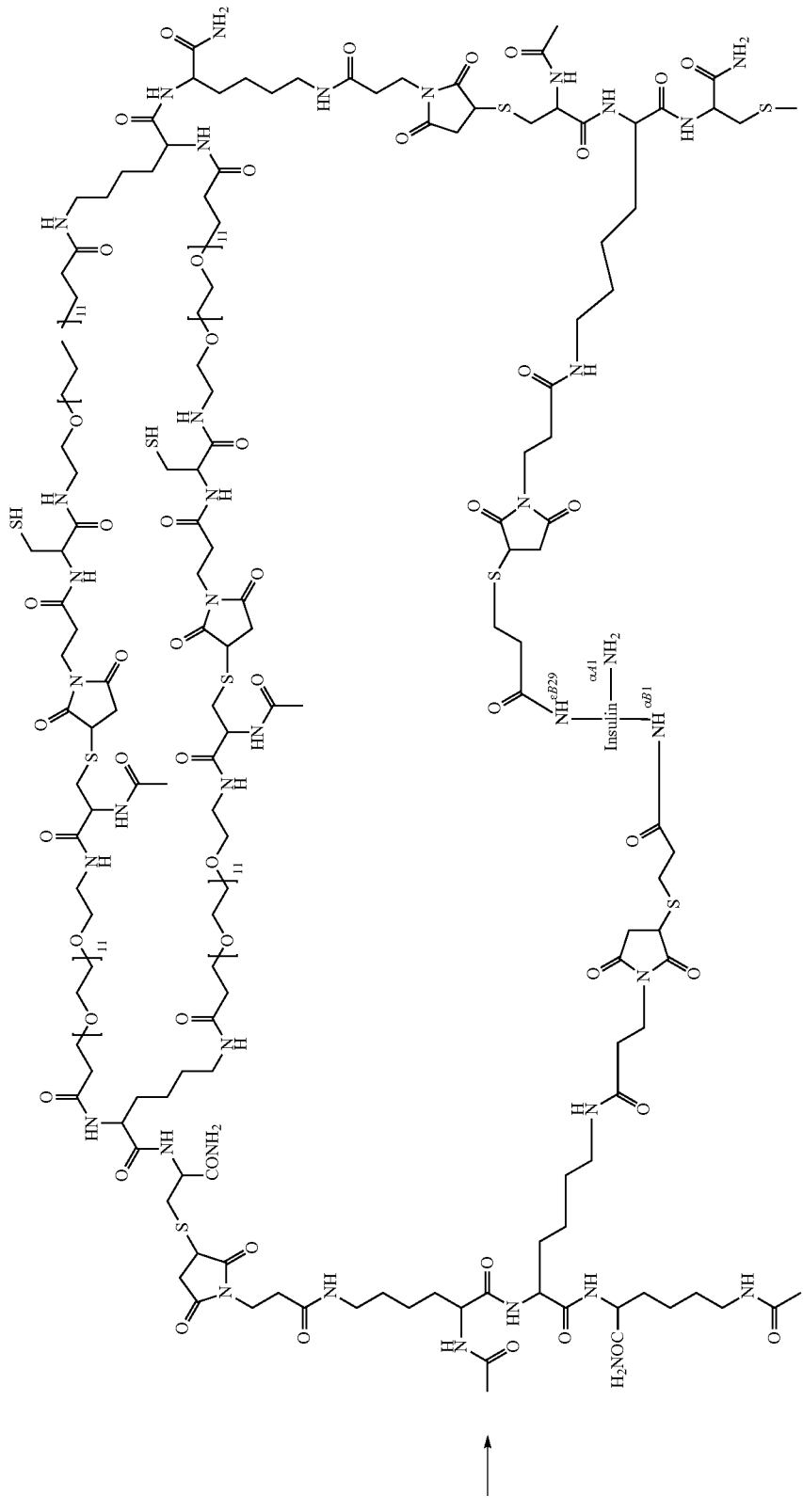

-continued
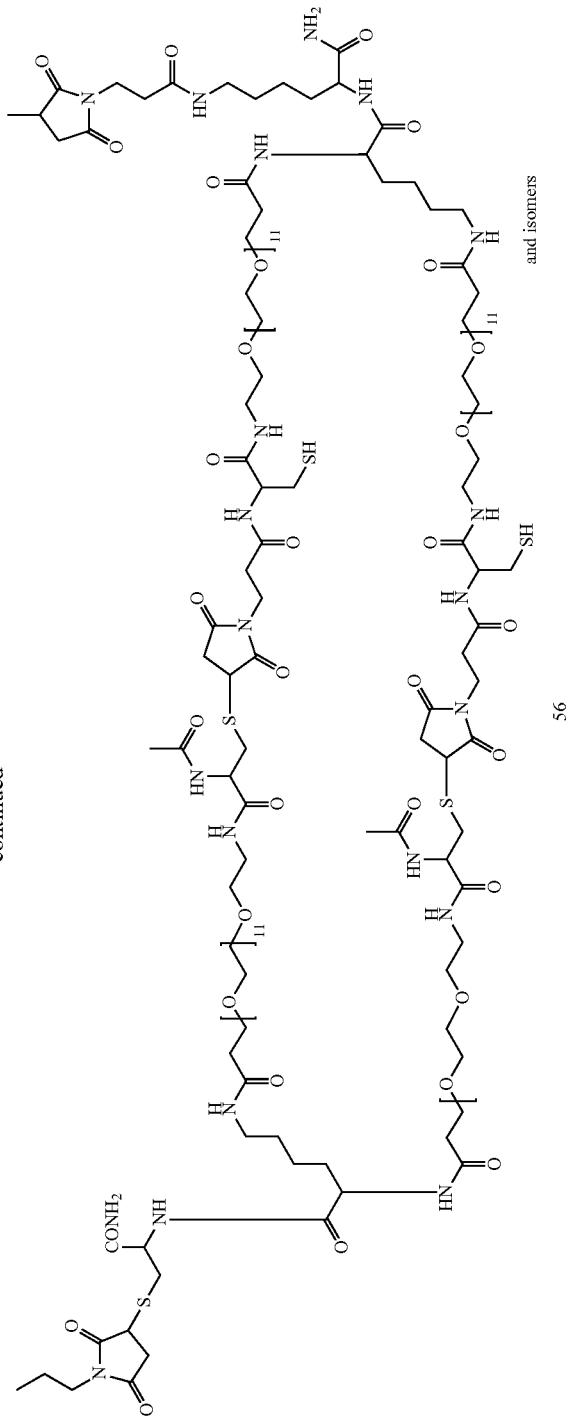
and isomers
56

Removal of Trt-protecting groups from compound 55 was effected by incubation for 30 min in 2/58/40 (v/v/v) TES/TFA/DCM. A two-step purification procedure employing RP-HPLC and SEC (Superdex 75, flow rate: 0.75 ml/min) yielded product 56.

MS (MW calculated) 56: 15167 g/mol (15166 g/mol)

VIII-3) Synthesis of Modified Insulin MPIC 57, 58 and 59

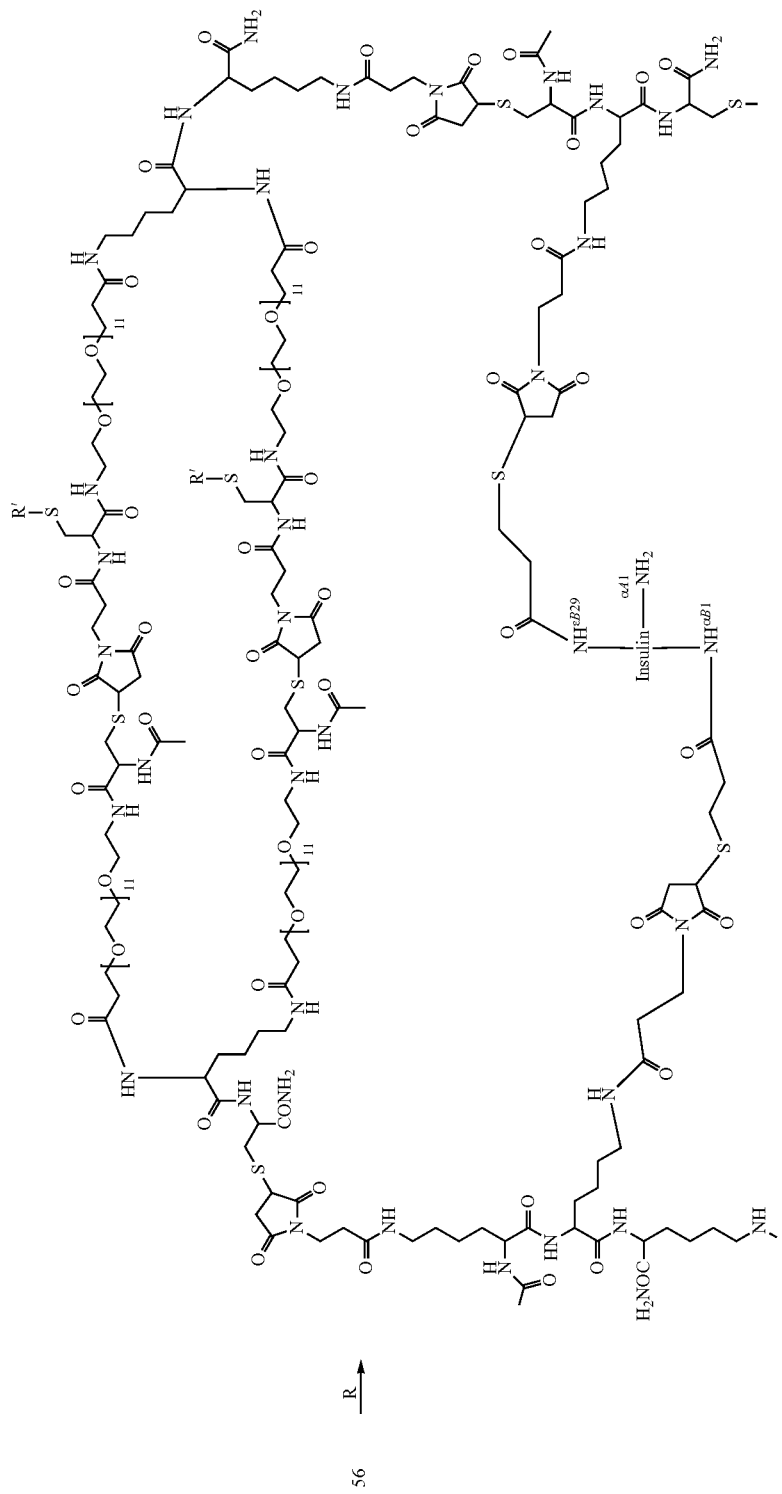

-continued
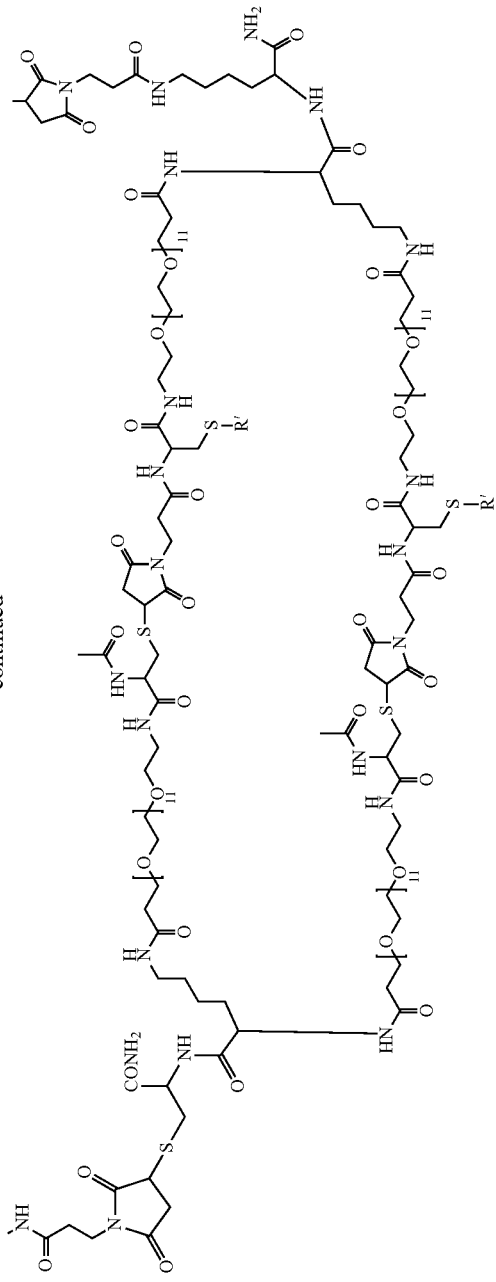
57: R = N-Ethyl-Maleimide
58: R = 38
59: R = 37
and isomers Structural element R represents the succinimidyl-containing product of the Michael addition of the neighboring proteophore thiol to the maleimido group of 37, 38 or N-ethyl maleimide, respectively. Aliquots (60 nmol) of compound 56 were reacted with 10 eq N-ethyl-maleimide, or 37 or 38, respectively, for 15 min in 500 μl 1/4 (v/v) acetonitrile/100 mM phosphate buffer (pH 8.0). Subsequent purification by SEC (Superdex 200, flow rate: 0.75 ml/min) yielded products 57, 58 or 59, respectively.

| Compound | Retention time |
|---|---|
| 57 | 20.8 min |
| 58 | 16.8 min |
| 59 | 13.5 min |

IX—Synthesis of Insulin MPIC 64 and 65

IX-1) Synthesis of $N^{\alpha B1},N^{\epsilon B29}$-bis-(thiollinker)-insulin 61

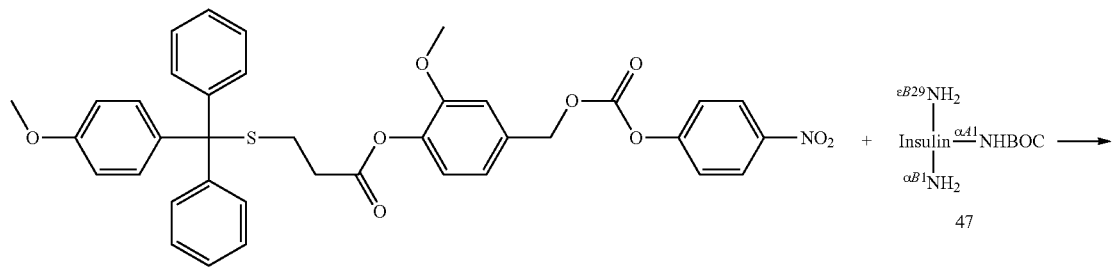

11

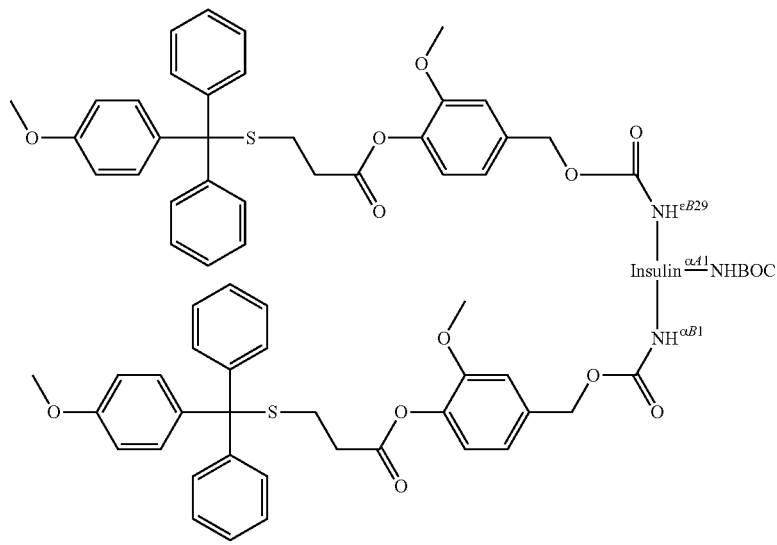

60

-continued

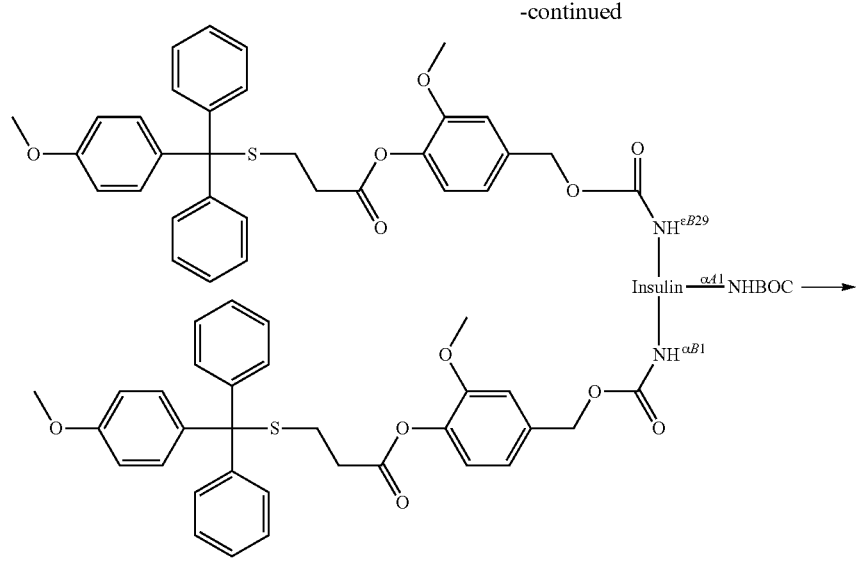

60

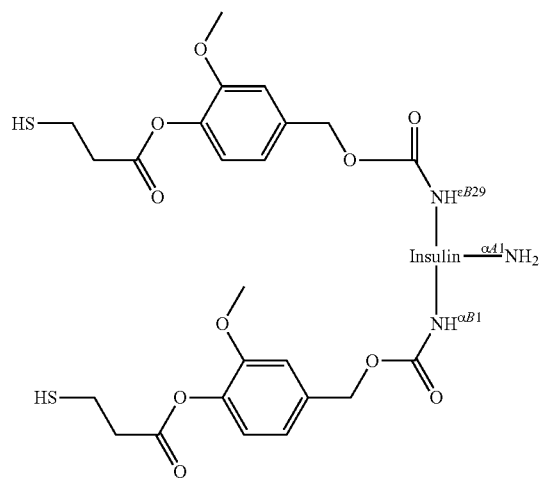

61

47 was mixed with 4 eq 11 in DMSO. The solution was adjusted to pH 8.0 by addition of DIEA and stirred for 2.5 h at RT under nitrogen atmosphere. RP-HPLC-purification and lyophilization gave compound 60.

MS (MW calculated) 60:6991 g/mol (6991 g/mol)

Removal of Trt-protection of 60 was afforded by stirring the compound in TFA/TES 95/5 (v/v) for 10 min at RT. The solution was dried under nitrogen flow. The residue was incubated for 30 min at RT in 1/1 TFA/DCM (v/v) and solvent was removed by a nitrogen flow. Product 61 was purified by RP-HPLC.

MS (MW calculated) 61: 6445 g/mol (6445 g/mol)

IX-2) Synthesis of Insulin MPIC 62

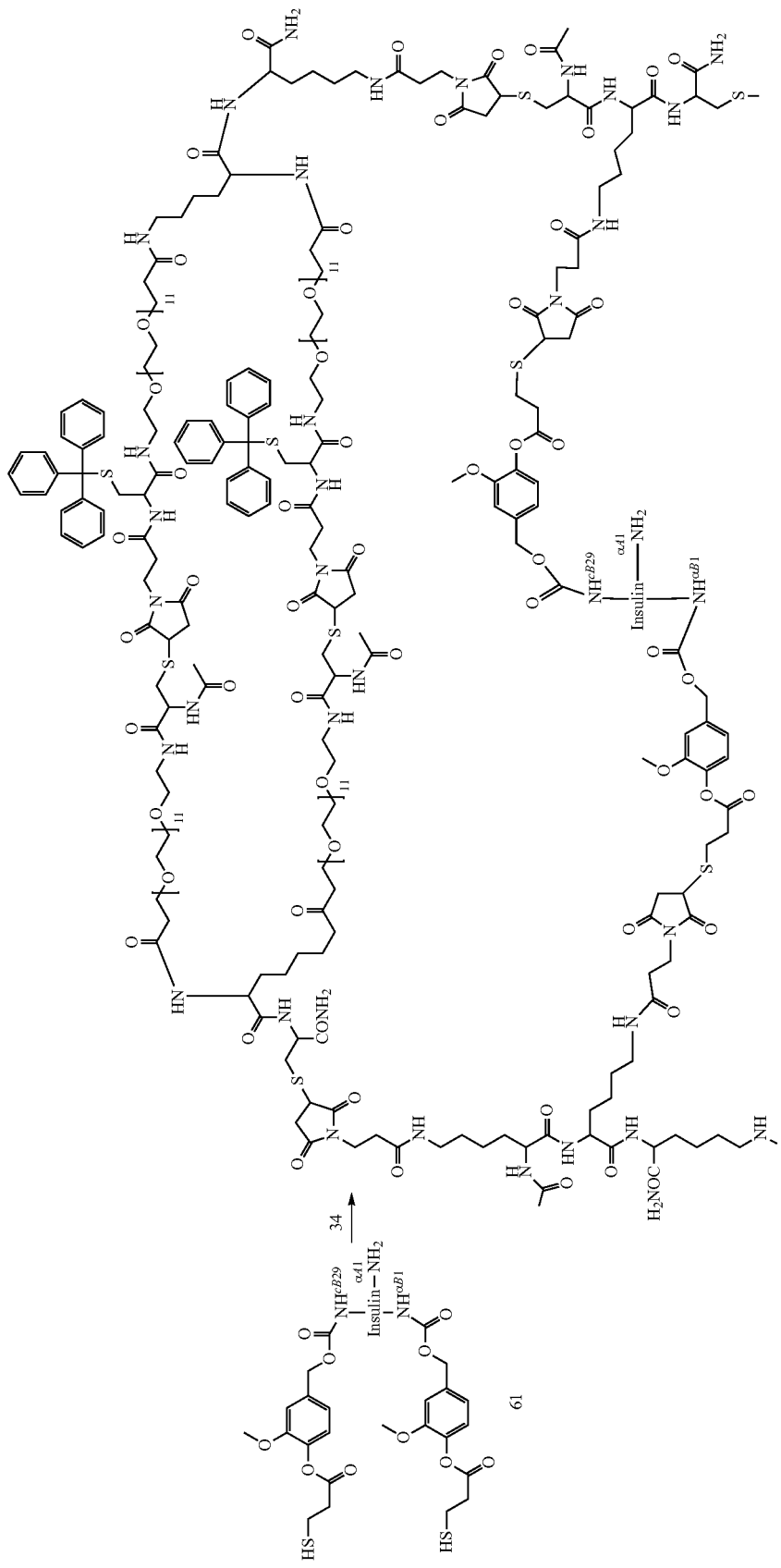

-continued
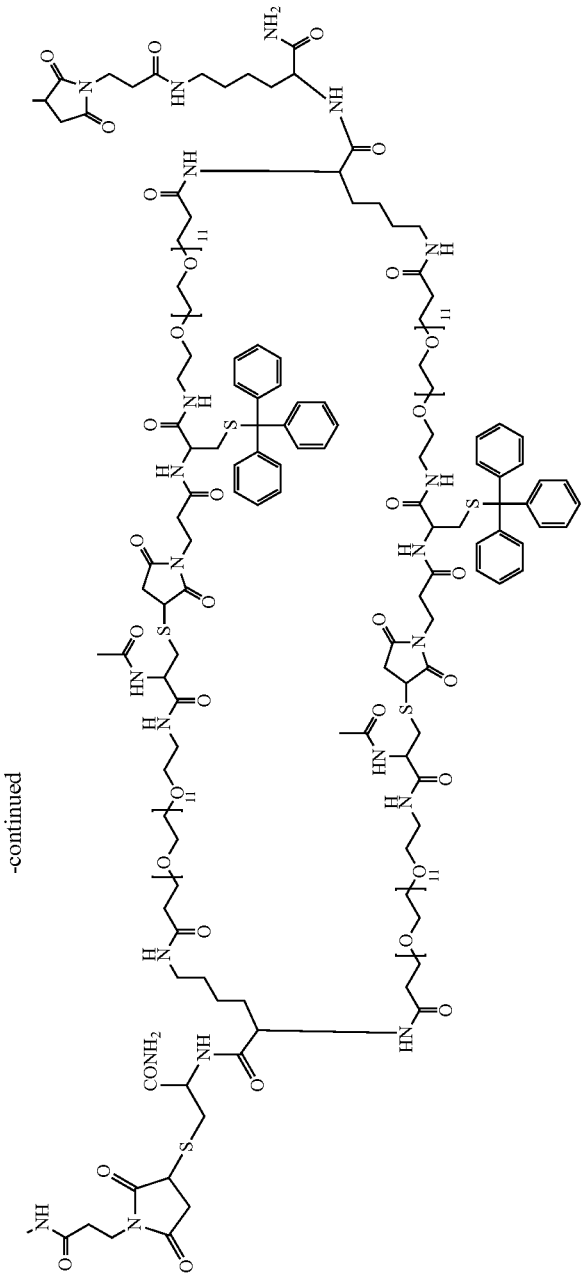
62 and isomers 1.8 ml of a solution of compound 61 (200 μM) in 1/1 (v/v) water/acetonitrile were mixed with 180 μl of a 1.5 mM solution of macrocyclic structure 34 in 1/1 (v/v) water/acetonitrile and diluted with 80/20 (v/v) water/acetonitrile to a total volume of 24 ml. Subsequently, the pH was adjusted to 7.5 by addition of 0.5 M phosphate buffer (pH 8.0). After incubating for 15 min, 62 was purified by RP-HPLC and lyophilized.

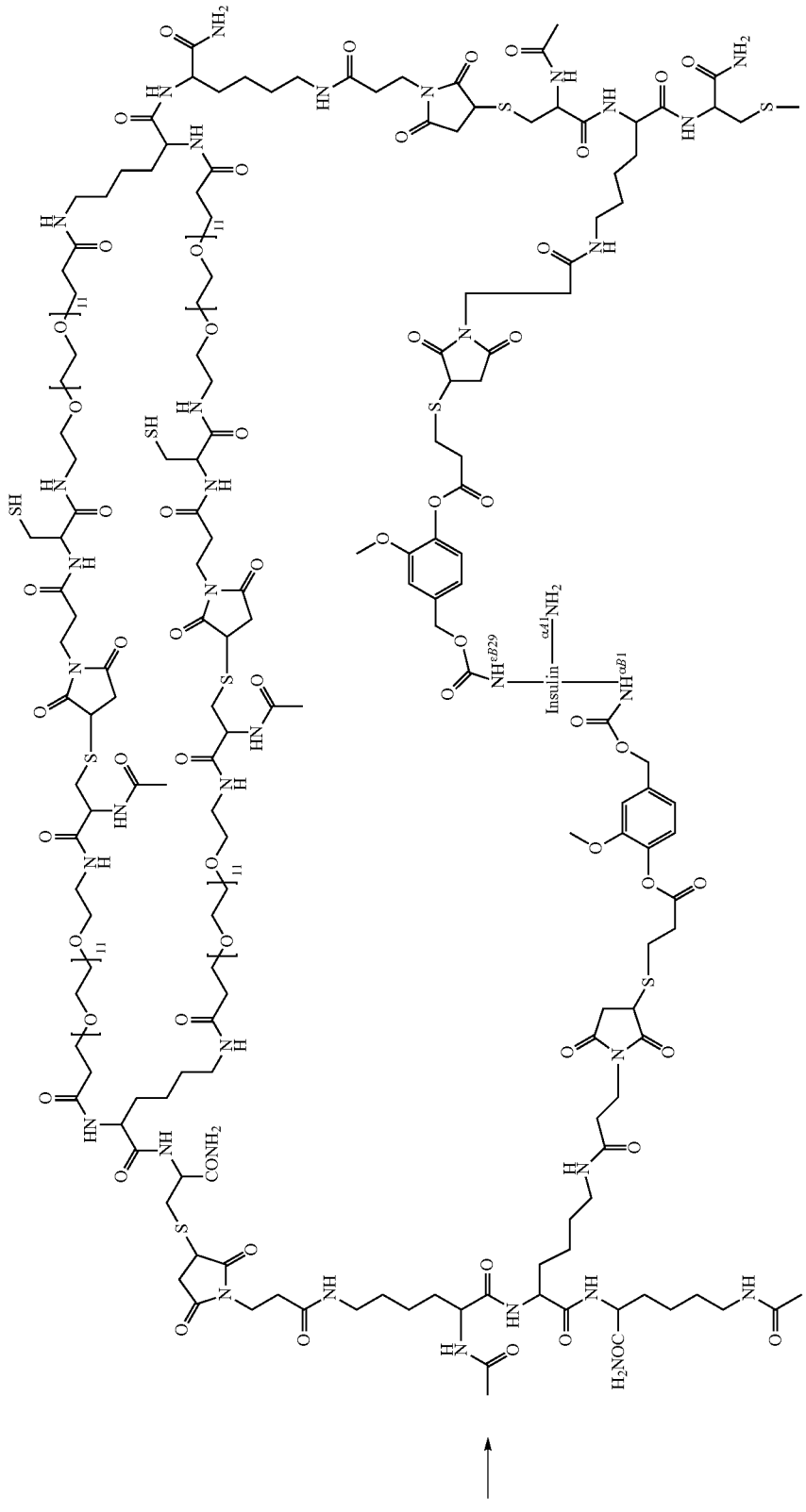

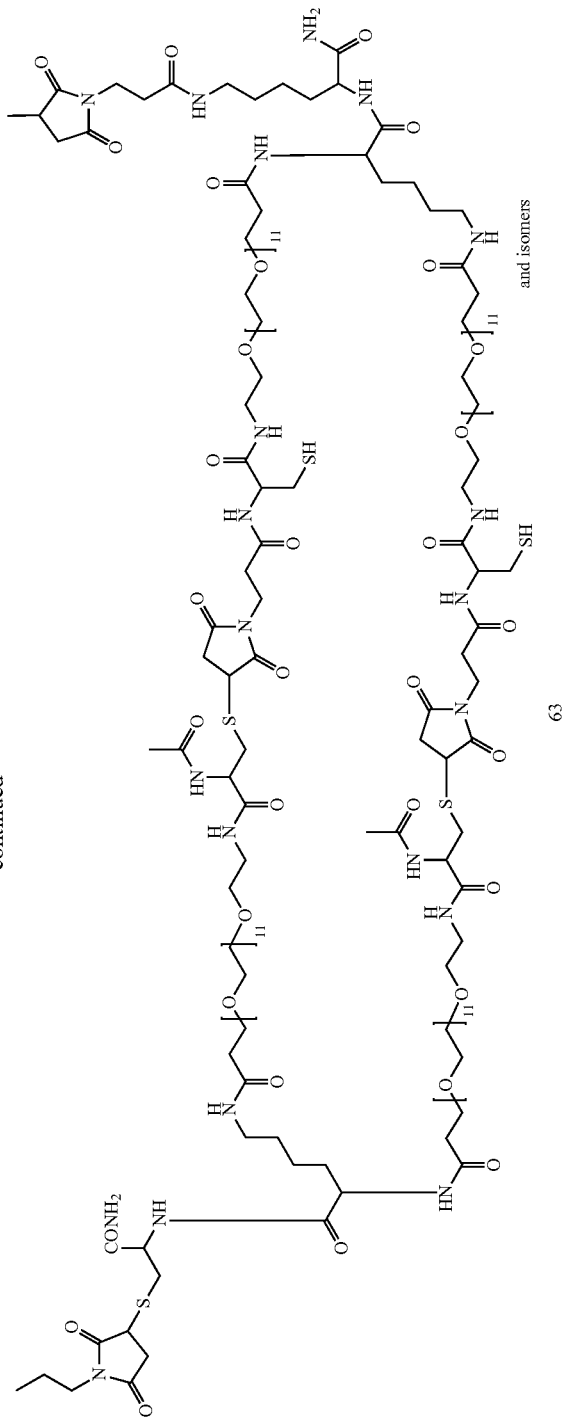

Detritylation of compound 62 was afforded by incubation for 30 min with 2/58/40 (v/v/v) TES/TFA/DCM. A two-step purification procedure employing RP-HPLC and SEC (Superdex 200, flow rate: 0.75 ml/min) yielded product 63.

MS (MW calculated) 63: 15518 g/mol (15526 g/mol)

IX-3) Synthesis of Modified Insulin MPIC 64 and 65

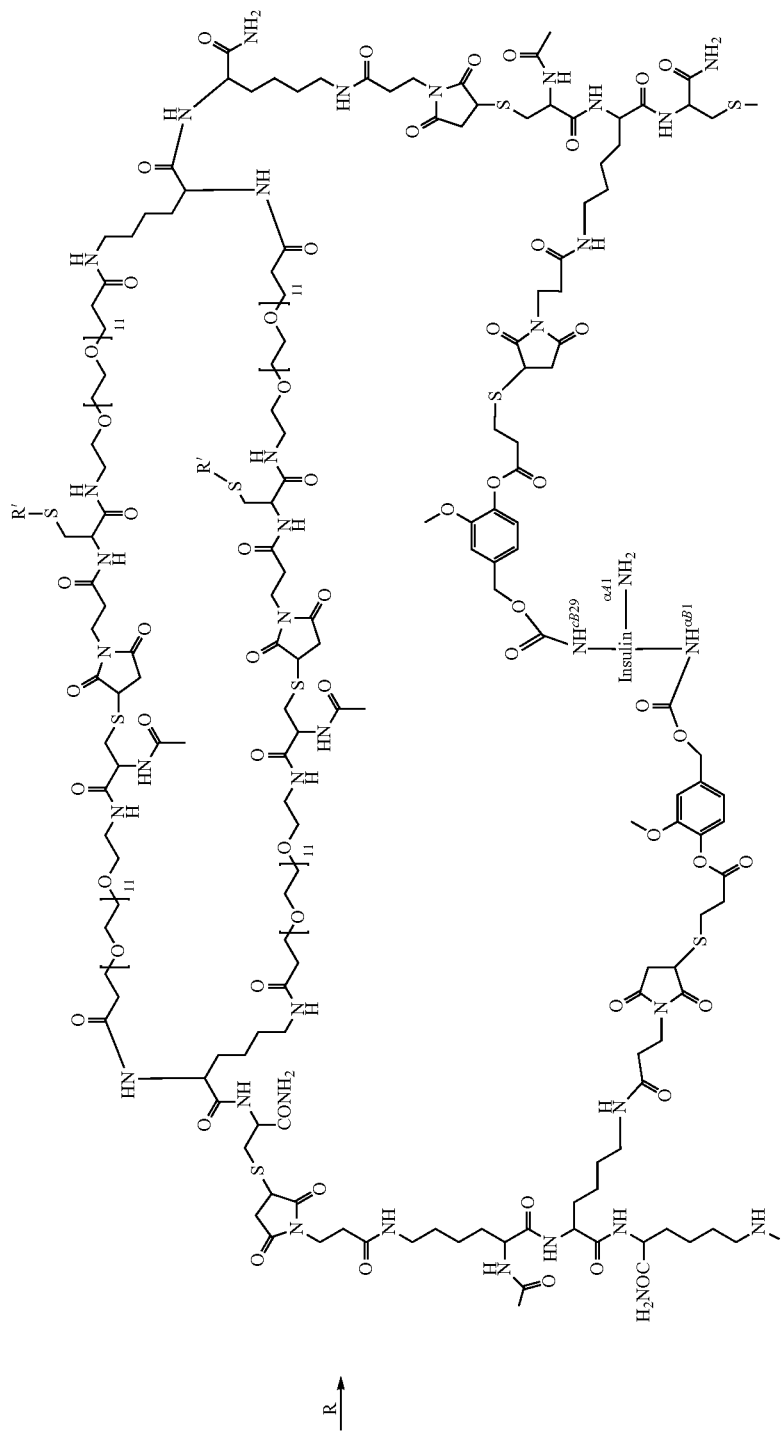

-continued
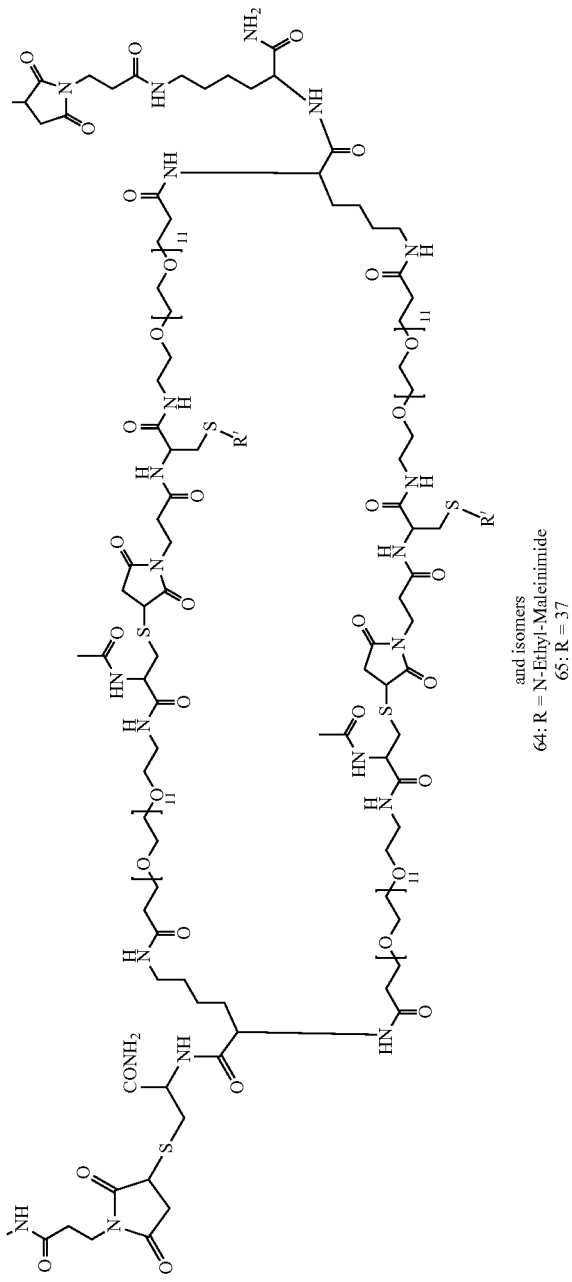
and isomers
64: R = N-Ethyl-Maleinimide
65: R = 37

Structural element R represents the succinimidyl-containing product of the Michael addition of the neighboring proteophore thiol to the maleimido group of compound 37 or N-ethyl-maleimide, respectively.

Aliquots (9 nmol) of compound 63 were incubated with 15 eq of N-ethyl-maleimide or 37, respectively, for 3 min in 70 µl 1/4(v/v) acetonitrile/phosphate buffer 100 mM (pH 7.5). Subsequent purification by SEC (Superdex 200, flow rate: 0.75 ml/min) gave products 64 or 65, respectively.

| Compound | Retention time |
|---|---|
| 64 | 20.2 min |
| 65 | 13.3 min |

IX-4) Release of Insulin from Insulin MPIC 64 and 65

Release of insulin from Insulin MPIC 64 or 65, respectively, was effected by linker hydrolysis in aqueous buffer. A ca. 10 µM solution of conjugate was incubated in 10 mM HEPES buffer (pH 7.4), 150 mM NaCl, 3 mM EDTA and 0.005% Tween. Samples were taken at time intervals and analyzed by HPLC and UV detection. The peak correlating with the retention time of native insulin was integrated and plotted against reaction time, and curve-fitting software was applied to estimate the corresponding halftime of release. Under these conditions, insulin was released from 64 with a halftime of approximately 150 min and from compound 65 with a halftime of ca 230 min.

X—Synthesis of Reference Insulin Conjugates 68-75

X-1) Synthesis of $N^{\epsilon B29}$-mercaptopropionyl-insulin 67

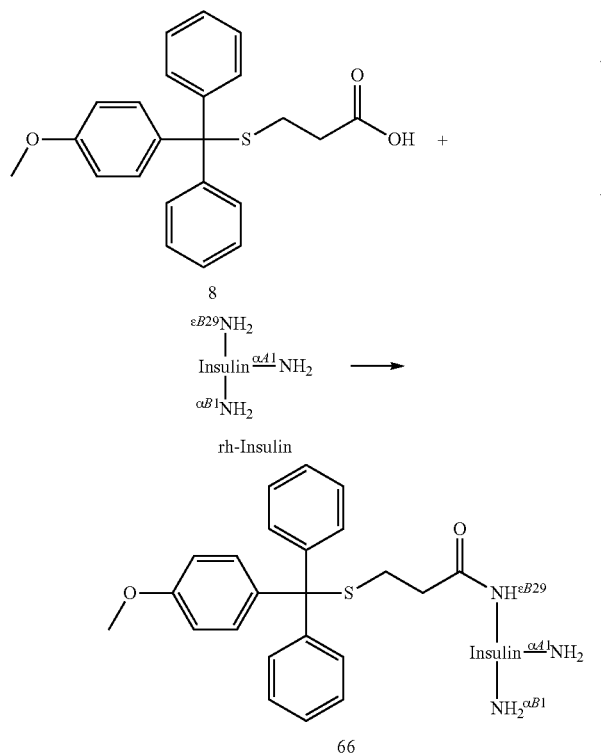

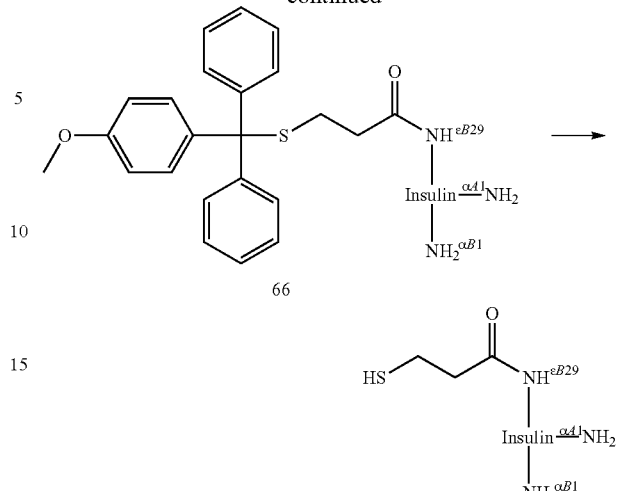

150 µl of a solution of 0.64 M DIC, 0.56 M 8 and 0.29 M N-hydroxy succinimide in DMF were prepared and incubated for 30 min. 18 mg insulin were dissolved in 1.6 ml 20/30/50 (v/v/v) DMSO/DMF/water and 50 µl DIEA were added, followed by addition of 50 µl of the preincubated cocktail containing compound 8. After incubation for 30 min another 100 µl of preactivated 8 were added. After incubation for 30 min product 66 was purified by RP-HPLC. Acetonitrile was removed in vacuo and cleavage of the Mmt-protecting group was afforded by addition of 98/2 (v/v) TFA/TES until an intensive yellow colour was observed. Product 67 was obtained by RP-HPLC purification.

MS (MW calculated) 67: 5893 g/mol (5896 g/mol)

X-2) Synthesis of Mono- and Bis-Pegylated Insulin Compounds 68-75

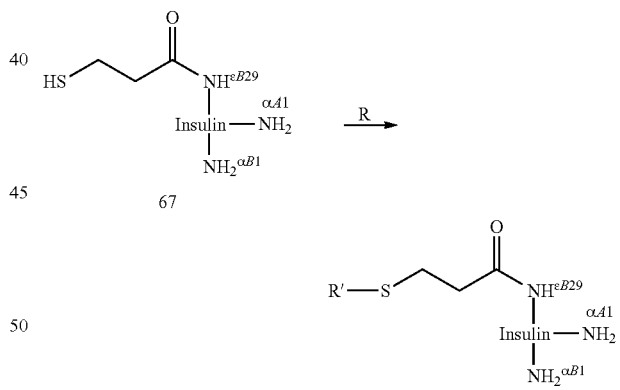

68: R = N-ethyl-maleimide
69: R = Maleimide-PEG5k
70: R = 37
71: R = Maleimide-PEG20k
72: R = Maleimde-PEG2x20k

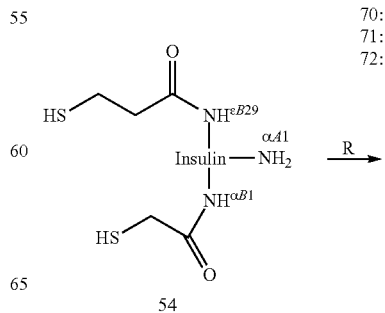

-continued

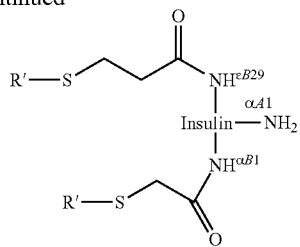

73: R = N-ethyl-maleimide
74: R = Maleimide-PEG5k
75: R = Maleimide-PEG20k

Structural element R represents the succinimidyl-containing product of the Michael addition of a thiol to the maleimido group of compound 37, N-ethyl-maleimide, Maleimide-PEG5k, Maleimide-PEG20k or Maleimide-PEG2×20k, respectively. Thiols are associated with the modified insulins 54 or 67, respectively.

71 µl of a solution of 67 (464 µM) in 1/4 (v/v) acetonitrile/water were incubated with 3.3 µl of N-ethyl maleimide (100 mM, 5 eq) in 1/1 (v/v) acetonitrile/water and 10 µl 10.5 M phosphate buffer (pH 8.0) for 3 min. Purification of compound 68 was afforded by SEC (Superdex 200).

71 µl of a solution of 67 (464 µM) in 1/4 (v/v) acetonitrile/water were mixed with 7 µl of a solution of 10 mM Maleimide-PEG5k (1 eq) in 1/4 (v/v) acetonitrile/water and 10 µl of 0.5 M phosphate buffer (pH 8.0) and incubated for 15 min. Compound 69 was purified by SEC (Superdex 200).

Compounds 70 and 71 were obtained according to the procedure used for the conjugation of 69 to 37 or Maleimide-PEG20k, respectively.

43 µl of a solution of 67 (464 µM) in 1/4 (v/v) acetonitrile/water were mixed with 22 µl of a solution of 2 mM Maleimide-PEG2×20k (2 eq) in 1/4 (v/v) acetonitrile/water and 10 µl of 0.5 M phosphate buffer (pH 8.0) and incubated for 15 min Compound 72 was purified by SEC (Superdex 200).

11.4 µl of a solution of 54 (2.9 mM) in 1/4 (v/v) acetonitrile/water were mixed with 50 µl 1/1 (v/v) acetonitrile/water, 7 µl of a 100 mM solution of N-ethyl maleimide (10 eq) and 10 µl of 0.5 M phosphate buffer (pH 8.0) and incubated for 3 min. Compound 73 was purified by SEC (Superdex 200).

11.4 µl of a solution of 54 (2.9 mM) in 1/4 (v/v) acetonitrile/water were mixed with 50 µl 1/1 (v/v) acetonitrile/water, 15 µl of a 10 mM solution of Maleimide-PEG5k (2 eq) in 1/4 (v/v) acetonitrile/water and 10 µl of 0.5 M phosphate buffer (pH 8.0) and incubated for 15 min. Compound 74 was purified by SEC (Superdex 200, flow rate: 0.75 ml/min). Compound 75 was obtained accordingly through reaction of 74 with Maleimide-PEG20k.

Preparative SEC of compounds 68-75 yielded fractions of 1.4-2.2 ml. Concentrations were determined by measuring UV extinction at 275 nm, assuming an average coefficient of extinction of $\epsilon_{275}=7500$.

| Compound | $E_{275}$/mOD | Concentration/µMol | Retention time/min |
| --- | --- | --- | --- |
| 68 | 97 | 12.9 | 23.0 |
| 69 | 102 | 13.6 | 18.8 |
| 70 | 33 | 4.4 | 16.1 |
| 71 | 60 | 8.0 | 15.9 |
| 72 | 38 | 5.0 | 14.3 |
| 73 | 100 | 13.3 | 23.3 |
| 74 | 75 | 10.0 | 17.8 |
| 75 | 59 | 7.9 | 14.1 |

XI) Synthesis of Insulin DPICs

XI-1) Synthesis of Dendron Building Block 77

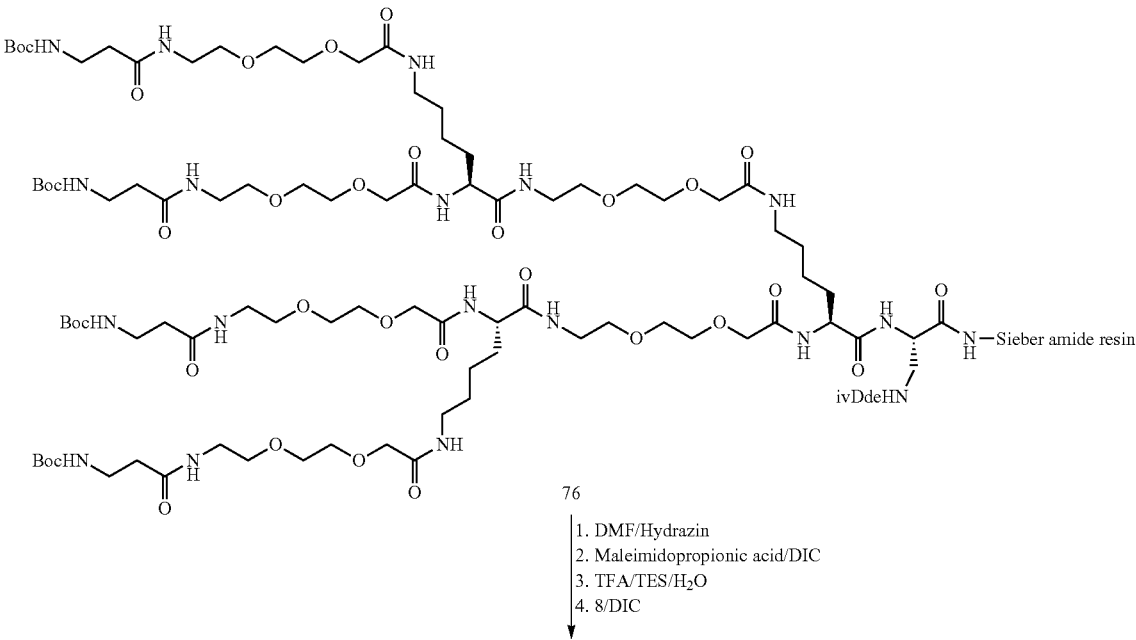

1. DMF/Hydrazin
2. Maleimidopropionic acid/DIC
3. TFA/TES/H₂O
4. 8/DIC

-continued

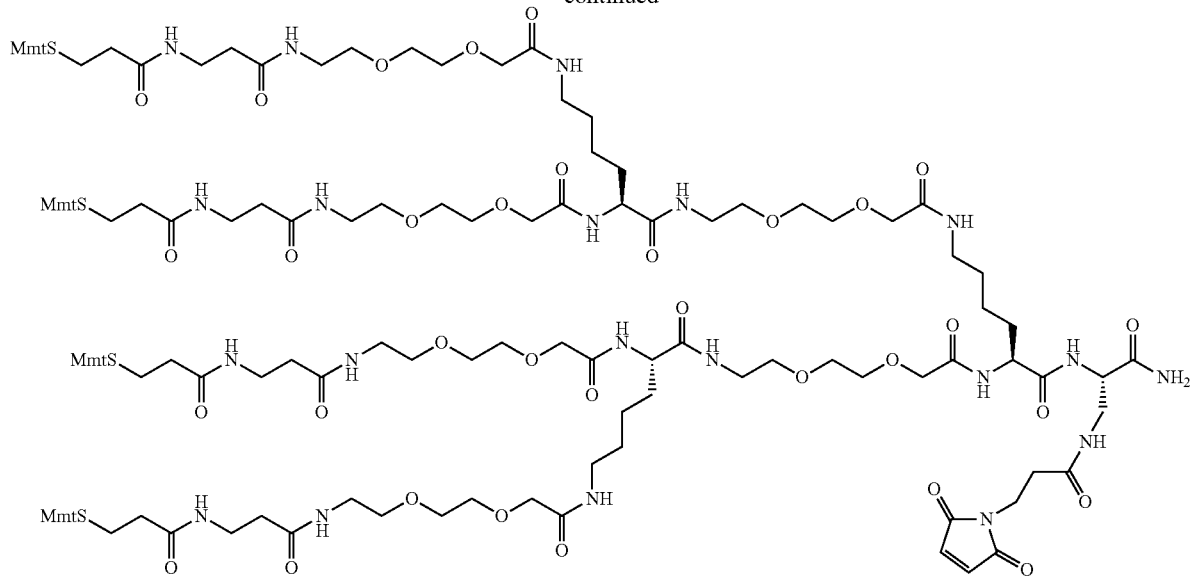

77

76 was obtained according to the standard solid-phase synthesis protocol. The amino acid sequence Fmoc-Dpr(ivDde)-OH, Fmoc-Lys(Fmoc)-OH, Fmoc-Ado-OH, Fmoc-Lys(Fmoc)-OH, Fmoc-Ado-OH and Boc-βAla-OH were coupled to Sieber amide resin.

Resin was treated with DMF/hydrazine 98/2 (v/v), washed and agitated with 5 eq maleimidopropionic acid and 5 eq DIC in DMF for 30 min. Product was cleaved from resin with TFA/TES/water 95/3/2 (v/v/v). After evaporation of solvent, the residue was taken up in 3/1 (v/v) DMF/collidine and reacted for 30 min with a solution of 15 eq 8 preactivated for 15 min with 10 eq DIC in DMF. After acidification with acetic acid, product 77 was purified by RP-HPLC.

MS (MW calculated) 77: 3233.7 g/mol (3236.0 g/mol).

XI-2) Synthesis of Insulin Dendrimers 78, 79 and 80

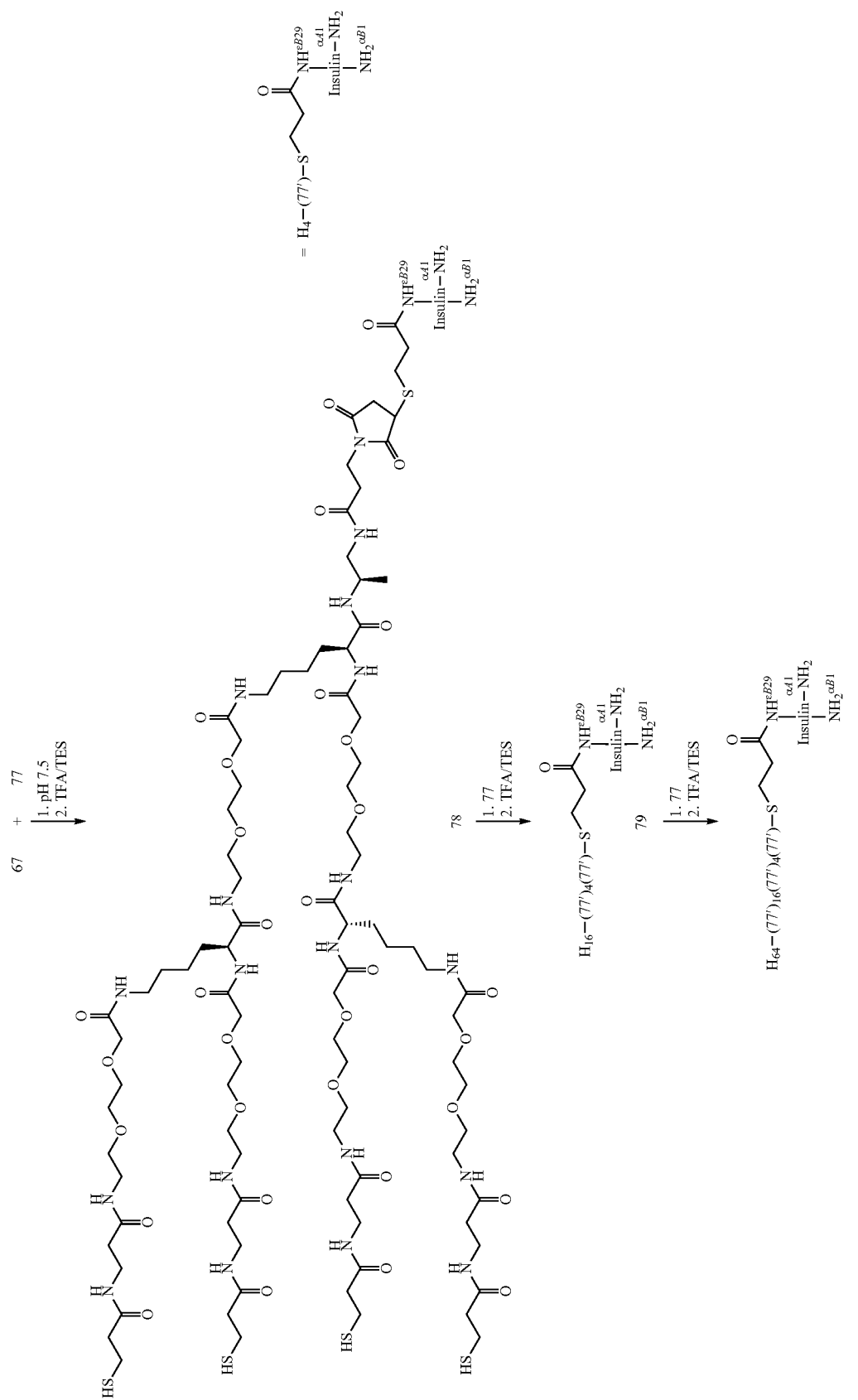

Structural element 77' represents the succinimidyl-containing product of the Michael addition of a thiol group to the maleimido group of compound 77 after Mmt protecting group removal. Thiol groups are either associated with the insulin-linker conjugate or with a dendron-insulin conjugate.

XI-2-1) Synthesis of 1st Generation Insulin-$N^{\epsilon B29}$-Mpa-Dendrimer (78)

2.9 mg 67 were dissolved in 100 µl acetonitrile/water and mixed with 180 µl of a solution of 77 (3.4 mM) in 4/1 acetonitrile/water. 20 µl of 0.5 M phosphate buffer (pH 7.5) were added and the solution was treated for 30 min with in an ultrasonic bath. The cocktail was mixed with 300 µl 1 TFA and 10 µl TES agitated for 30 s. After dilution with 1/1 acetonitrile/water, compound 78 was purified by RP-HPLC. Yield: 43%.

MS (MW calculated) 78: 8035 g/mol (8042 g/mol).

XI-2-2) Synthesis of 2nd Generation Insulin-$N^{\epsilon B29}$-Mpa-Dendrimer (79)

350 µl of a solution of 78 (420 µM) in 4/1 acetonitrile/water were mixed with 150 µl of a 5.2 mM solution of dendron 77 in 4/1 acetonitrile/water. 20 µl of 0.5 M phosphate buffer (pH 7.5) were added and the solution was treated for 30 min in an ultrasonic bath. The cocktail was mixed with 500 µl TFA and 20 µl TES and agitated for 30 s. After dilution with 1/1 acetonitrile/water, compound 79 was purified by RP-HPLC.

Yield: 40%

MS (MW calculated) 79: 16621 g/mol (16622 g/mol).

XI-2-3) Synthesis of 3rd Generation Insulin-$N^{\epsilon B29}$-Mpa-Dendrimer (80)

46 µl of a solution of 79 (235 µM) in 4/1 acetonitrile/water were mixed with 60 µl of a 5.2 mM solution of dendron 77 in 4/1 acetonitrile/water. 20 µl of 0.5 M phosphate buffer (pH 7.5) were added and the solution was treated for 30 min in an ultrasonic bath. The cocktail was mixed with 100 µl TFA and 5 µl TES and agitated for 30 s. After dilution with 1/1 water/acetonitrile compound 80 was purified by HPLC.

Yield: 38%

MS (MW calculated) 80: 50967 g/mol (50967 g/mol).

X-3) Synthesis of End-Capped Dendrimers 81, 82, 83 and 84 Based on 2nd Generation Insulin-$N^{\epsilon B29}$-Mpa-Dendrimer

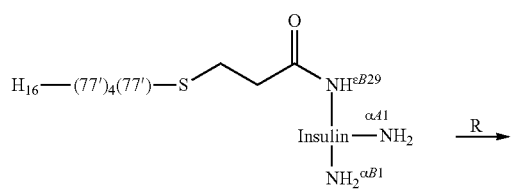

79

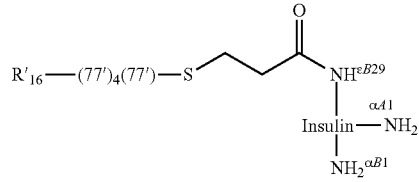

81: R = N-Ethylmalemide
82: R = 38
83: R = Maleimide-PEG5k
84: R = 37

Structural element R represents the succinimidyl-containing product of the Michael addition of a thiol group of 77' to the maleimido group of compound 37, 38, N-ethyl-maleimide, or Maleimide-PEG5k, respectively.

XI-3-1) Synthesis of 81

70 µl of a solution of 79 (230 µM) in 1/1 acetonitrile/water were mixed with 10 µl of a 24 mM solution of N-ethyl-maleimide in acetonitrile. pH was adjusted to 7.5 with 0.5 M phosphate buffer (pH 7.5) and the solution was incubated for 30 min at RT. Purification by SEC (Superdex 200, flow rate: 0.75 ml/min) gave compound 81.

SEC (retention time) 81: 20.28 min
MS (MW calculated) 81: 18629 g/mol (18624 g/mol)

XI-3-2) Synthesis of 82

70 µl of a solution of 79 (230 µM) in 1/1 acetonitrile/water were mixed with 3 mg 38. The pH was adjusted to 7.5 with 0.5 M phosphate buffer (pH 7.5) and the solution was incubated for 30 min at RT. Purification by SEC (Superdex 200, flow rate: 0.75 ml/min) yielded compound 82.

SEC (retention time) 82: 14 5 min

XI-3-3) Synthesis of 83

70 µl of a solution of 79 (230 µM) in 1/1 acetonitrile/water were mixed with 2.6 mg Maleimide-PEG5k. The pH was adjusted to 7.5 with 0.5 M phosphate buffer (pH 7.5) and the solution was incubated for 30 min at RT. Purification by SEC (Superdex 200, flow rate: 0.75 ml/min) gave compound 83.

SEC (retention time) 83: 12.9 min

XI-3-4) Synthesis of 84

115 µl of a solution of 79 (65 µM) in 1/1 acetonitrile/water were mixed with 5 mg 37. The pH was adjusted to 7.5 with 0.5 M phosphate buffer (pH 7.5) and the solution was incubated for 30 min at RT. Purification by SEC (Superdex 200, flow rate: 0.75 ml/min) gave compound 84.

SEC (retention time) 84: 10.9 min

XI-4) Synthesis of Cleavable Insulin Dendrimeres 87, 88, and 89

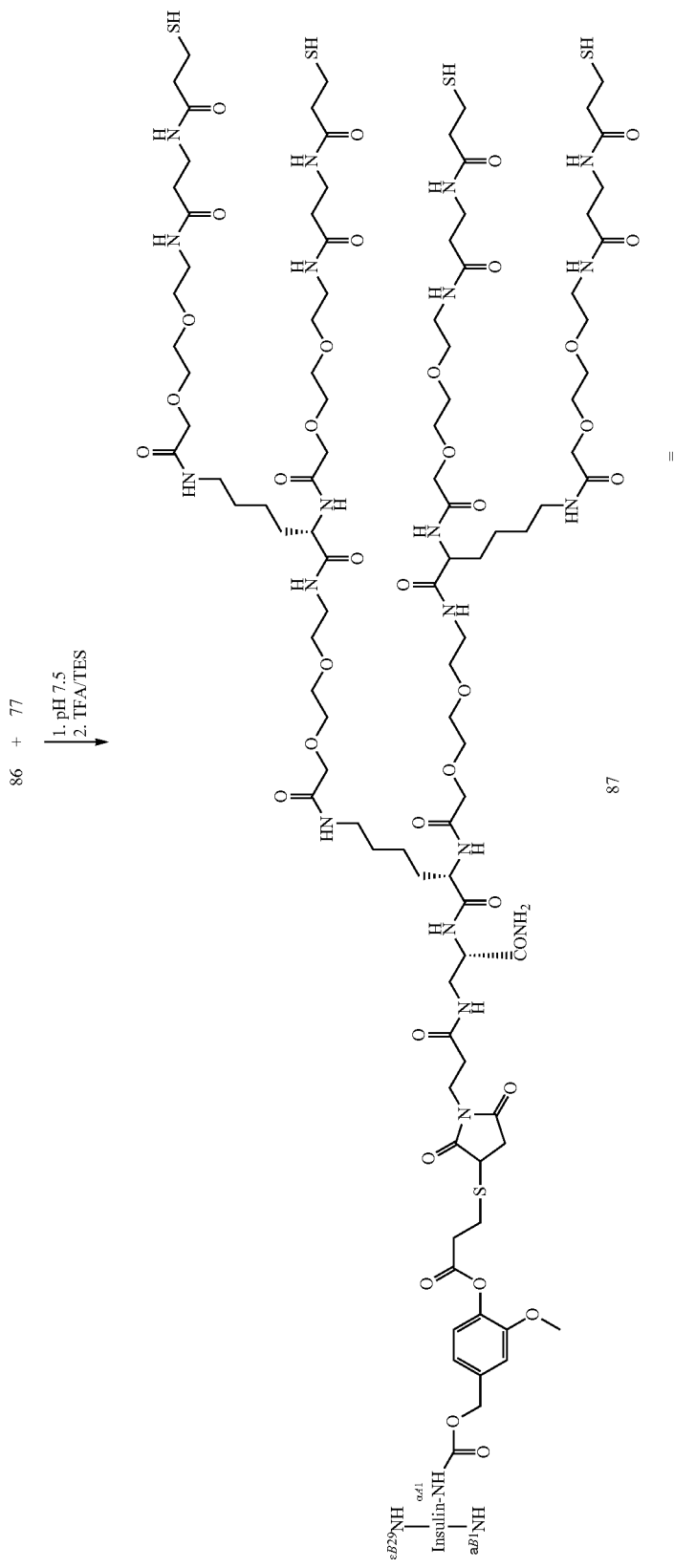

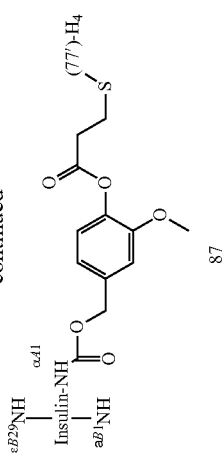
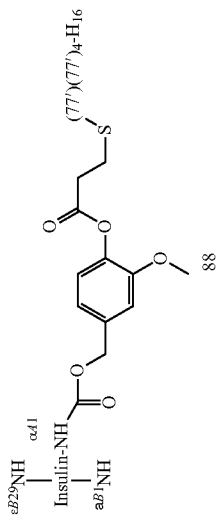
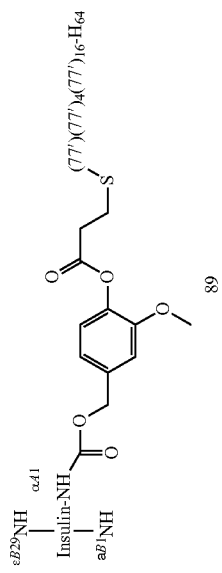

Structural element 77' represents the succinimidyl-containing product of the Michael addition of a thiol group to the maleimido group of compound 77 after Mmt protecting group removal.

Thiol groups are either associated with the insulin-linker conjugate or with a dendron-insulin conjugate.

XI-4-1) Synthesis of $N^{\alpha A1}$-Thiollinker-Insulin 86

XI-4-2) Synthesis of 1st Generation $N^{\alpha A1}$-Thiol-linker-Insulin-Dendrimer 87

Synthesis of compound 87 was performed in analogy to the synthesis of compound 78.

Yield: 27%

MS (MW calculated) 87: 8218 g/mol (8223 g/mol).

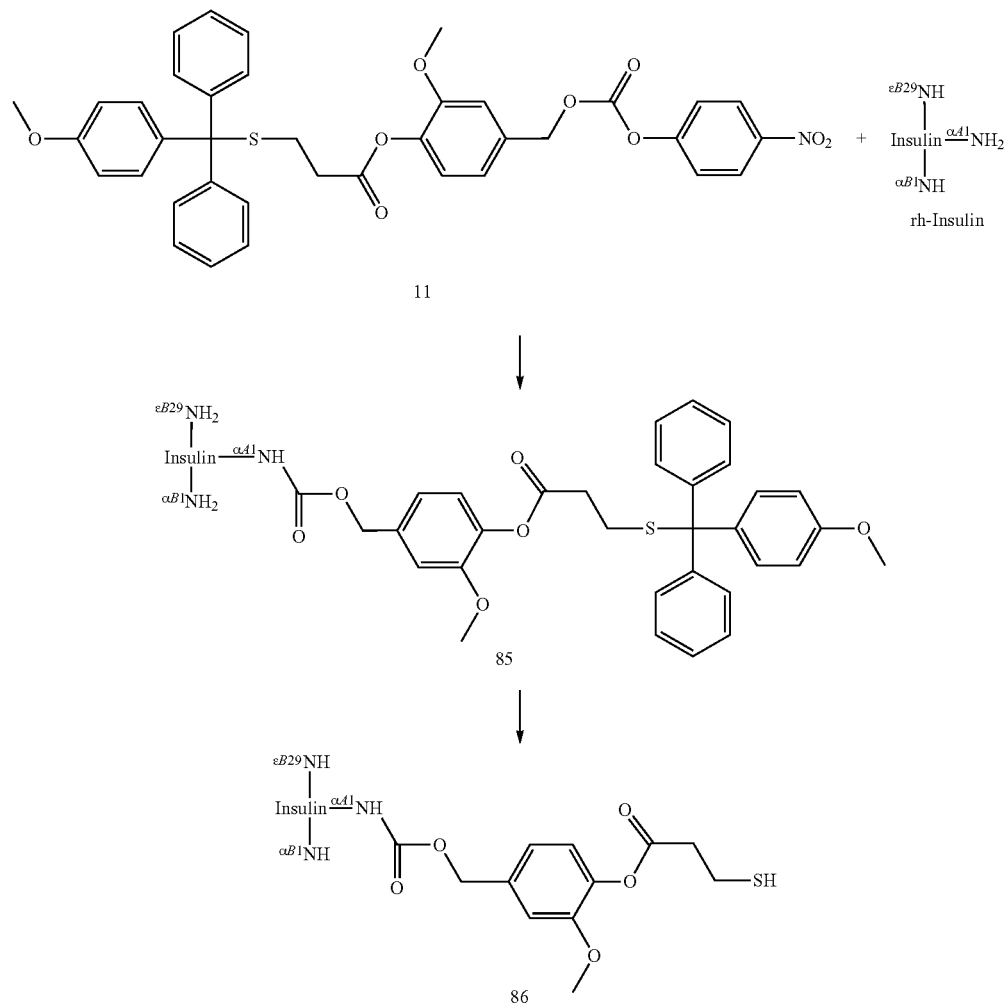

Insulin in DMSO was mixed with a solution of 0.9 eq 11 in DMSO. The resulting solution was adjusted to pH 8.0 with DIEA and stirred for 1.5 h at RT. RP-HPLC purification gave Mmt-protected intermediate 85.

MS (MW calculated) 85:6350 g/mol (6350 g/mol)

Regioselectivity of the monoconjugation was determined by reduction of 85 with DTT (10 mM) in 0.5 M phosphate buffer pH 8.0 for 1 h at RT and subsequent analysis of the insulin A- and B-chains by LC-MS.

After lyophilization, compound 85 was mixed with 95:5 (v/v) TFA/triethylsilane and stirred for 5 min. Volatiles were removed under nitrogen flow and 86 was purified by RP-HPLC and lyophilized.

MS (MW calculated) 86: 6077 g/mol (6077 g/mol)

XI-4-3) Synthesis of 2nd Generation $N^{\alpha A1}$-Thiol-linker-Insulin-dendrimer 88

Synthesis of compound 88 was performed in analogy to the synthesis of compound 79.

Yield: 17%

MS (MW calculated) 88: 16809 g/mol (16809 g/mol).

XI-4-4) Synthesis of 3rd Generation $N^{\alpha A1}$-Thiol-linker-Insulin-Dendrimer 89

Synthesis of compound 89 was performed in analogy to the synthesis of compound 80.

Yield: 44%

MS (MW calculated) 89: 51117 g/mol (51155 g/mol).

XI-5) Synthesis of End-Capped Dendrimers 90 and 91 Based on 1st or 2nd Generation $N^{\alpha 41}$-Thiol-linker-Insulin-Dendrimers

XI-5-1) Synthesis of 90

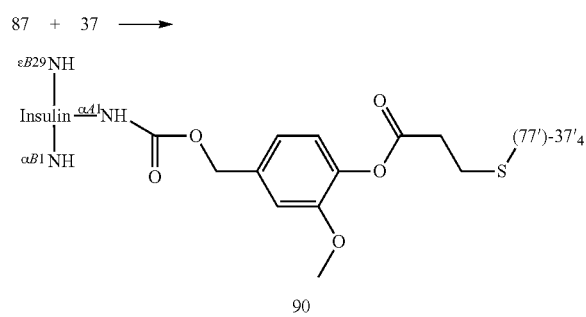

Structural element 37' represents the succinimidyl-containing product of the Michael addition of a thiol group to the maleimido group of compound 37. Thiol groups are associated with a generation 1 dendron-insulin conjugate.

50 µl of a solution of 87 (450 µM) in 1/1 acetonitrile/water were mixed with 3.5 mg of 37. The pH was adjusted to 7.5 with 0.5 M phosphate buffer (pH 7.5) and the solution was incubated for 30 min at RT. Purification by SEC (Superdex 200, flow rate 0.75 ml/min) gave compound 90.

SEC (retention time) 90: 13.0 min

XI-5-2) Synthesis of 91

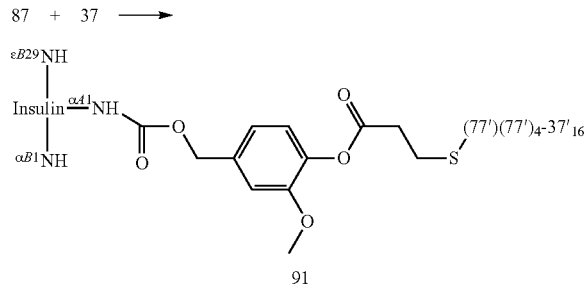

Structural element 37' represents the succinimidyl-containing product of the Michael addition of a thiol group to the maleimido group of compound 37. Thiol groups are associated with a generation 2 dendron-insulin conjugate.

75 µl of a solution of 88 (206 µM) in 1/1 acetonitrile/water were mixed with 9 mg of 37. The pH of the solution was adjusted to 7.5 with 0.5 M phosphate buffer (pH 7.5) and the solution was incubated for 30 min at RT. Purification by SEC (Superdex 200, flow rate 0.75 ml/min) yielded compound 91.

SEC (retention time) 91: 10.9 min

XI-6) Release of insulin from insulin DPIC 90 and 91

Figure 5:
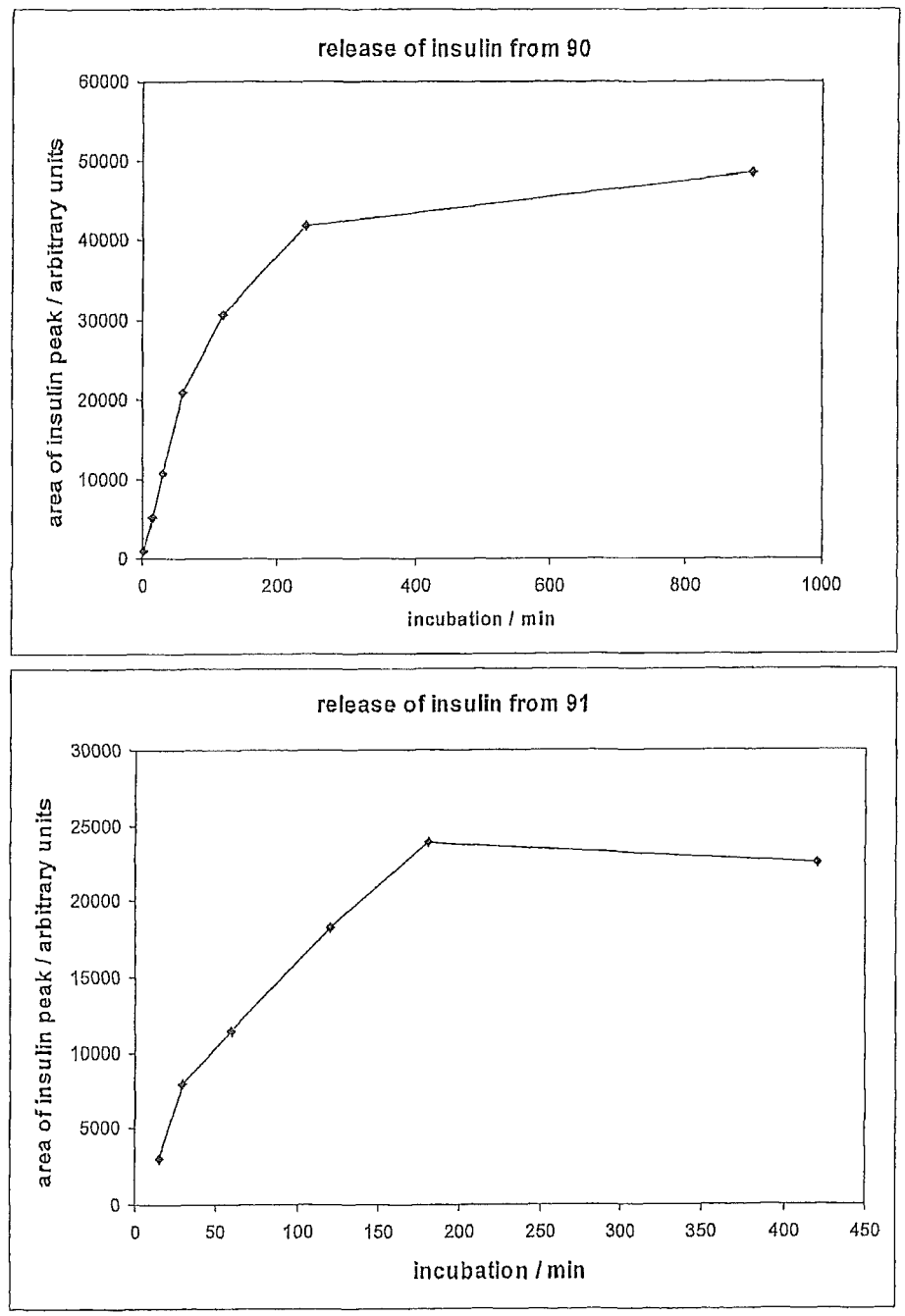
FIG. 5: Release of insulin from dendrimer prodrugs 90 (top) and 91 (below). Free insulin was quantified by HPLC using UV detection at 215 nm.
Figure 6:
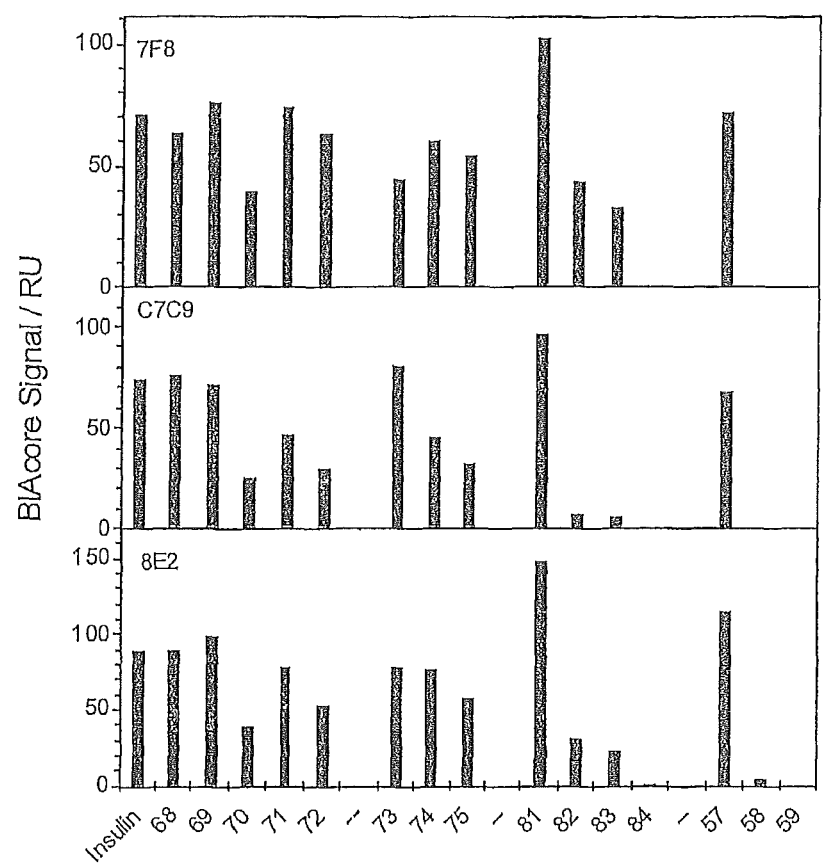
FIG. 6: Binding of insulin or insulin conjugates to immobilized murine anti insulin antibodies (clones 8E2, C7C9 and 7F8).

SEC-eluates of 90 and 91 were incubated with 10 mM HEPES buffer (pH 7.4), 150 mM NaCl, 3 mM EDTA and 0.005 Tween at 37° C., and the amount of free insulin was quantified by HPLC using UV detection at 215 nm (FIG. 5).

XII—Analysis of Efficiency of Encapsulation

Analysis was performed on a BIAcore 2000 surface plasmon resonance instrument using CM5 sensor chips (Biacore).

XII-1) Preparation of Sensor Chips

A sensor chip was mounted to the instrument and RAMFc (rabbit anti mouse Fc antibody, BIAcore) was immobilized according to Karlsson et al. (J. Immun. Meth, 200, 1997, 121-133) using EDC/NHS activation. Capping of activated, unreacted surface carboxy groups was effected by ethanolamine.

XII-2) Interaction Analysis Between Proteophor-Encapsulated Insulin and Anti-Insulin Antibodies Insulin and insulin conjugates 68-75, 57-59 and 81-84 were subject to analysis.

For sample application, dissociation and regeneration, standard flow buffer was used containing 10 mM HEPES (pH 7.4), 150 mM NaCl, 3 mM EDTA, 0.005% Tween 20.

Three murine anti insulin monoclonal antibodies (Advanced ImmunoChemical Inc., clones C7C9, 8E2, or 7F8, respectively,) were loaded onto prespecified sensor chip areas by injection of 15 µl of a solution of 30 µg/ml. A fourth sensor area was used for reference purposes. After equilibration for 2.5 min, 150 µl of a 100 nM solution of insulin or insulin conjugate were injected and flowed across all four sensor areas. A dissociation phase of 3 min was followed by removal of the anti-insulins by injection of 60 µl glycine buffer (pH 2.0) and regeneration of the sensor chip surface. Encapsulation efficiency was measured by recording the refractive index units (RU) of each of the four sensor areas before dissociation.

Highly efficient encapsulation of insulin was achieved by conjugating the protein to proteophore structures 84, 58 or 59, respectively, as evidenced by suppression of antibody binding.

While there have been described what are presently believed to be the preferred embodiments of the invention, those skilled in the art will realize that changes and modifications may be made without departing from the spirit of the invention. It is intended to claim all such changes and modifications as fall within the true scope of the invention.

| Abbreviations: | |
|---|---|
| Boc | t-butyloxycarbonyl |
| DBU | 1,3-diazabicyclo[5.4.0]andecene |
| DCM | dichloromethane |
| (iv)Dde | 1-(4,4-dimethyl-2,6-dioxo-cyclohexyliden)3-methyl-butyl |
| DIC | diisopropylcarbodiimide |
| DIEA | diisopropylethylamine |
| DMAP | dimethylamino-pyridine |
| DMF | N,N-dimethylformamide |
| DMSO | dimethylsulfoxide |
| Dpr | diaminopropionic acid |
| DTT | dithiothreitol |
| EDC-HCl | 1-Ethyl-3-(3'-dimethylaminopropyl) carbodiimide hydrochloride |

Abbreviations:

| | |
|---|---|
| Endo-GluC | endoproteinase-GluC |
| eq | stoichiometric equivalent |
| Fmoc | 9-fluorenylmethoxycarbonyl |
| Fmoc-PP-OH | Fmoc-aminoethyl-undecaethyleneoxide-propionic acid |
| Fmoc-Ado-OH | Fmoc-8-amino-3,6-dioxaoctanoic acid |
| Hb | hemoglobin (human) |
| HEPES | N-(2-hydroxyethyl) piperazine-N'-(2-ethanesulfonic acid) |
| HOBT | N-hydroxybenzotriazole |
| LCMS | mass spectrometry-coupled liquid chromatography |
| Mal | maleimidopropionyl |
| Mmt | 4-methoxytrityl |
| Mpa | mercaptopropionyl |
| MS | mass spectrum |
| MSNT | 1-(mesitylen-2-sulfonyl)-3-nitro-1H-1,2,4-triazole |
| Mtt | 4-methyltrityl |
| MW | molecular mass |
| NHS | N-hydroxy succinimide |
| RP-HPLC | reversed-phase high pressure liquid chromatography |
| RT | room temperature |
| RU | response units |
| SEC | size exclusion chromatography |
| SPDP | succinimidyl 3-(2-pyridyldithio) propionate |
| S-tBu | t-butylthio |
| Suc | succinimidopropionyl |
| TBTU | O-(benzotriazol-1-yl)-N,N,N',N'-tetramethyluronium tetrafluoroborate |
| TCEP | tricarboxyethylphosphine |
| TES | triethylsilane |
| TFA | trifluoroacetic acid |
| THF | tetrahydrofurane |
| Trt | trityl, tiphenylmethyl |
| UV | ultraviolet |

The invention claimed is:

1. A composition comprising a hyperbranched polymer attached to a core and to a biologically active moiety; wherein the hyperbranched polymer contains at least two molecular chains, which molecular chains are of sufficient length to be so arranged as to form a cavity to accommodate the biologically active moiety, and wherein the molecular chains contain sterically demanding capping groups; further wherein the composition has the formula (V):

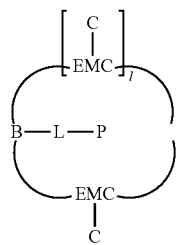
(V)

wherein:
(i) B is the core, containing at least one unit selected from the group consisting of >CH—, >C, and respective analogs thereof, wherein H is replaced by an organic group, >N—, or >P—;
(ii) each EMC is one of the at least two molecular chains and each comprises oxyethylene groups;
(iii) L is a non-enzymatically cleavable linker and comprises a carbamate group;
(iv) l is an integer selected from the group consisting of 1, 2, 3, 4, 5, 6, 7, 8, 9, 10, 11, and 12;
(v) P is the biologically active moiety and is a somatropin or insulin; and
(vi) C is one or more of the capping groups, which comprises linear, branched, or cyclical alkyl groups, and optionally containing S, N, or O heteroatoms.

2. The composition of claim 1, wherein the hyperbranched polymer is water soluble.

3. The composition of claim 1, wherein further groups are present in the polymer chains, the further groups being selected from the groups consisting of S, —N,O, ((—S—S)—, oxyethylene-oxypropylene and oxybutylene, amide —C(O)NH— or C(O)NR—, —S-succinimido, amino (—NR—), carboxylic ester (—C(O)O—), sulfonamide (—S(O)$_2$—NR—), carbamate (—O—C(O)—NR—), carbonate (—OC(O)—O—), sulfone (—S(O)$_2$—), ether (—O—), oxime (—CR=N—O—), hydrazone (—CR=N—NR—), urea (—NR—C(O)—NR—), thiourea (—NR—C(S)—NR—), carbohydrate, glyceryl, phosphate (—O—P(O)(OR)O—), phosphonate (—P(O)(OR)O—), saturated and nonsaturated cyclic groups, and saturated and nonsaturated heterocyclic groups; and wherein R is selected from the group consisting of H, linear, branched or cyclical alkyl groups, and which may contain therein additional functional groups or hetero atoms.

4. The composition according to claim 1, wherein the capping groups C contain further groups selected from the groups consisting of S, N, O, (—S—S)—, oxypropylene, oxybutylene, amide —C(O)NH— or C(O)NR—, —S-succinimido, amino (—NR—), carboxylic ester (—C(O)O—), sulfonamide (—S(O)$_2$—NR—), carbamate (—O—C(O)—NR—), carbonate (—O—C(O)—O—), sulfone (—S(O)$_2$—), ether (—O—), oxime (—CR=N—O—), hydrazone (—CR=N—NR—), urea (—NR—C(O)—NR—), thiourea (—NR—C(S)—NR—), carbohydrate, glyceryl, phosphate (—O—P(O)(OR)O—), phosphonate (—P(O)(OR)O—), saturated and nonsaturated cyclic groups, and saturated or nonsaturated heterocyclic groups; and wherein R is selected from the group consisting of H, linear, branched or cyclical alkyl groups, and which may contain therein additional functional groups or hetero atoms.

5. The composition of claim 1, wherein the biologically active moiety is a somatropin.

6. The composition of claim 1, wherein the cleavable linker L comprises a hydrolysable ester bond and the carbamate.

7. The composition of claim 6, wherein the hydrolysable ester bond is a phenol ester.

8. A drug containing the composition of claim 1.

9. The composition of claim 1, wherein l is 2 or 3, and resulting in a structure of formula (VII) or (VIII):

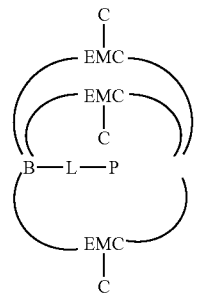
(VII)

-continued
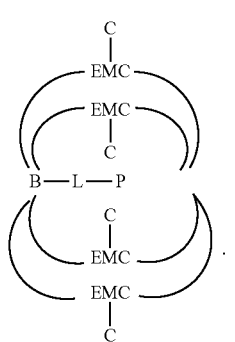
(VIII)
* * * * *